US012570600B2

(12) United States Patent
Lepak et al.

(10) Patent No.: US 12,570,600 B2
(45) Date of Patent: Mar. 10, 2026

(54) MULTIFUNCTIONAL LINKER COMPOUNDS

(71) Applicant: 20Bloc, Inc., Thousand Oaks, CA (US)

(72) Inventors: Alexander Lepak, Thousand Oaks, CA (US); Skylar J. Ferrara, Thousand Oaks, CA (US); Kai Lu, Thousand Oaks, CA (US); David Rozzell, Thousand Oaks, CA (US); Erik S. Goebel, Oakdale, MN (US)

(73) Assignee: 20Bloc, Inc., Thousand Oaks, CA (US)

( * ) Notice: Subject to any disclaimer, the term of this patent is extended or adjusted under 35 U.S.C. 154(b) by 0 days.

(21) Appl. No.: 19/036,816

(22) Filed: Jan. 24, 2025

(65) Prior Publication Data

US 2025/0243148 A1 Jul. 31, 2025

Related U.S. Application Data

(60) Provisional application No. 63/625,049, filed on Jan. 25, 2024.

(51) Int. Cl.

| | |
|---|---|
| *C07C 69/76* | (2006.01) |
| *C07C 69/34* | (2006.01) |
| *C07C 69/38* | (2006.01) |
| *C07C 69/42* | (2006.01) |
| *C07C 69/60* | (2006.01) |
| *C07C 69/82* | (2006.01) |
| *C07C 235/16* | (2006.01) |
| *C07C 237/12* | (2006.01) |
| *C07C 309/12* | (2006.01) |
| *C07C 311/19* | (2006.01) |

(52) U.S. Cl.

CPC .............. *C07C 69/76* (2013.01); *C07C 69/34* (2013.01); *C07C 69/38* (2013.01); *C07C 69/42* (2013.01); *C07C 69/60* (2013.01); *C07C 69/82* (2013.01); *C07C 235/16* (2013.01); *C07C 237/12* (2013.01); *C07C 309/12* (2013.01); *C07C 311/19* (2013.01)

(58) Field of Classification Search

CPC ....... C07C 69/34; C07C 69/76; C07C 235/16; C07C 237/12; C07C 309/12

See application file for complete search history.

(56) References Cited

U.S. PATENT DOCUMENTS

| | | | | |
|---|---|---|---|---|
| 5,399,671 | A | 3/1995 | Kluger et al. | |
| 9,351,980 | B2 * | 5/2016 | Perry | C07C 235/88 |
| 2004/0116293 | A1 | 6/2004 | Silverman et al. | |
| 2013/0035317 | A1 | 2/2013 | Perry et al. | |
| 2020/0016242 | A1 | 1/2020 | Kluger et al. | |

FOREIGN PATENT DOCUMENTS

| | | |
|---|---|---|
| CA | 2309236 A1 | 11/2001 |

OTHER PUBLICATIONS

Wood et al. Structural Specificities in Acylation of Hemoglobin and Sickle Hemoglobin by Diaspirins. Journal of Biological Chemistry, vol. 256, No. 13, 7046-7052. (Year: 1981).*

Carey, Organic Chemistry, 2nd edition, McGraw-Hill Book Company, 1992, 6 pages.

Delaney et al., "Alternative Diaspirins for Modification of Hemoglobin and Sickle Hemoglobin" Archives of Biochemistry and Biophysics, Feb. 1, 1984, vol. 228, No. 2, pp. 627-638.

Invitation to Pay Additional fees for International Application No. PCT/US2025/012981, mailed Mar. 19, 2025, 2 pages.

Kluger et al., "Trimesoyltris(3,5-dibromosalicylate): Specificity of Reactions of a Trifunctional Acylating Agent with Hemoglobin" J. Am. Chem. Soc., 1992, 114, pp. 9275-9279.

Neises et al., "Simple Method for the Esterification of Carboxylic Acids" Angew. Chem. Int. Ed, Jul. 1978, vol. 17, Issue 7, pp. 522-524.

Walder et al., "Diaspirins That Cross-Link Beta Chains of Hemoglobin: Bis(3,5- dibromosalicyl) Succinate and Bis(3,5-dibromosalicyl) Fumarate" Biochemistry, Oct. 2, 1979, vol. 18, No. 20, 6 pages.

Zaugg et al., "Modification of Hemoglobin with Analogs of Aspirin" The Journal of Biological Chemistry, 1980, vol. 255, No. 7, pp. 2816-2821.

International Search Report and Written Opinion for PCT Application No. PCT/US2025/012981 mailed May 20, 2025, 11 pages.

Invitation to Pay Additional fees for PCT Application No. PCT/US2025/029570, mailed Jun. 24, 2025, 3 pages.

Lima M.C.P., et al., "Stroma-Free Hemoglobin from Bovine Blood" Artificial Cells, Blood Substitutes, and Biotechnology, 2007, vol. 35, pp. 431-447.

Singh, et al., "Strain-promoted azide-alkyne cycloaddition for protein-protein coupling in the formation of a bis-hemoglobin as a copper-free oxygen carrier", Organic & Biomolecular Chemistry, Oct. 2, 20165, 14(42), pp. 10011-10017.

Yu Z, et al., "Structural Characterization of Human Hemoglobin Crosslinked by Bis(3,5-dibromosalicyl) Fumarate Using Mass Spectrometric Techniques" Protein Science, Dec. 6, 1997(12), pp. 2568-2577.

International Search Report and Written Opinion for PCT Application No. PCT/US2025/029570 mailed Aug. 19, 2025, 13 pages.

Singh S, et al., "Subunit-directed click coupling via doubly cross-linked hemoglobin efficiently produces readily purified functional bis-tetrameric oxygen carriers", Org Biomol Chem. Dec. 7, 2015;13(45):pp. 11118-11128. doi: 10.1039/c50b01755f. Epub Sep. 24, 2015.

* cited by examiner

*Primary Examiner* — Sikarl A Witherspoon

(74) *Attorney, Agent, or Firm* — Cooley LLP

(57) ABSTRACT

Provided herein are compounds of formula (I), (I)

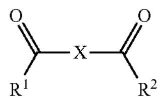

or salt, stereoisomer, or deuterated form thereof, wherein X, $R^1$, and $R^2$ are defined herein. Also provided herein are conjugated compositions comprising reacted units of a molecule (e.g., a protein) and a compound of formula (I), or salt, stereoisomer, or deuterated form thereof.

42 Claims, 20 Drawing Sheets

Type 1 linker

1: X= Cl or Phenolester

2

3: Y=Cl or OH

4: R=H or t-Bu 5-amino IA

8

*t*-Bu Type 2 linker

Type 2 linker

| Peak# | Ret. Time | Area | Area% | Relative Retention Time |
|---|---|---|---|---|
| 1 | 19.008 | 118634 | 1.966 | -- |
| 2 | 20.370 | 5915121 | 98.034 | -- |
| Total | | 6033755 | 100.000 | |

MULTIFUNCTIONAL LINKER COMPOUNDS

CROSS-REFERENCE TO RELATED APPLICATION

This application claims priority to U.S. Provisional Patent Application No. 63/625,049, filed on Jan. 25, 2024, the content of which is hereby incorporated by reference in its entirety for all purposes.

BACKGROUND

The covalent labeling and conjugation of proteins can be useful in numerous biological applications. For example, fluorophores or detection enzymes can be utilized to label purified proteins or target-specific antibodies for specific protein detection in immunoassays and bioimaging. Biotinylation, another prevalent method, involves attaching biotin to the target protein, enabling high-affinity binding interactions with avidin/streptavidin-conjugated components.

Although commercial reagents and kits are available for both conjugation and labeling methods, there is a need to develop novel linkers and technologies to modify biochemical properties, such as the modification and stabilization of conjugated molecules (e.g., proteins) and/or providing functionalization site(s) for subsequent modifications. These novel linkers enable the customization of molecular characteristics for specific applications and the development of novel molecules with enhanced functionalities. For example, linkers can be developed to cross-link multiple regions of the same molecule (e.g., intramolecular linker) and/or cross-link multiple molecules (e.g., intermolecular linker). In some cases, one linker can function both as an intramolecular linker and intermolecular linker.

SUMMARY

In some aspects, the present disclosure provides a compound of formula (I-1):

(I-1)

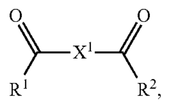

or a salt, a stereoisomer, or a deuterated form thereof, wherein:

$X^1$ is arylene or heteroarylene, wherein $X^1$ is optionally substituted with 1 or 2 $R^3$ as permitted by valency;

$R^1$ and $R^2$ are each independently a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-12}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50, with the proviso that:

if $X^1$ is

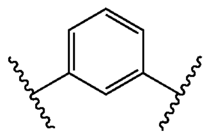

, then the leaving group is not

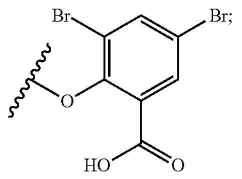

and if $X^1$ is an arylene substituted with 1 $R^3$, then $R^3$ is different from —C(O)—$R^1$ or —C(O)—$R^2$.

In embodiments, the compound of formula (I-1), or a salt, or a stereoisomer thereof, comprises one or more $^{13}C$ isotopes of carbon atoms occurring in the compound.

In embodiments, $X^1$ is $C_{6-10}$ arylene optionally substituted with 1 or 2 $R^3$ as permitted by valency.

In embodiments, $X^1$ is

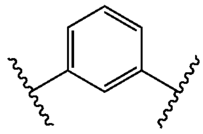

or

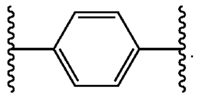

.

In embodiments, $X^1$ is $C_{6-10}$ arylene substituted with —C(O)—$R^1$, and wherein $R^1$ is —OH, halogen, or a leaving group. In embodiments, $R^1$ is a leaving group. In embodiments, $R^1$ is a leaving group which is

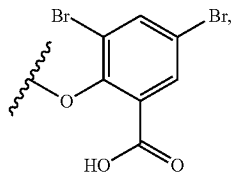 [SMILES: *Oc1c(Br)cc(Br)cc1C(=O)O]

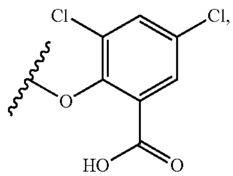

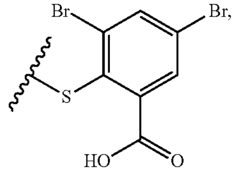

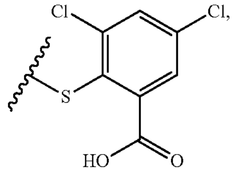

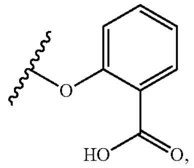

or

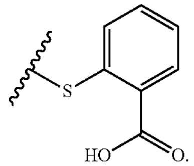

In embodiments, $X^1$ is

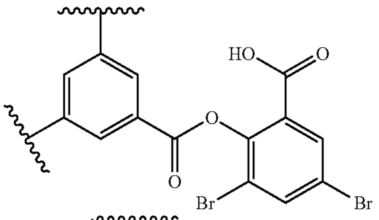 or

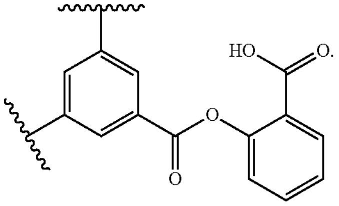.

In embodiments, $X^1$ is $C_{6-10}$ arylene substituted with —C(O)NH—($C_{1-12}$ alkylene)-$(OCH_2CH_2)_m$—$(CH_2)_n$—$N_3$, or —NHC(O)—($C_{1-12}$ alkylene)-$(OCH_2CH_2)_m$—$(CH_2)_n$—$N_3$, and wherein each m is independently an integer of 1-200, and each n is independently an integer of 0-100. In embodiments, $X^1$ is $C_{6-10}$ arylene substituted with —C(O)NH—($C_{1-6}$ alkylene)-$(OCH_2CH_2)_m$—$N_3$, and wherein m is an integer of 2-50. In embodiments, $X^1$ is

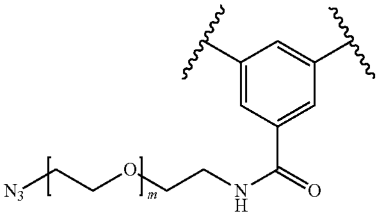, and wherein m is 4 or 9.

In embodiments, $X^1$ is $C_{6-10}$ arylene substituted with —NHC(O)—($C_{1-6}$ alkylene)-$(OCH_2CH_2)_m$—$N_3$, and wherein m is an integer of 2-50. In embodiments, $X^1$ is

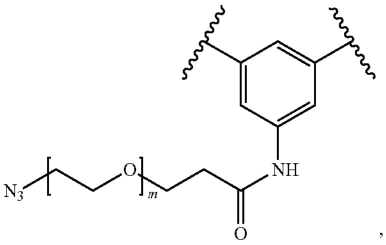, and wherein m is 4 or 9.

In some aspects, the present disclosure provides a compound of formula (I-2):

(I-2)

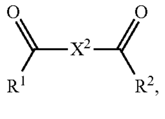

or a salt, a stereoisomer, or a deuterated form thereof, wherein:

$X^2$ is -$L^1$-$NR^A$-$L^2$, $R^1$ and $R^2$ are each independently a leaving group;

$R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-$(OCH_2CH_2)_m$—$(CH_2)_n$—$N_3$, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-12}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

In embodiments of the compounds of formula (I-2), or a salt, a stereoisomer, or a deuterated form thereof, $R^A$ is H, —$C_{1-6}$ alkyl, aryl, —C(O)-aryl, —$SO_2$($C_{1-6}$ alkyl), —$SO_2$-aryl, or —($C_{1-12}$ alkylene)-$(OCH_2CH_2)_m$—$(CH_2)_n$—$N_3$, wherein m is an integer of 1-50, n is an integer of 0-25, and each alkyl, aryl, or alkylene is optionally and independently substituted with —$C_{1-6}$ alkyl; and $L^1$ and $L^2$ are each independently $C_{1-6}$ alkylene, $C_{2-6}$ alkenylene, $C_{2-6}$ alkynylene, $C_{3-6}$ cycloalkylene, $C_{3-6}$ cycloalkenylene, arylene, or heteroarylene, wherein $L^1$ and $L^2$ are optionally and independently substituted with 1-3 $R^3$.

In embodiments, $R^A$ is H, and $L^1$ and $L^2$ are each independently $C_{1-6}$ alkylene or $C_{2-6}$ alkenylene. In embodiments, $X^2$ is

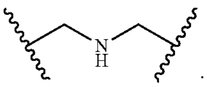 [SMILES: *CNC*].

In embodiments, $R^A$ is $C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl. In embodiments, $X^2$ is

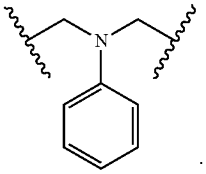 [SMILES: *CN(C*)c1ccccc1].

In embodiments, $R^A$ is —$SO_2$—$C_{1-6}$ alkyl, and $L^1$ and $L^2$ are each independently $C_{1-6}$ alkylene, or $C_{2-6}$ alkenylene. In embodiments, $X^2$ is

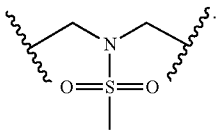 [SMILES: *CN(C*)S(C)(=O)=O]

In embodiments, $R^A$ is —$SO_2$—$C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl. In embodiments, $X^2$ is

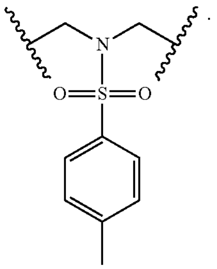 [SMILES: *CN(C*)S(=O)(=O)c1ccc(C)cc1]

In embodiments, $R^A$ is —C(O)—$C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl. In embodiments, $X^2$ is

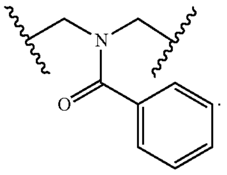 [SMILES: *CN(C*)C(=O)c1ccccc1]

In embodiments, $R^A$ is —($C_{1-6}$ alkylene)-$(OCH_2CH_2)_m$—$(CH_2)_n$—$N_3$, and $L^1$ and $L^2$ are each independently $C_{1-6}$ alkylene, or $C_{2-6}$ alkenylene, wherein m is an integer of 1-50, and n is an integer of 0-25. In embodiments, $X^2$ is

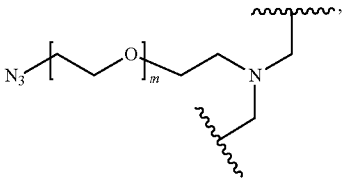

and m is 3.

In some aspects, the present disclosure provides a compound of formula (I-3):

(I-3)

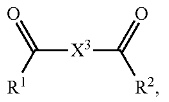

or a salt, a stereoisomer, or a deuterated form thereof, wherein:

$X^3$ is $C_{1-24}$ alkylene, $C_{2-24}$ alkenylene, or $C_{2-24}$ alkynylene, wherein $X^2$ is optionally substituted with 1-6 $R^3$ as permitted by valency;

$R^1$ and $R^2$ are each independently a leaving group, with the proviso that when $X^3$ is unsubstituted, then the leaving group is not

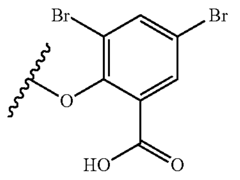 or 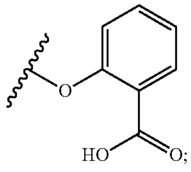

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-12}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

In embodiments, the compound of formula (I-3), or a salt, or a stereoisomer thereof, comprises one or more $^{13}C$ isotopes of carbon atoms occurring in the compound.

In embodiments of the compounds of formula (I-3), or a salt, a stereoisomer, or a deuterated form thereof, $X^3$ is $C_{1-12}$ alkylene, $C_{2-12}$ alkenylene, or $C_{2-12}$ alkynylene, each of which is optionally substituted with 1-6 $R^3$ as permitted by valency.

In embodiments, $X^3$ is $C_{1-6}$ alkylene, $C_{2-6}$ alkenylene, or $C_{2-6}$ alkynylene, each of which is optionally substituted with 1 or 2 $R^3$ as permitted by valency.

In embodiments, $X^3$ is $C_{1-6}$ alkylene optionally substituted with 1 or 2 $R^3$ as permitted by valency. In embodiments, $X^3$ is

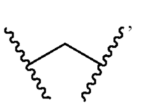, 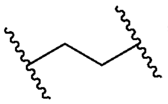, 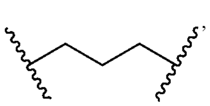,

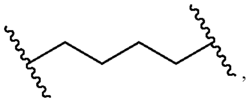,

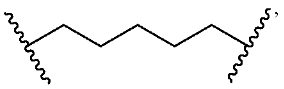, or

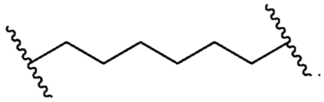

In embodiments, $X^3$ is $C_{1-6}$ alkylene substituted with —S—($C_{1-6}$ alkylene)-$(OCH_2CH_2)_m$—$(CH_2)_n$—$N_3$, and wherein m is an integer of 1-50, and n is an integer of 0-25. In embodiments, $X^3$ is

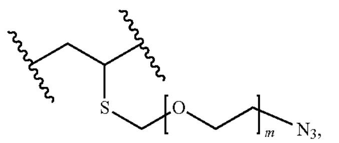

and wherein m is an integer of 1-25. In embodiments, $X^3$ is

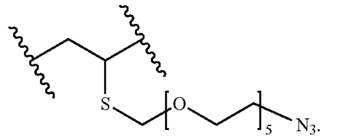

In embodiments, $X^3$ is $C_{1-6}$ alkylene substituted with —($C_{1-12}$ alkylene)-$N_3$. In embodiments, $X^3$ is $C_{1-6}$ alkylene substituted with —($C_{2-8}$ alkylene)-$N_3$. In embodiments, $X^3$ is

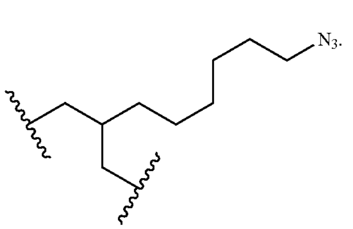 [SMILES: *CC(C*)CCCCCCN=[N+]=[N-]]

In embodiments, $X^3$ is $C_{2-6}$ alkenylene optionally substituted with 1 or 2 $R^3$ as permitted by valency. In embodiments, $X^3$ is or

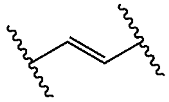
or
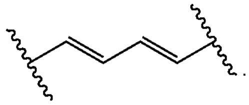

In embodiments, $X^3$ is $C_{2-6}$ alkynylene optionally substituted with 1 or 2 $R^3$ as permitted by valency. In embodiments, $X^3$ is

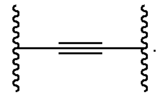 [SMILES: *C#C*]

In some aspects, the present disclosure provides a compound of formula (I-4):

(I-4)

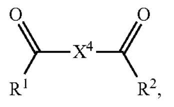

or a salt, a stereoisomer, or a deuterated form thereof, wherein:

$X^4$ is $C_{3-9}$ cycloalkylene, $C_{3-9}$ cycloalkenylene, 5-12 membered heterocyclylene containing 1 or 2 heteroatoms selected from N, S, or O, wherein $X^4$ is optionally substituted with 1-6 $R^3$ as permitted by valency;

$R^1$ and $R^2$ are each independently a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-12}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

In embodiments, the compound of formula (I-4), or a salt, or a stereoisomer thereof, comprises one or more $^{13}C$ isotopes of carbon atoms occurring in the compound.

In embodiments of the compound of formula (I-4), or a salt, a stereoisomer, or a deuterated form thereof, $X^4$ is $C_{3-9}$ cycloalkylene, $C_{3-9}$ cycloalkenylene, or 5-12 membered heterocyclylene, each of which is optionally substituted with 1 or 2 $R^3$ as permitted by valency.

In embodiments, $X^4$ is $C_{3-7}$ cycloalkylene optionally substituted with 1 or 2 $R^3$ as permitted by valency. In embodiments, $X^4$ is

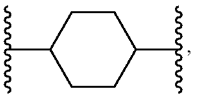,
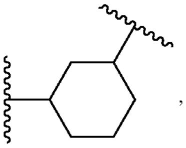, or
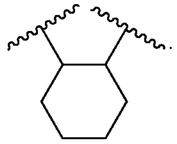.

In embodiments, $X^4$ is $C_{3-7}$ cycloalkenylene optionally substituted with 1 or 2 $R^3$ as permitted by valency. In embodiments, $X^4$ is

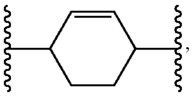,
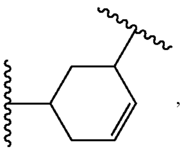,
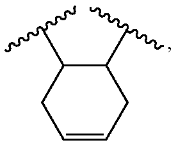,
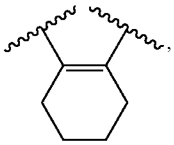, or
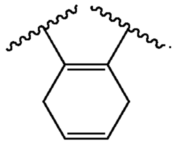.

In embodiments, $X^4$ is $C_{3-7}$ cycloalkenylene substituted with —($C_{1-6}$ alkylene)-$N_3$. In embodiments, $X^4$ is

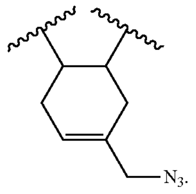 [SMILES: *C1CC=C(CN=[N+]=[N-])CC1*]

In embodiments, $C_{3-9}$ cycloalkylene, $C_{3-9}$ cycloalkenylene, or 5-12 membered heterocyclylene is a bridged ring system.

In embodiments, $X^4$ is a 5-12 membered heterocyclylene containing a heteroatom which is S or O, and wherein the heterocyclylene is optionally substituted with —($C_{1-6}$ alkylene)-$N_3$. In embodiments, $X^4$ is

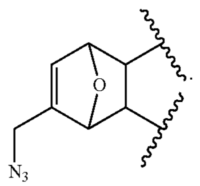 [SMILES: *C1C2C=C(CN=[N+]=[N-])C(O2)C1*]

In embodiments of the compound of formula (I-1), (I-2), (I-3), or (I-4), or a salt, a stereoisomer, or a deuterated form thereof, $R^1$ and $R^2$ are a leaving group, and the leaving group is

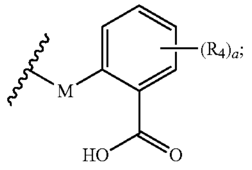

M is O or S;

each $R^4$ is independently halogen or —$C_{1-6}$ alkyl; and a is an integer of 0-4, with the proviso that:

if $X^1$ is

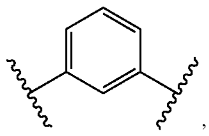 [SMILES: *c1cccc(*)c1]

then the leaving group is not

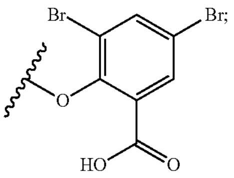

if $X^1$ is an arylene substituted with 1 $R^3$, then $R^3$ is different from —C(O)—$R^1$ or —C(O)—$R^2$; and when $X^3$ is unsubstituted, then the leaving group is not

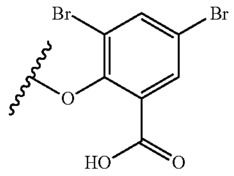

or

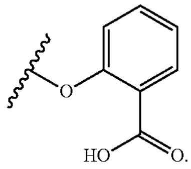

In embodiments of the compound of formula (I-1), (I-2), (I-3), or (I-4), or a salt, a stereoisomer, or a deuterated form thereof, the leaving group is

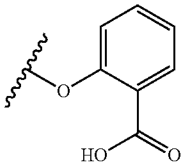

or

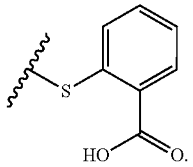

In embodiments of the compound of formula (I-1), (I-2), (I-3), or (I-4), or a salt, a stereoisomer, or a deuterated form thereof, the leaving group is

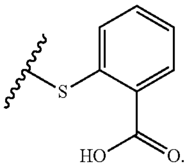

In embodiments of the compound of formula (I-1), (I-2), (I-3), or (I-4), or a salt, a stereoisomer, or a deuterated form thereof, a is 1, 2, or 3.

In embodiments of the compound of formula (I-1), (I-2), (I-3), or (I-4), or a salt, a stereoisomer, or a deuterated form thereof, each $R^4$ is halogen. In embodiments, each $R^4$ is independently —F, —Cl, or —Br. In embodiments, the leaving group is

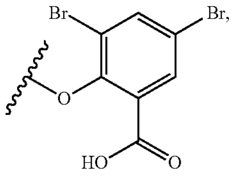 [SMILES: *Oc1c(Br)cc(Br)cc1C(=O)O]

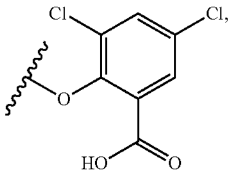

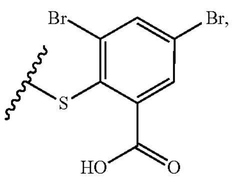

or

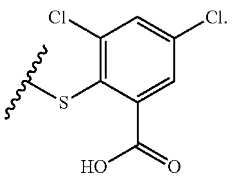

In embodiments, the leaving group is

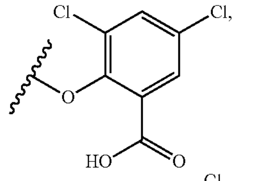

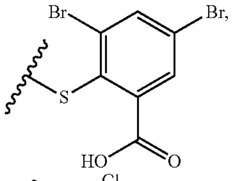

or

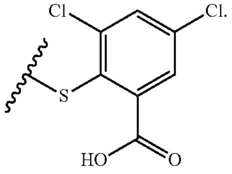

In embodiments of the compound of formula (I-1), (I-2), (I-3), or (I-4), or a salt, a stereoisomer, or a deuterated form thereof, $R^1$ and $R^2$ are a leaving group, and the leaving group is —O—($C_{1-6}$ alkylene)-$SO_3H$.

In embodiments, the leaving group is —O—($CH_2CH_2$)—$SO_3H$.

In some aspects, the present disclosure provides a compound of formula (I):

(I)

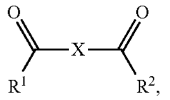

or a salt, a stereoisomer, or a deuterated form thereof, wherein:

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, arylene, heteroarylene, or -$L^1$-$NR^A$-$L^2$-, wherein X is optionally substituted with 1-6 $R^3$ as permitted by valency;

$R^1$ and $R^2$ are each independently —OH, halogen, or a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-($OCH_2CH_2$)$_m$—($CH_2$)$_n$—$N_3$, —C(O)NH—($C_{1-12}$ alkylene)-($OCH_2CH_2$)$_m$—($CH_2$)$_n$—$N_3$, —NHC(O)—($C_{1-12}$ alkylene)-($OCH_2CH_2$)$_m$—($CH_2$)$_n$—$N_3$, —O—($C_{1-12}$ alkylene)-($OCH_2CH_2$)$_m$—($CH_2$)$_n$—$N_3$, —S—($C_{1-12}$ alkylene)-($OCH_2CH_2$)$_m$—($CH_2$)$_n$—$N_3$, or —C(O)—$R^1$, wherein each alkyl or alkylene is optionally and independently substituted with —$C_{1-6}$ alkyl, —OH, —CN, —$NO_2$, or halogen;

$R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-($OCH_2CH_2$)$_m$—($CH_2$)$_n$—$N_3$, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

In embodiments, the compound of formula (I), or a salt, or a stereoisomer thereof, comprises one or more $^{13}C$ isotopes of carbon atoms occurring in the compound.

In embodiments, $R^1$ and $R^2$ are a leaving group, and wherein:

the leaving group is

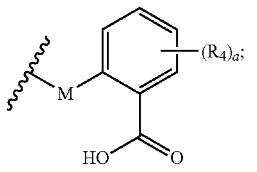

M is O or S;

each $R^4$ is independently halogen or —$C_{1-6}$ alkyl; and a is an integer of 0-4.

In embodiments, the leaving group is

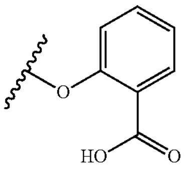

or

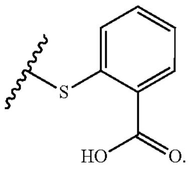

In embodiments, a is 1, 2, or 3.

In embodiments, each $R^4$ is halogen.

In embodiments, each $R^4$ is independently —F, —Cl, or —Br.

In embodiments, the leaving group is

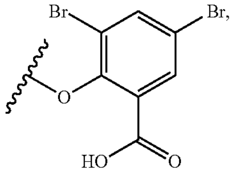

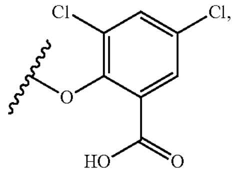

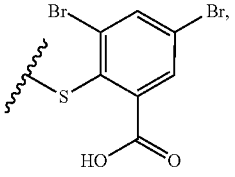

or

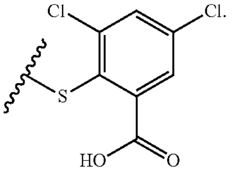

In embodiments, $R^1$ and $R^2$ are a leaving group, and wherein the leaving group is —O—($C_{1-6}$ alkylene)-$SO_3H$.

In embodiments, the leaving group is —O—($CH_2CH_2$)—$SO_3H$.

In embodiments, X is $C_{1-12}$ alkylene, $C_{2-12}$ alkenylene, or $C_{2-12}$ alkynylene, each of which is optionally substituted with 1-6 $R^3$ as permitted by valency.

In embodiments, X is $C_{1-6}$ alkylene, $C_{2-6}$ alkenylene, or $C_{2-6}$ alkynylene, each of which is optionally substituted with 1 or 2 $R^3$ as permitted by valency.

In embodiments, X is $C_{1-6}$ alkylene optionally substituted with 1 or 2 $R^3$ as permitted by valency.

In embodiments, X is

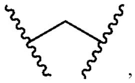, 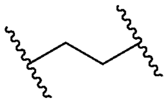, 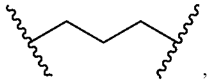, 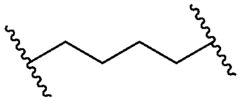, 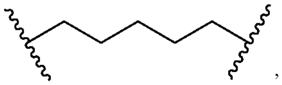, or 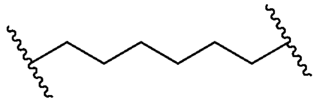.

In embodiments, X is $C_{1-6}$ alkylene substituted with —S—($C_{1-6}$ alkylene)-$(OCH_2CH_2)_m$—$(CH_2)_n$—$N_3$, and wherein m is an integer of 1-50, and n is an integer of 0-25.

In embodiments, X is

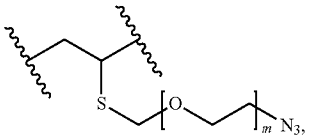

and wherein m is an integer of 1-25.

In embodiments, X is

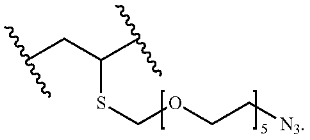

In embodiments, X is $C_{2-6}$ alkenylene optionally substituted with 1 or 2 $R^3$ as permitted by valency.

In embodiments, X is

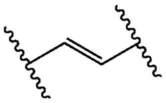 or 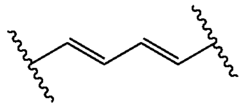.

In embodiments, X is $C_{2-6}$ alkynylene optionally substituted with 1 or 2 $R^3$ as permitted by valency.

In embodiments, X is

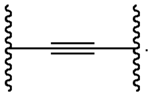 [SMILES: *C#C*].

In embodiments, X is $C_{3-9}$ cycloalkylene, $C_{3-9}$ cycloalkenylene, or 5-12 membered heterocyclylene, each of which is optionally substituted with 1 or 2 $R^3$ as permitted by valency.

In embodiments, X is $C_{3-7}$ cycloalkylene optionally substituted with 1 or 2 $R^3$ as permitted by valency.

In embodiments, X is

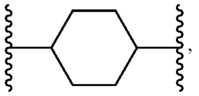, 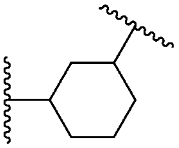, or 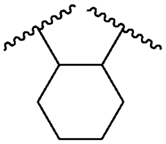.

In embodiments, X is $C_{3-7}$ cycloalkenylene optionally substituted with 1 or 2 $R^3$ as permitted by valency.

In embodiments, X is

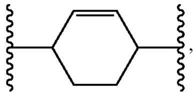, 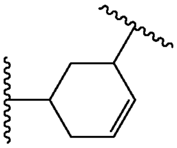, 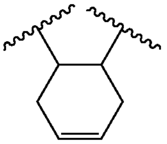, 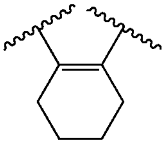, or 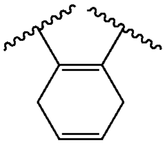.

In embodiments, X is $C_{3-7}$ cycloalkenylene substituted with —($C_{1-6}$ alkylene)-$N_3$.

In embodiments, X is $N_3$.

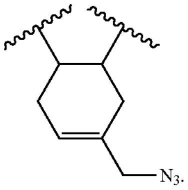 [SMILES: *C1CC=C(CN=[N+]=[N-])CC1*]

In embodiments, X is a 5-12 membered heterocyclylene containing a heteroatom which is S or O, and wherein the heterocyclylene is optionally substituted with —($C_{1-6}$ alkylene)-$N_3$.

In embodiments, X is

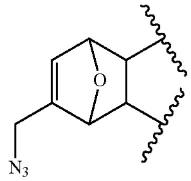.

In embodiments, X is arylene or heteroarylene, each of which is optionally substituted with 1 or 2 $R^3$ as permitted by valency.

In embodiments, X is $C_{6-10}$ arylene optionally substituted with 1 or 2 $R^3$ as permitted by valency.

In embodiments, X is

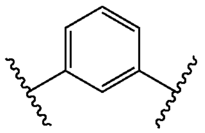

or

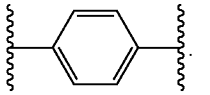

In embodiments, X is $C_{6-10}$ arylene substituted with —C(O)—$R^1$, and wherein $R^1$ is —OH, halogen, or a leaving group.

In embodiments, $R^1$ is a leaving group.

In embodiments, the leaving group is

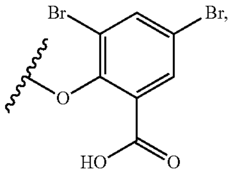

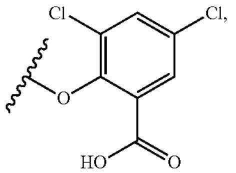

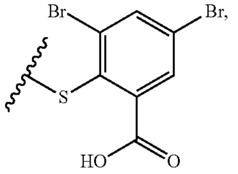

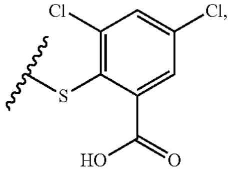

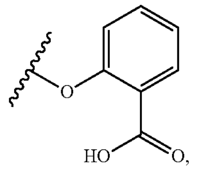

or

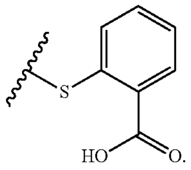

In embodiments, X is

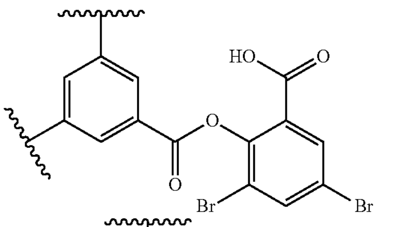

or

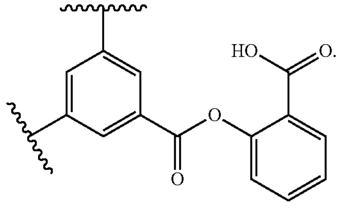

In embodiments, X is $C_{6-10}$ arylene substituted with —C(O)NH—($C_{1-12}$ alkylene)-($OCH_2CH_2$)$_m$—($CH_2$)$_n$—$N_3$, or —NHC(O)—($C_{1-12}$ alkylene)-($OCH_2CH_2$)$_m$—($CH_2$)$_n$—$N_3$, and wherein each m is independently an integer of 1-12, and each n is independently an integer of 0-6.

In embodiments, X is $C_{6-10}$ arylene substituted with —C(O)NH—($C_{1-6}$ alkylene)-($OCH_2CH_2$)$_m$—$N_3$, and wherein m is an integer of 3-10.

In embodiments, X is

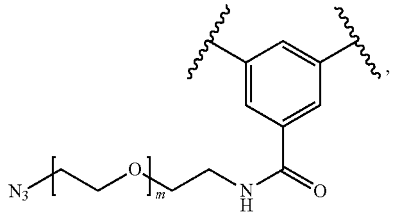

and wherein m is 4 or 9.

In embodiments, X is $C_{6-10}$ arylene substituted with —NHC(O)—($C_{1-6}$ alkylene)-($OCH_2CH_2$)$_m$—$N_3$, and wherein m is an integer of 3-10.

In embodiments, X is

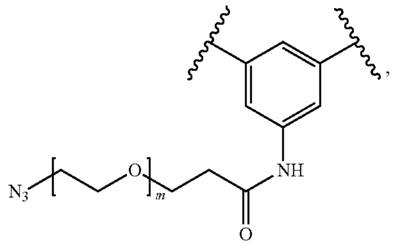

and wherein m is 4 or 9.

In embodiments, X is -$L^1$-$NR^A$-$L^2$-, and wherein:

$R^A$ is H, —$C_{1-6}$ alkyl, aryl, —C(O)-aryl, —$SO_2$($C_{1-6}$ alkyl), —$SO_2$-aryl, or —($C_{1-12}$ alkylene)-($OCH_2CH_2$)$_m$—($CH_2$)$_n$—$N_3$, wherein m is an integer of 1-12, n is an integer of 0-6, and each alkyl, aryl or alkylene is optionally and independently substituted with —$C_{1-6}$ alkyl; and $L^1$ and $L^2$ are each independently $C_{1-6}$ alkylene, $C_{2-6}$ alkenylene, $C_{2-6}$ alkynylene, $C_{3-6}$ cycloalkylene, $C_{3-6}$ cycloalkenylene, arylene, or heteroarylene, wherein $L^1$ and $L^2$ are optionally and independently substituted with 1-3 $R^3$.

In embodiments, $R^A$ is H, and $L^1$ and $L^2$ are each independently $C_{1-6}$ alkylene or $C_{2-6}$ alkenylene.

In embodiments, X is

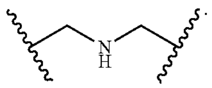 [SMILES: *CNC*]

In embodiments, $R^A$ is $C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl.

In embodiments, X is

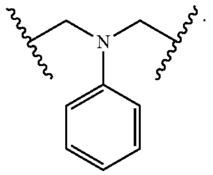 [SMILES: *CN(C*)c1ccccc1]

In embodiments, $R^A$ is $-SO_2-C_{1-6}$ alkyl, and $L^1$ and $L^2$ are each independently $C_{1-6}$ alkylene, or $C_{2-6}$ alkenylene.

In embodiments, X is

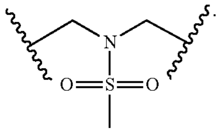 [SMILES: *CN(C*)S(C)(=O)=O]

In embodiments, $R^A$ is $-SO_2-C_{6-10}$ aryl, and $L^1$ and $L^2$ are each independently $C_{1-6}$ alkylene, or $C_{2-6}$ alkenylene, and wherein the aryl of $R^A$ is optionally substituted with $-C_{1-6}$ alkyl.

In embodiments, X is

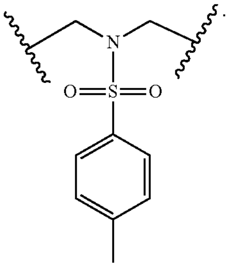 [SMILES: *CN(C*)S(=O)(=O)c1ccc(C)cc1]

In embodiments, $R^A$ is $-C(O)-C_{6-10}$ aryl, and $L^1$ and $L^2$ are each independently $C_{1-6}$ alkylene, or $C_{2-6}$ alkenylene, and wherein the aryl of $R^A$ is optionally substituted with $-C_{1-6}$ alkyl.

In embodiments, X is

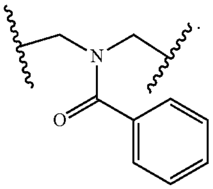 [SMILES: *CN(C*)C(=O)c1ccccc1]

In embodiments, $R^A$ is $-(C_{1-6}\text{ alkylene})-(OCH_2CH_2)_m-(CH_2)_n-N_3$, and $L^1$ and $L^2$ are each independently $C_{1-6}$ alkylene, or $C_{2-6}$ alkenylene, wherein m is an integer of 1-6, and n is an integer of 0-3.

In embodiments, X is

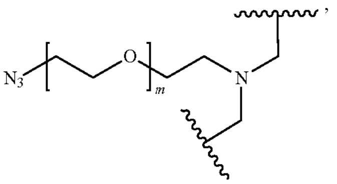

and m is 3.

In embodiments, the compound of formula (I) is:

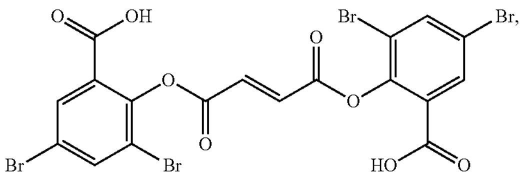

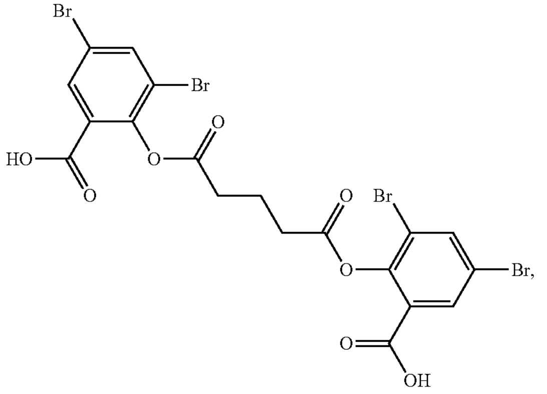

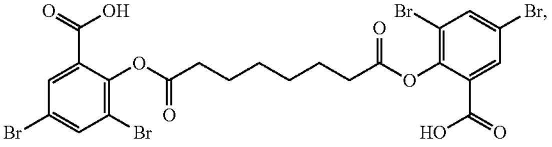

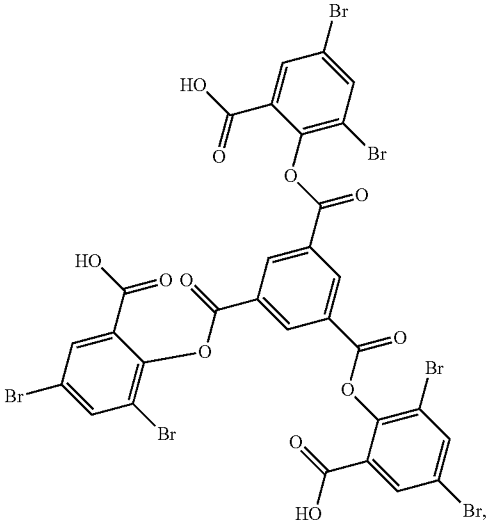

-continued
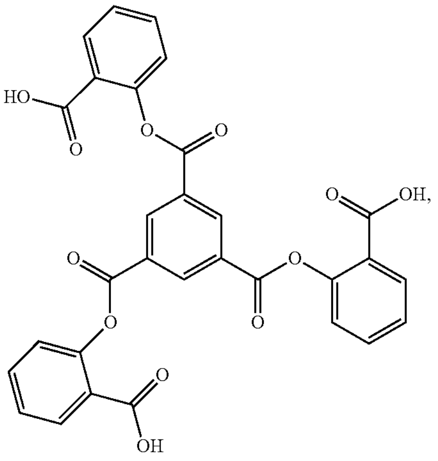
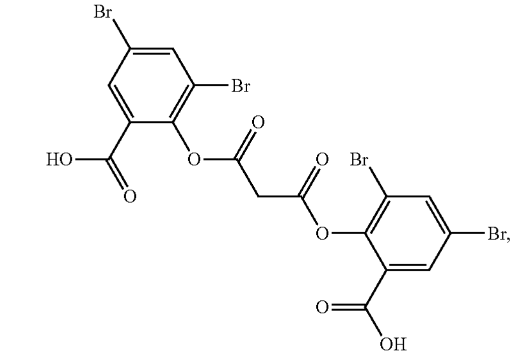
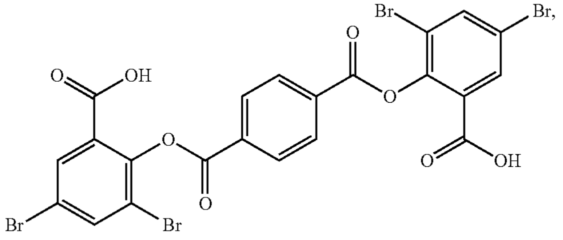
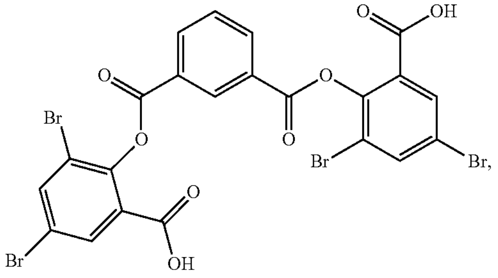
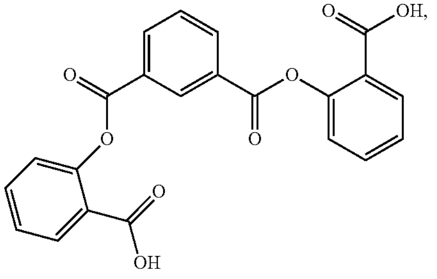
-continued
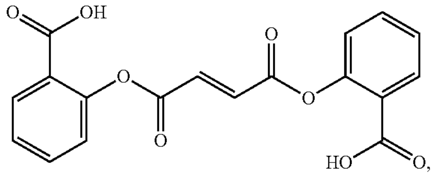
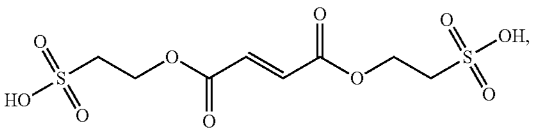
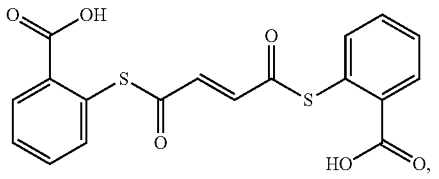
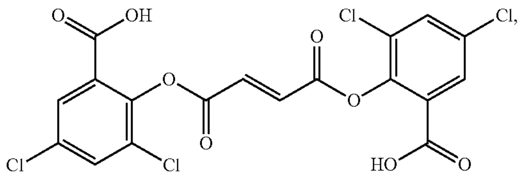
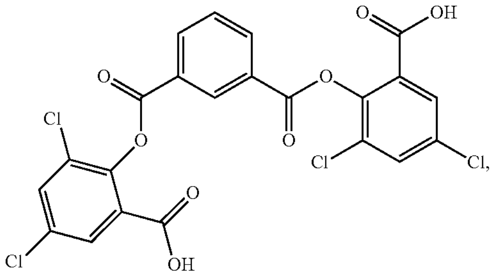
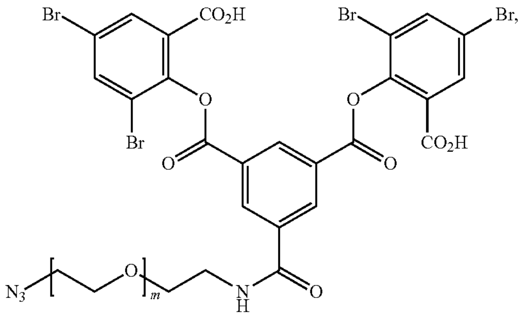
m = 4
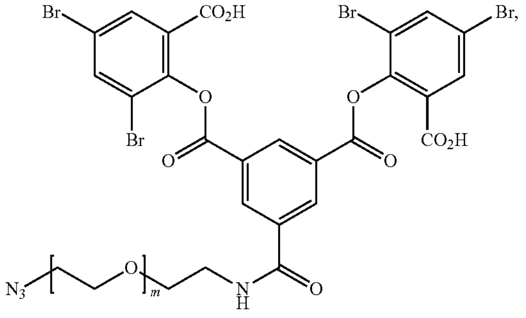
m = 9

-continued
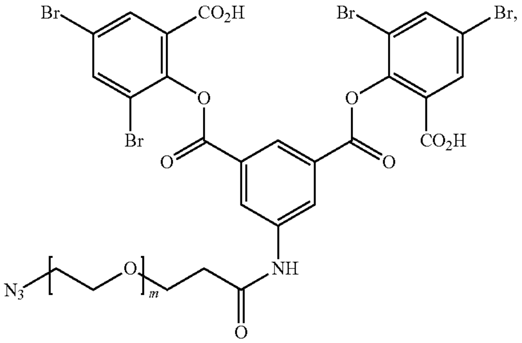
m = 4
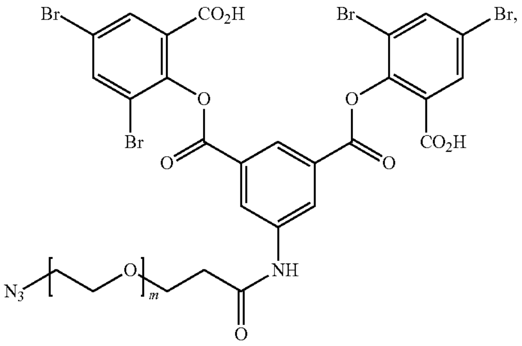
m = 9
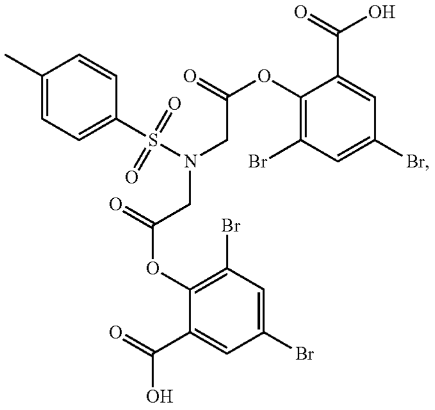
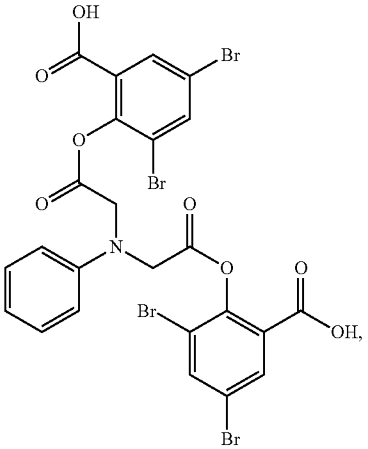
-continued
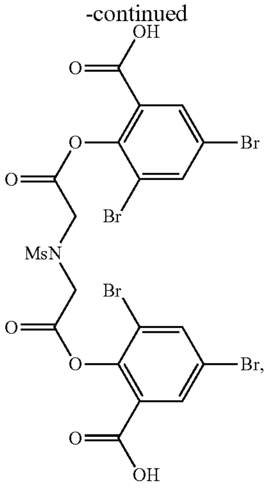
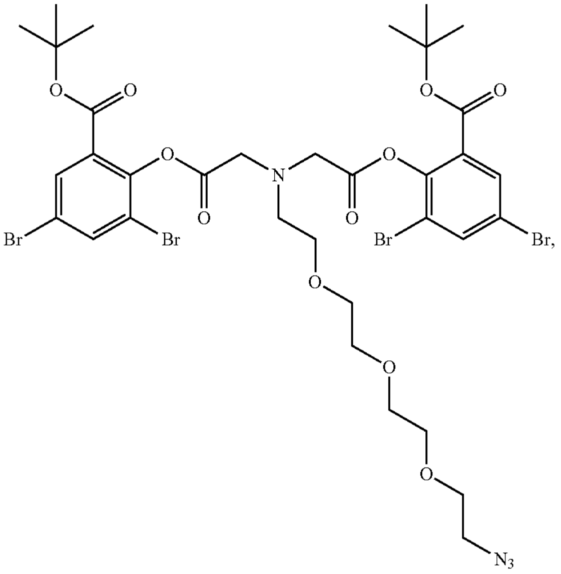
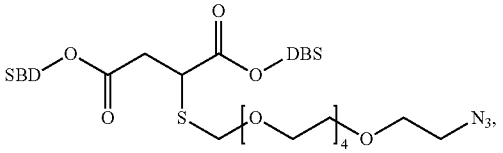
or
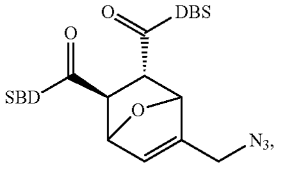
or a salt, a stereoisomer, or a deuterated form thereof, wherein DBS represents
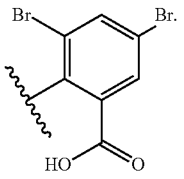 [SMILES: *c1c(Br)cc(Br)cc1C(=O)O]
In a further aspect, the present disclosure provides a compound of formula (I-1), which is:

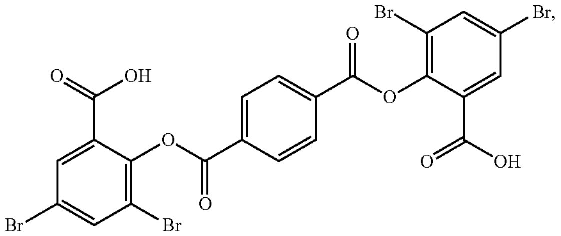
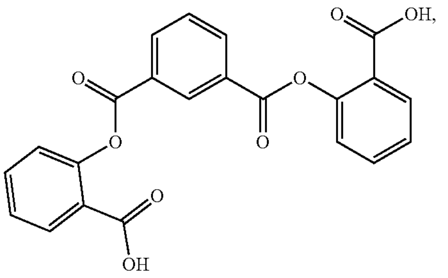
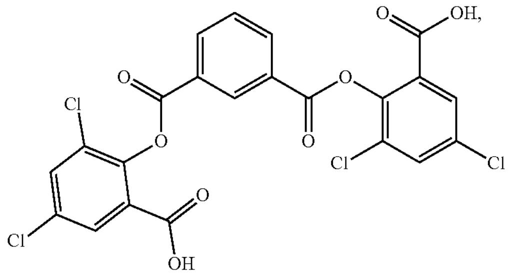
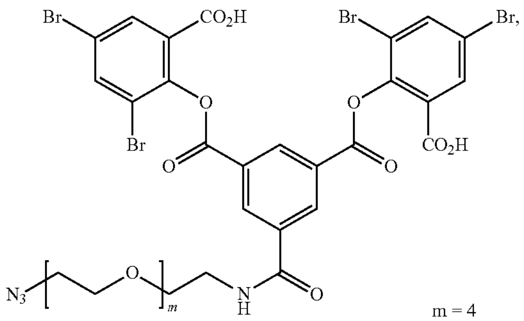
m = 4
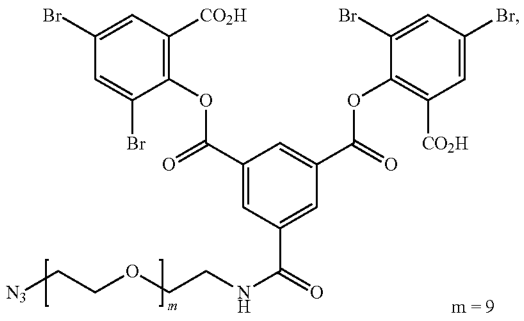
m = 9
-continued
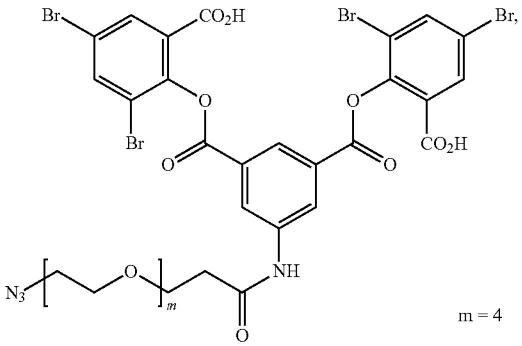
or
m = 4
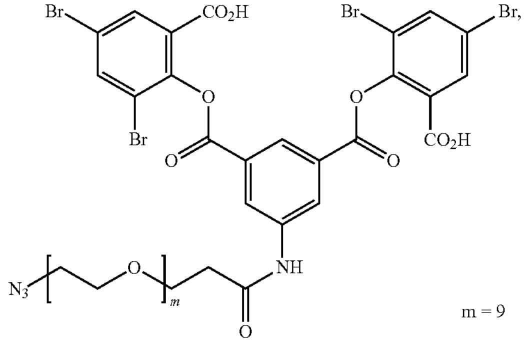
m = 9
or a salt, a stereoisomer, or a deuterated form thereof.
In a further aspect, the present disclosure provides a compound of formula (I-2), which is
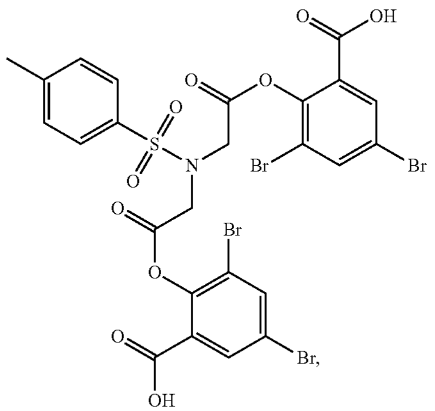
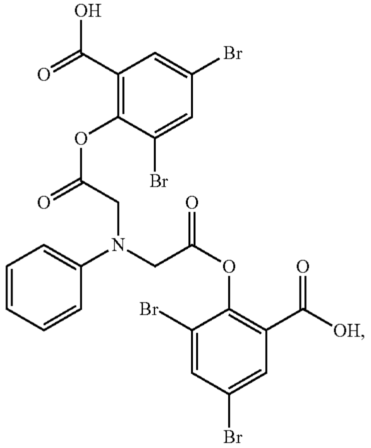

-continued

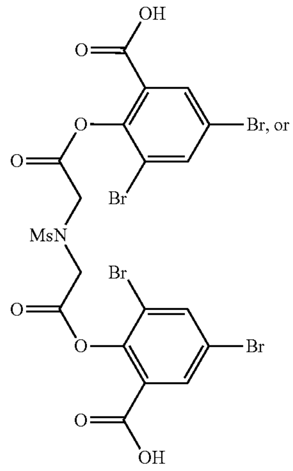

or

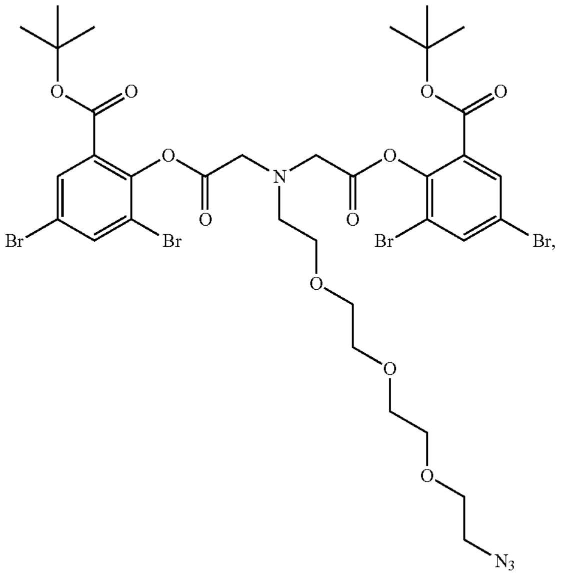 [SMILES: CC(C)(C)OC(=O)c1cc(Br)cc(Br)c1OC(=O)CN(CCOCCOCCOCCN=[N+]=[N-])CC(=O)Oc1c(Br)cc(Br)cc1C(=O)OC(C)(C)C]

or a salt, a stereoisomer, or a deuterated form thereof.

In a further aspect, the present disclosure provides a compound of formula (I-3), which is

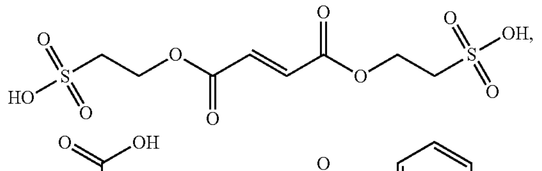

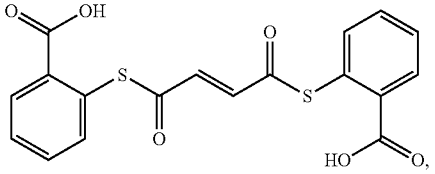

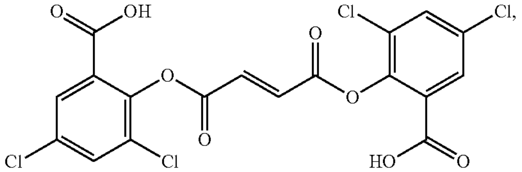

-continued

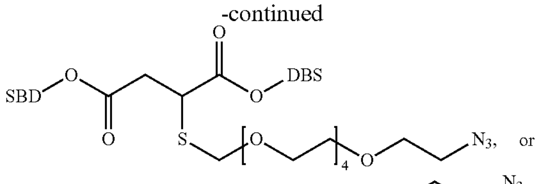

or

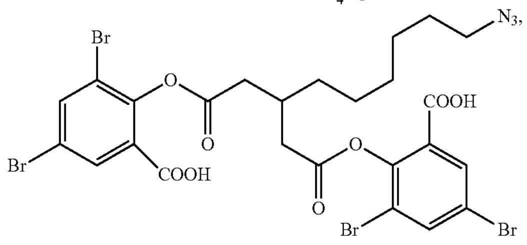

or a salt, a stereoisomer, or a deuterated form thereof, wherein DBS represents

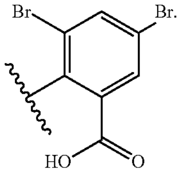 [SMILES: *c1c(Br)cc(Br)cc1C(=O)O]

In a further aspect, the present disclosure provides a compound of formula (I-4), which is

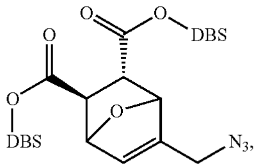

wherein DBS represents

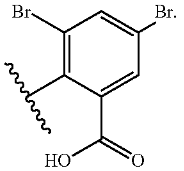 [SMILES: *c1c(Br)cc(Br)cc1C(=O)O]

In other aspects, the present disclosure provides a conjugated composition, comprising a reacted unit of a molecule and a compound of the present disclosure (e.g., the compound of any one of the aforementioned embodiments, or a salt, a stereoisomer, or a deuterated form thereof).

In embodiments, the molecule is a protein. In embodiments, the molecule is a protein comprising 2 or more lysine residues (i.e., Lys, K). In embodiments, the molecule is hemoglobin. In embodiments, the molecule is bovine hemoglobin.

In embodiments, the conjugated composition is obtained by crosslinking the molecule with the compound, or a salt, a stereoisomer, or a deuterated form thereof.

In embodiments, the molecule is a protein comprising 2 or more lysine residues and the conjugated composition is obtained by crosslinking 2 or more lysine residues of the protein with the compound, or a salt, a stereoisomer, or a deuterated form thereof.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
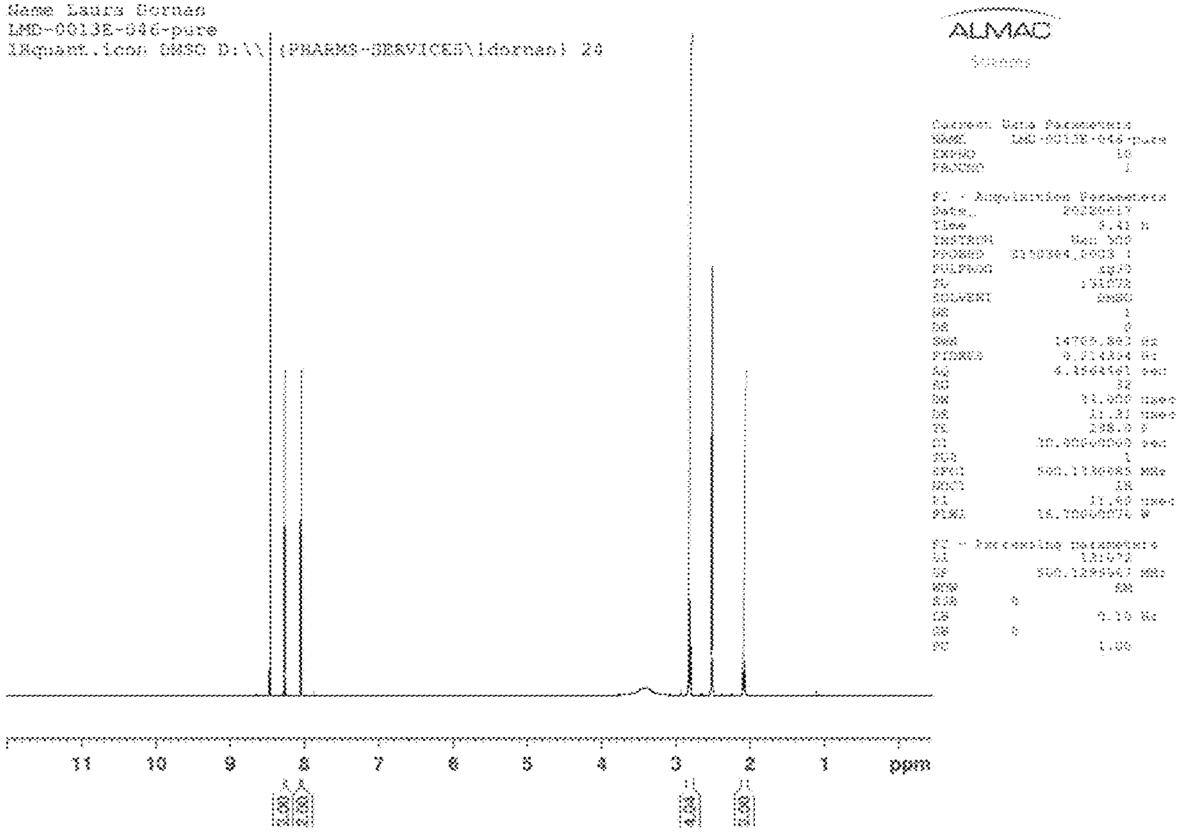
FIG. 1 is a $^1H$ nuclear magnetic resonance ($^1H$ NMR) spectrum of bis(3,5-dibromosalicyl)glutarate (DBSG).
Figure 2:
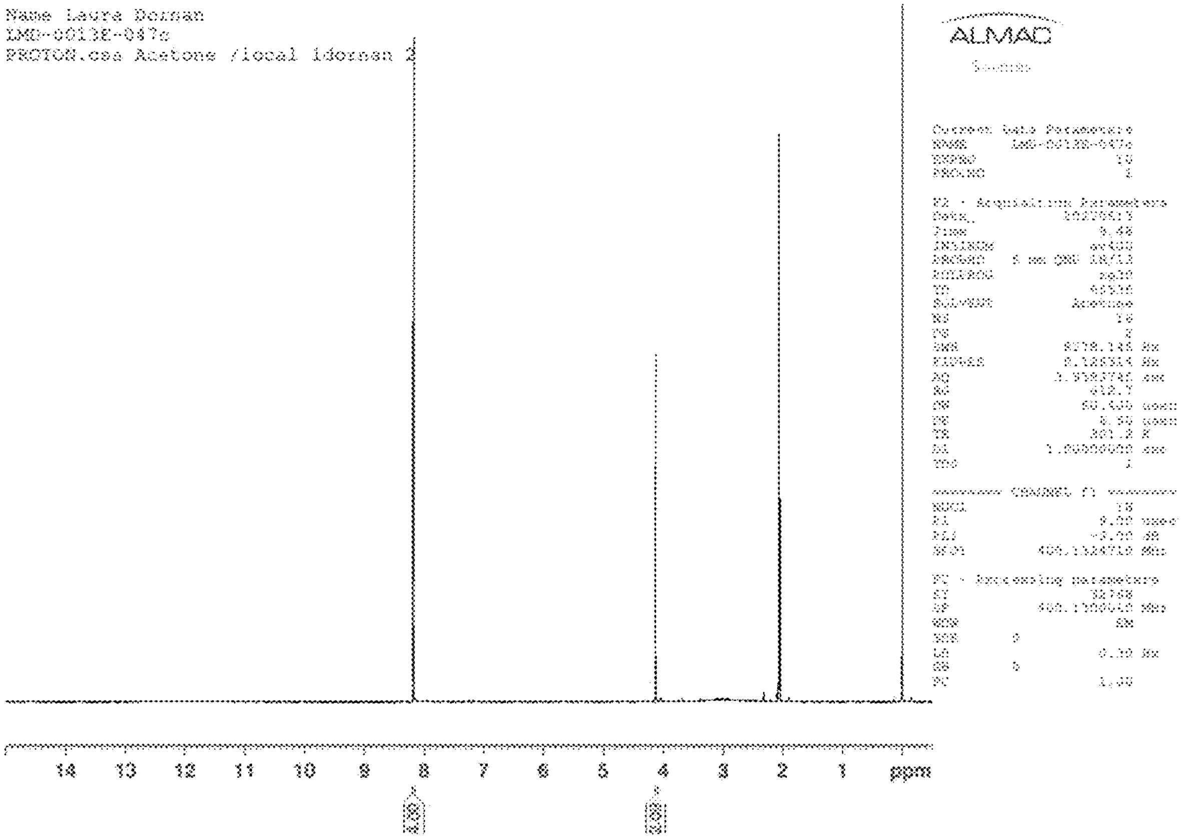
FIG. 2 is a $^1H$ NMR spectrum of bis(3,5-dibromosalicyl) malonate (DBSM).
Figure 3:
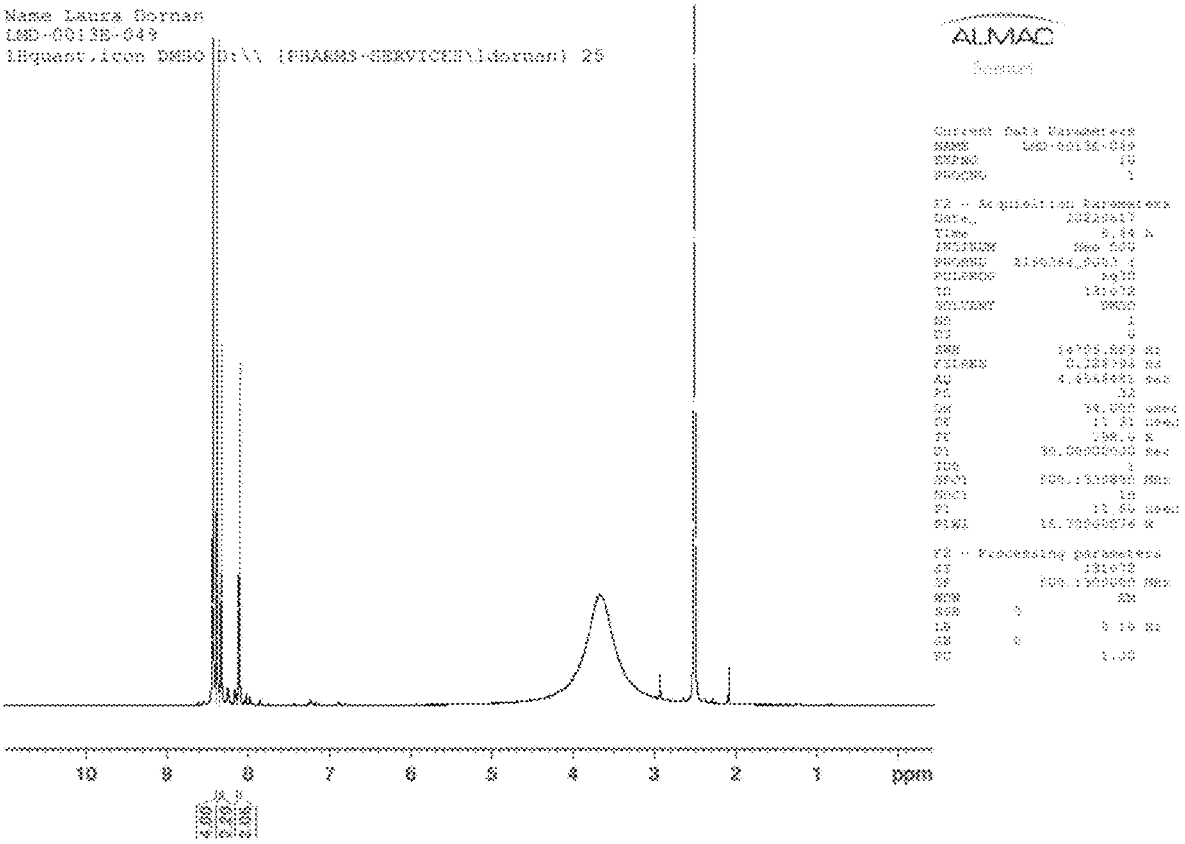
FIG. 3 is a $^1H$ NMR spectrum of bis(3,5-dibromosalicyl) terephthalate (DBST).
Figure 4:
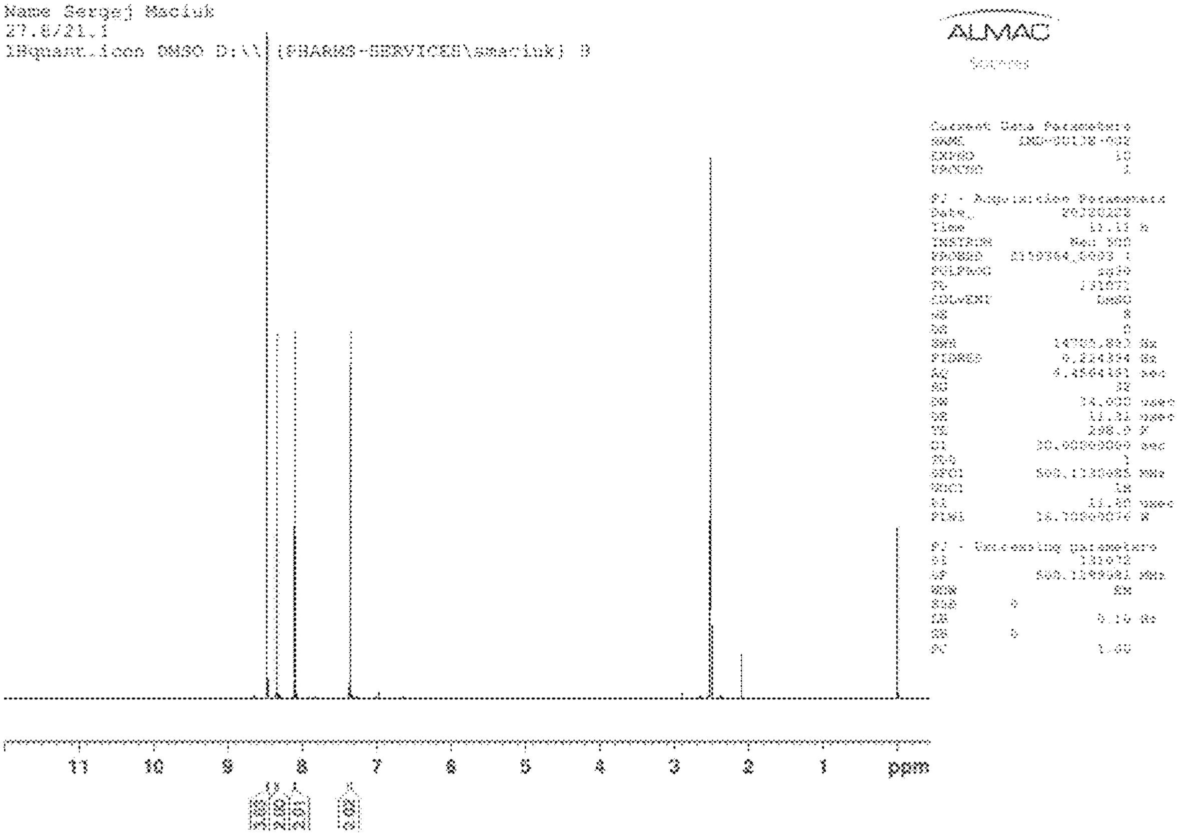
FIG. 4 is a $^1H$ NMR spectrum of bis(3,5-dibromosalicyl) fumarate (DBSF).
Figure 5:
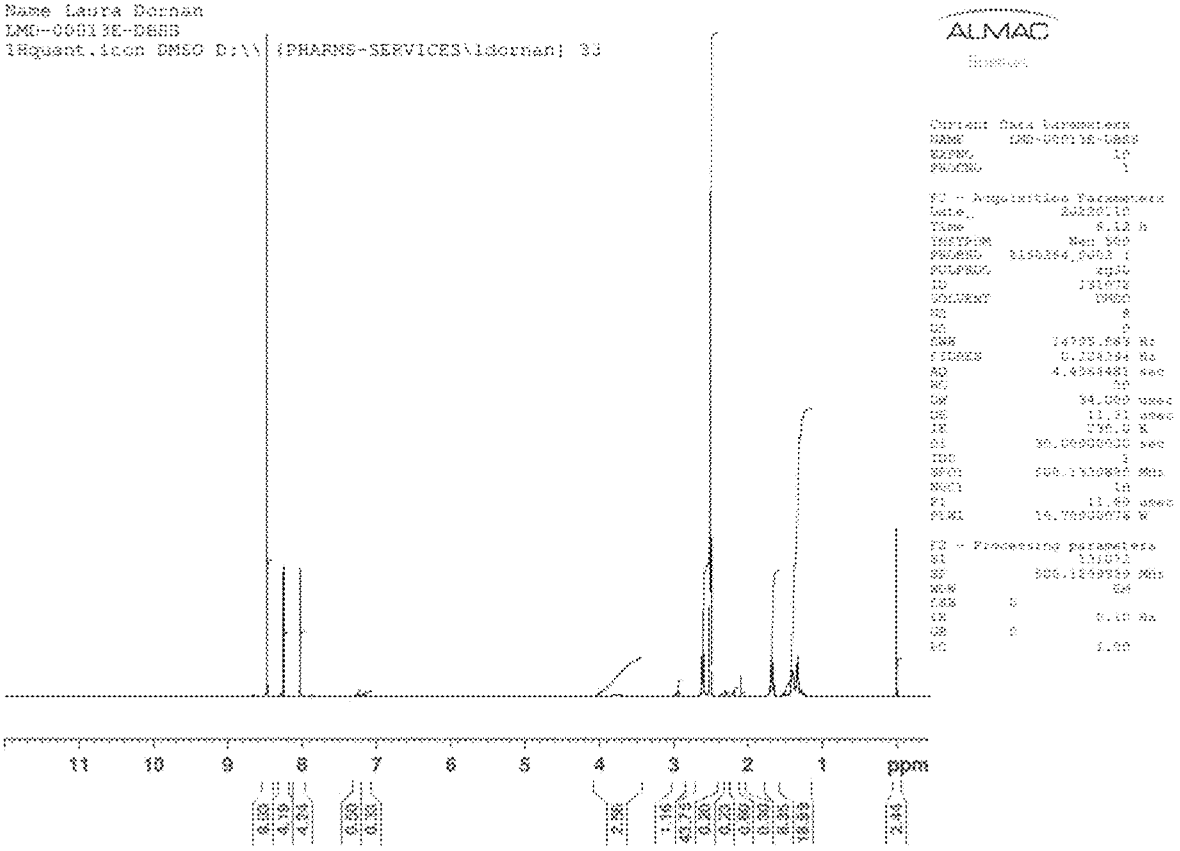
FIG. 5 is a $^1H$ NMR spectrum of di-bromo-salicyl-subarate (DBSS).
Figure 6:
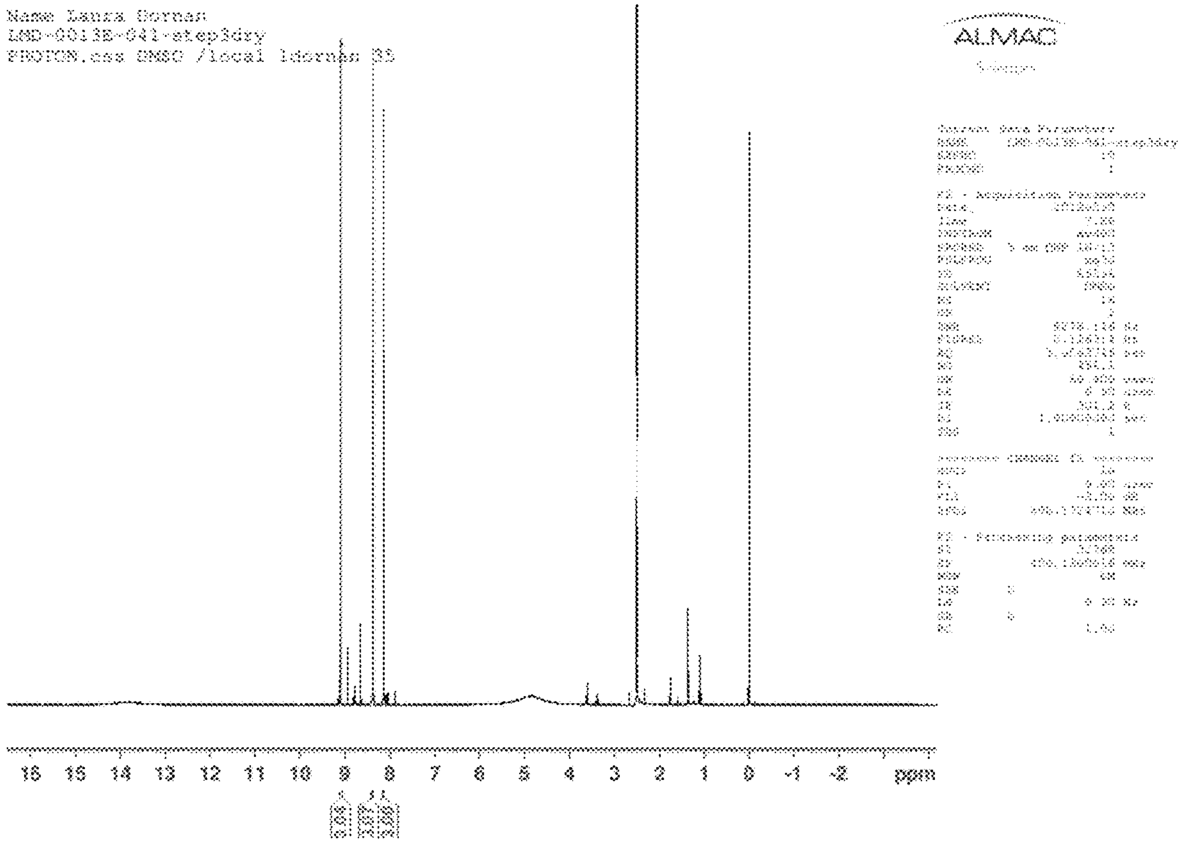
FIG. 6 is a $^1H$ NMR spectrum of trimesoyltris(1-(tert-butoxycarbonyl)-3,5-dibromosalicylate (TTDS).

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

Listed below are definitions of various terms used in the specification and claims to describe the present disclosure.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, exemplary methods, and materials are described herein.

As used herein, the term "and/or" includes any and all combinations of one or more of the associated listed items. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

As used in the specification and the appended claims, the singular forms "a," "an" and "the" include plural referents unless the context clearly dictates otherwise.

The term "about" when immediately preceding a numerical value means a range of plus or minus an acceptable degree of variation in the art. In some embodiments, the term "about" encompasses 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 50.5. Furthermore, the phrases "less than about" a value or "greater than about" a value should be understood in view of the definition of the term "about" provided herein.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The terms below, as used herein, have the following meanings, unless indicated otherwise:

"Cyano" refers to the —CN radical.

"Hydroxy" or "hydroxyl" refers to the —OH radical.

"Oxo" refers to the =O substituent.

"Halo" or "halogen" refers to fluorine (fluoro, —F), chlorine (chloro, —Cl), bromine (bromo, —Br), or iodine (iodo, —I).

"Alkyl" or "alkyl group" refers to a fully saturated, straight or branched hydrocarbon chain group, which is attached to the rest of the molecule by a single bond. Alkyls comprising any number of carbon atoms, including but not limited to from 1 to 12 are included. For example, "$C_1$ to $C_6$ alkyl" or "$C_{1-6}$ alkyl" denotes alkyl chain having 1 to 6 carbon atoms. The alkyl groups typically include $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, and specifically includes, but is not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, 2,3-dimethylbutyl, 2-ethylhexyl, n-heptyl, n-octyl, n-nonyl, 3,7-dimethyloctyl, n-decyl, n-undecyl, n-dodecyl, n-tridecyl, and 2-propylheptyl. Unless stated otherwise, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. The double bond of an alkenyl group can be unconjugated or conjugated to another unsaturated group. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_1$ and $C_{12}$ alkenyls. Exemplary alkenyl groups include, but are not limited to, ethenyl, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, butadienyl, pentadienyl, hexadienyl, 2-ethylhexenyl, 2-propyl-2-butenyl, 4-(2-methyl-3-ethenyl)-pentenyl. Unless stated otherwise specifically in the specification, an alkenyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. The triple bond of an alkynyl group can be unconjugated or conjugated to another unsaturated group. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of alkynyl group include 1-propynyl, 2-propynyl (i.e., propargyl), 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, 2-ethylhexynyl, 4-(2-methyl-3-ethynyl)-pentynyl, and the like. Unless stated otherwise specifically in the specification, an alkynyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alkynyl radical as defined above containing one to twelve carbon atoms. Unless stated otherwise specifically in the specification, an alkoxy group can be optionally substituted.

"Aryl" refers to a substituent that is derived from an aromatic hydrocarbon (arene) that has had a hydrogen atom removed from a ring carbon atom. Non-limiting examples of aryl includes phenyl, biphenyl, naphthyl, anthracenyl, and the like. Unless stated otherwise specifically in the specification, the term "aryl" is meant to include aryl radicals that are optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include cycloalkyl, cycloalkenyl and cycloalkynyl as defined herein. Unless stated otherwise specifically in the specification, a carbocyclyl group can be optionally substituted.

"Cycloalkyl" refers to cyclized alkyl groups having from three to twenty carbon atoms, e.g., having from three to nine carbon atoms, which can include fused, bridged, or spiro ring systems. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused, bridged, or spiro ring systems, having from three to twenty carbon atoms, e.g., having from three to nine carbon atoms, and which is attached to the rest of the molecule by a single bond. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Heterocyclyl" "heterocyclic ring" or "heterocycle" refers to a stable 3- to 20-membered non-aromatic, saturated or partially unsaturated ring radical which consists of two to twelve carbon ring atoms and from one to six heteroatoms as ring atoms selected from nitrogen, oxygen or sulfur, at least one non-aromatic, saturated or partially unsaturated ring containing at least one heteroatom as a ring atom. Unless stated otherwise specifically in the specification, the heterocyclyl radical can be a monocyclic, bicyclic, tricyclic or tetracyclic ring system, which can include fused, bridged, or spiro ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In embodiments where "L" is heterocyclyl, the heterocyclyl radical is a diradical. Unless stated otherwise specifically in the specification, a heterocyclyl group can be optionally substituted.

"Heterocyclyl" or "heterocyclic" or "heterocycle" as used by itself or as part of another group refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is on the heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like. Unless otherwise stated specifically in the specification, a heterocyclyl can be optionally substituted.

"Heteroaryl" refers to a 5- to 20-membered ring system radical comprising one to thirteen carbon ring atoms, one to six heteroatoms as ring atoms selected from nitrogen, oxygen and sulfur, and at least one aromatic ring containing at least one heteroatom as a ring atom. For purposes of this disclosure, the heteroaryl radical can be a monocyclic, bicyclic, tricyclic or tetracyclic ring system, which can include fused, bridged, or spiro ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophene), benzotriazolyl, benzo[4,6]imidazo[1,2-a]pyridinyl, carbazolyl, cinnolinyl, dibenzofuranyl, dibenzothiophene, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophene (i.e. thienyl). In embodiments where "X" is heteroarylene, X is a heteroaryl diradical. Unless stated otherwise specifically in the specification, a heteroaryl group can be optionally substituted.

"Leaving group" refers to a functional group that can be substituted by another functional group during a chemical reaction. Exemplary leaving groups can be found in e.g.,

*Organic Chemistry*, Francis Carey, 2nd edition, pages 328-331, McGraw-Hill Book Company, 1992, incorporated by reference herein. Non-limiting examples of leaving group include

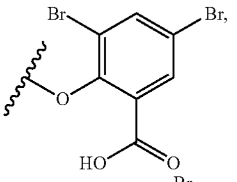

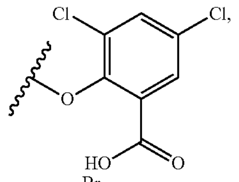

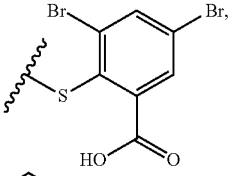

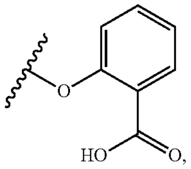

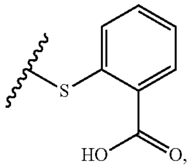

halogens (e.g., Cl, Br, I), hydroxy, phosphate, methanesulfonyl (mesyl, Ms), p-toluenesulfonyl (tosyl, Ts), fluoromethanesulfonyl, difluoromethanesulfonyl, trifluoromethylsulfonyl (triflate, Tf), ethanesulfonyl, para-nitrophenol, and diazonium group.

The term "substituted" used herein means any of the above groups (i.e., alkyl, alkylene, alkenyl, alkenylene, alkynyl, alkynylene, alkoxy, alkylamino, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups.

"Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further includes any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

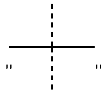

or

hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

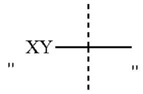

or

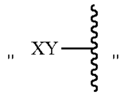

indicates that the chemical entity "XY" is bonded to another chemical entity via the point of attachment bond. Furthermore, the specific point of attachment to the non-depicted chemical entity can be specified by inference.

The term "salt" includes both acid and base addition salts. Salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

As used herein, the term "stereoisomer" refers to isomeric molecules that have the same molecular formula and sequence of bonded atoms (i.e., constitution), but differ in the three-dimensional orientations of their atoms in space. This contrasts with structural isomers, which share the same molecular formula, but the bond connection of their order differs. Molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

The present disclosure is intended to encompass deuterated forms of the compounds described herein, which include isotopes of atoms occurring in the compounds. Isotopes include those atoms having the same atomic number but different mass numbers. By way of general example, and without limitation, isotopes of hydrogen include deuterium and tritium, and isotopes of carbon include $^{13}C$ and $^{14}C$. Isotopically labeled compounds of the present disclosure can generally be prepared by conventional techniques known to those skilled in the art or by processes and methods analogous to those described herein, using an appropriate isotopically labeled reagent in place of the non-labeled reagent otherwise employed.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Compounds

In one aspect of the present disclosure, a multifunctional linker compound is provided, and the linker compound is a compound of formula (I), (I-1), (I-2), (I-3), or (I-4), or Table A, or a salt, a stereoisomer, or a deuterated form thereof. These linker compounds can be used for conjugation with proteins including Hemoglobin protein (Hb), as well as amino acids and peptides, thereby providing crosslinked structures with enhanced stability. For example, a conjugation may be obtained by crosslinking two or more lysine residues (e.g., two, three lysine residues) of the hemoglobin with the compound of the present disclosure, or a salt, stereoisomer, or deuterated form thereof.

Compounds of Formula (I)

In embodiments, the present disclosure provides a compound of formula (I):

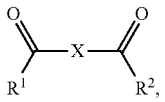

(I)

or a salt, a stereoisomer, or a deuterated form thereof, wherein:

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, arylene, heteroarylene, or $-L^1-NR^A-L^2-$, wherein X is optionally substituted with 1-6 $R^3$ as permitted by valency;

$R^1$ and $R^2$ are each independently —OH, halogen, or a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

$R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-$(OCH_2CH_2)_m$—$(CH_2)_n$—$N_3$, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

$R^1$ and $R^2$

In some embodiments of the compounds of formula (I), or a salt, stereoisomer, or deuterated form thereof, $R^1$ and $R^2$ are each independently —OH, halogen, or a leaving group. In some embodiments, $R^1$ and $R^2$ are each independently halogen (e.g., —F, —Cl, —Br, —I), or a leaving group. In some embodiments, $R^1$ and $R^2$ are each independently a leaving group. In some embodiments, $R^1$ and $R^2$ are the same. In some embodiments, $R^1$ and $R^2$ are different.

In some embodiments of the compounds of formula (I), or a salt, stereoisomer, or deuterated form thereof, $R^1$ and $R^2$ are each independently a leaving group, which is

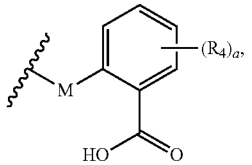

wherein M is O or S, each $R^4$ is independently halogen or —$C_{1-6}$ alkyl, and a is an integer of 0-4. In some embodiments, M is O, and a is 0, and the leaving group is

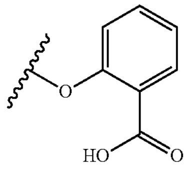 [SMILES: *Oc1ccccc1C(=O)O]

In some embodiments, M is S, and a is 0, and the leaving group is

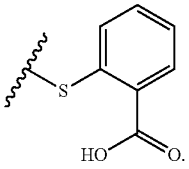 [SMILES: *Sc1ccccc1C(=O)O]

In some embodiments, a is 1, 2, or 3. In some embodiments, each $R^4$ is halogen (—F, —Cl, —Br, —I). In some embodiments, each $R^4$ is independently —F, —Cl, or —Br. In some embodiments, a is 2 and each $R^4$ is —Br, and the leaving group is

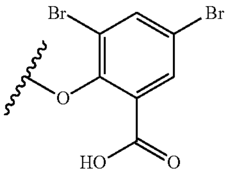

or

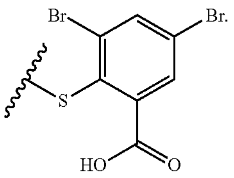

In some embodiments, a is 2 and each $R^4$ is —Cl, and the leaving group is

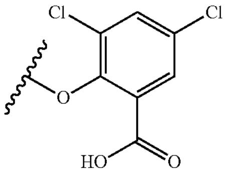

or

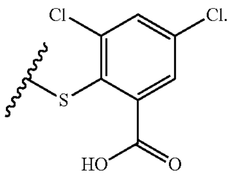

In some embodiments, a is 1, and $R^4$ is —Br, and the leaving group is

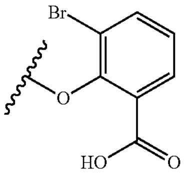

,

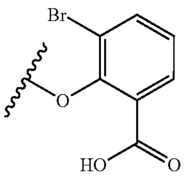

,

-continued

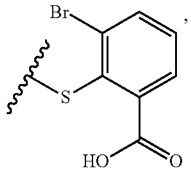

, or

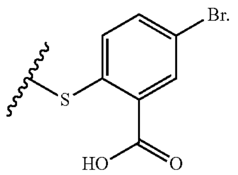

In some embodiments of the compounds of formula (I), or a salt, stereoisomer, or deuterated form thereof, $R^1$ and $R^2$ are

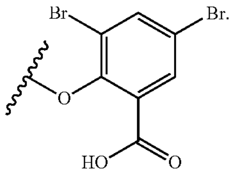 [SMILES: *Oc1c(Br)cc(Br)cc1C(=O)O]

In some embodiments of the compounds of formula (I), or a salt, stereoisomer, or deuterated form thereof, $R^1$ and $R^2$ are

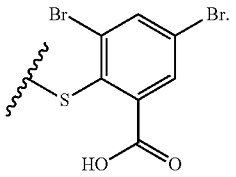 [SMILES: *Sc1c(Br)cc(Br)cc1C(=O)O]

In some embodiments of the compounds of formula (I), or a salt, stereoisomer, or deuterated form thereof, $R^1$ and $R^2$ are

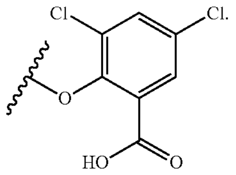

In some embodiments of the compounds of formula (I), or a salt, stereoisomer, or deuterated form thereof, $R^1$ and $R^2$ are

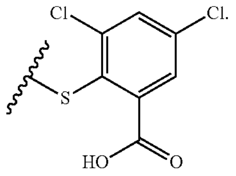

In some embodiments of the compounds of formula (I), or a salt, stereoisomer, or deuterated form thereof, $R^1$ and $R^2$ are

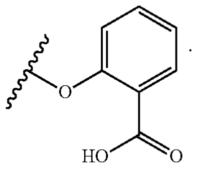 [SMILES: *Oc1ccccc1C(=O)O]

In some embodiments of the compounds of formula (I), or a salt, stereoisomer, or deuterated form thereof, $R^1$ and $R^2$ are

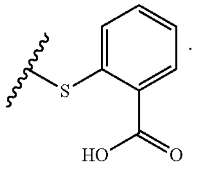 [SMILES: *Sc1ccccc1C(=O)O]

In some embodiments of the compounds of formula (I), or a salt, stereoisomer, or deuterated form thereof, $R^1$ and $R^2$ are each independently a leaving group, which is —O—($C_{1-6}$ alkylene)-$SO_3H$. In some embodiments, $R^1$ and $R^2$ are each independently a leaving group selected from the group consisting of —O—($CH_2$)—$SO_3H$, —O—($CH_2CH_2$)—$SO_3H$, —O—($CH_2CH_2CH_2$)—$SO_3H$, and —O—($CH_2CH_2CH_2CH_2$)—$SO_3H$. In some embodiments, the leaving group is —O—($CH_2CH_2$)—$SO_3H$. In some embodiments of the compounds of formula (I), or a salt, stereoisomer, or deuterated form thereof, $R^1$ and $R^2$ are —O—($CH_2CH_2$)—$SO_3H$.

X

In some embodiments of the compounds of formula (I), or a salt, stereoisomer, or deuterated form thereof, X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, arylene, heteroarylene, or -$L^1$-$NR^A$-$L^2$-, wherein X is optionally substituted; $R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-$(OCH_2CH_2)_m$—$(CH_2)_n$—$N_3$, wherein each alkyl, aryl, or alkylene is optionally and independently substituted; and $L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted.

In some embodiments, X is optionally substituted with 1-6 $R^3$ as permitted by valency, wherein each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen. In some embodiments, $R^1$ is —OH, halogen, or a leaving group. In some embodiments, each m is independently an integer in a range of 1-200, 2-175, 3-150, 4-125, 5-100, 6-75, 7-50, 8-45, 9-40, 10-35, 11-30, 12-25, 13-22, 14-20, 15-18, or 16-17. In some embodiments, each n is independently an integer in a range of 0-50, 1-40, 2-35, 3-30, 4-25, 5-20, 6-18, 7-16, 8-14, 9-12, or 10-11.

In some embodiments, X is -$L^1$-$NR^A$-$L^2$-. In some embodiments, each alkyl, aryl, or alkylene of $R^A$ is optionally and independently substituted with —$C_{1-6}$ alkyl, —OH, —CN, —$NO_2$, or halogen. In some embodiments, $L^1$ and $L^2$ are optionally and independently substituted with 1-3 $R^3$ as permitted by valency, wherein each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen. In some embodiments, $R^1$ is —OH, halogen, or a leaving group. In some embodiments, each m is independently an integer in a range of 1-200, 2-175, 3-150, 4-125, 5-100, 6-75, 7-50, 8-45, 9-40, 10-35, 11-30, 12-25, 13-22, 14-20, 15-18, or 16-17. In some embodiments, each n is independently an integer in a range of 0-100, 1-50, 2-40, 2-35, 3-30, 4-25, 5-20, 6-18, 7-16, 8-14, 9-12, or 10-11.

(i) Alkylene, Alkenylene, or Alkynylene as X

In some embodiments of the compounds of formula (I), or a salt, stereoisomer, or deuterated form thereof, X is $C_{1-12}$ alkylene, $C_{2-12}$ alkenylene, or $C_{2-12}$ alkynylene, each of which is optionally substituted with 1-6 $R^3$ as permitted by valency. In some embodiments, each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen.

In some embodiments, X is $C_{1-12}$ alkylene, $C_{2-11}$ alkylene, $C_{3-10}$ alkylene, $C_{4-9}$ alkylene, $C_{5-8}$ alkylene, or $C_{6-7}$ alkylene, each of which is optionally substituted with 1-6, 2-5, or 3-4 $R^3$ as permitted by valency. In some embodiments, X is $C_{2-12}$ alkenylene, $C_{3-11}$ alkenylene, $C_{4-10}$ alkenylene, $C_{5-9}$ alkenylene, $C_{6-8}$ alkenylene, or $C_7$ alkenylene, each of which is optionally substituted with 1-6, 2-5, or 3-4 $R^3$ as permitted by valency. In some embodiments, X is $C_{2-12}$ alkynylene, $C_{3-11}$ alkynylene, $C_{4-10}$ alkynylene, $C_{5-9}$ alkynylene, $C_{6-8}$ alkynylene, or $C_7$ alkynylene, each of which is optionally substituted with 1-6, 2-5, or 3-4 $R^3$ as permitted by valency. In some embodiments, X is unsubstituted $C_{1-12}$ alkylene, $C_{2-12}$ alkenylene, or $C_{2-12}$ alkynylene. In some embodiments, X is straight (i.e., unbranched) $C_{1-12}$ alkylene, $C_{2-12}$ alkenylene, or $C_{2-12}$ alkynylene.

In some embodiments of the compounds of formula (I), or a salt, stereoisomer, or deuterated form thereof, X is $C_{1-6}$ alkylene, $C_{2-6}$ alkenylene, or $C_{2-6}$ alkynylene, each of which is optionally substituted with 1 or 2 $R^3$ as permitted by valency. In some embodiments, X is unsubstituted $C_{1-6}$ alkylene, $C_{2-6}$ alkenylene, or $C_{2-6}$ alkynylene. In some embodiments, X is straight $C_{1-6}$ alkylene, $C_{2-6}$ alkenylene, or $C_{2-6}$ alkynylene.

In some embodiments of the compounds of formula (I), or a salt, stereoisomer, or deuterated form thereof, X is $C_{1-6}$ alkylene optionally substituted with 1 or 2 $R^3$ as permitted by valency. In some embodiments, X is unsubstituted $C_{1-6}$ alkylene. In some embodiments, X is straight $C_{1-6}$ alkylene. In some embodiments, X is

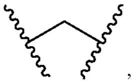, 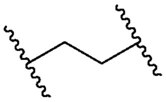, 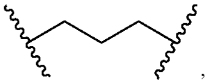,

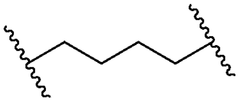,

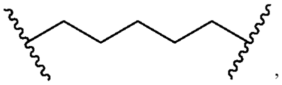, or

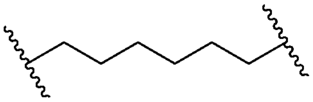.

In some embodiments of the compounds of formula (I), or a salt, stereoisomer, or deuterated form thereof, X is $C_{2-6}$ alkenylene optionally substituted with 1 or 2 $R^3$ as permitted by valency. In some embodiments, X is unsubstituted $C_{2-6}$ alkenylene. In some embodiments, X is straight $C_{2-6}$ alkenylene. In some embodiments, X is

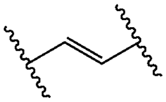 or 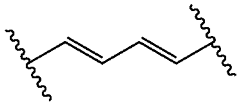.

In some embodiments of the compounds of formula (I), or a salt, stereoisomer, or deuterated form thereof, X is $C_{2-6}$ alkynylene optionally substituted with 1 or 2 $R^3$ as permitted by valency. In some embodiments, X is unsubstituted $C_{2-6}$ alkynylene. In some embodiments, X is straight $C_{2-6}$ alkynylene. In some embodiments, X is

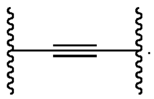.

In some embodiments of the compounds of formula (I), or a salt, stereoisomer, or deuterated form thereof, X is $C_{1-6}$ alkylene, $C_{2-6}$ alkenylene, or $C_{2-6}$ alkynylene, each of which is substituted with —S—($C_{1-6}$ alkylene)-$(OCH_2CH_2)_m$—$(CH_2)_n$—$N_3$, or —O—($C_{1-6}$ alkylene)-$(OCH_2CH_2)_m$—$(CH_2)_n$—$N_3$, and wherein each m is independently an integer of 1-50, 2-40, 3-30, 4-25, 5-20, 6-18, 7-16, 8-14, 9-12, or 10-11, and each n is independently an integer of 0-25, 1-20, 2-15, 3-10, 4-8, or 5-7. In some embodiments, X is $C_{1-6}$ alkylene substituted with —S—($C_{1-6}$ alkylene)-$(OCH_2CH_2)_m$—$(CH_2)_n$—$N_3$, and wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In some embodiments, X is

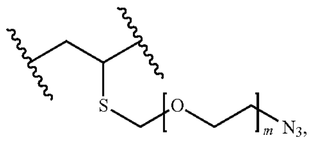

and wherein m is an integer of 1-25, 2-20, 3-15, 4-10, or 5-8. In some embodiments, m is 3-8, 4-7, or 5-6. In some embodiments, X is

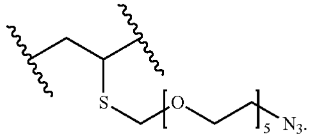

(ii) Cycloalkylene, Cycloalkenylene, or Heterocyclylene as X

In some embodiments of the compounds of formula (I), or a salt, stereoisomer, or deuterated form thereof, X is $C_{3-9}$ cycloalkylene, $C_{3-9}$ cycloalkenylene, or 5-12 membered heterocyclylene, each of which is optionally substituted with 1 or 2 $R^3$ as permitted by valency. In some embodiments, each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen. In some embodiments, X is unsubstituted $C_{3-9}$ cycloalkylene, $C_{3-9}$ cycloalkenylene, or 5-12 membered heterocyclylene.

In some embodiments, X is $C_{3-9}$ cycloalkylene, $C_{4-8}$ cycloalkylene, $C_{5-7}$ cycloalkylene, or $C_6$ cycloalkylene, each of which is optionally substituted with 1 or 2 $R^3$ as permitted by valency. In some embodiments, X is $C_{3-9}$ cycloalkenylene, $C_{4-8}$ cycloalkenylene, $C_{5-7}$ cycloalkenylene, or $C_6$ cycloalkenylene, each of which is optionally substituted with 1 or 2 $R^3$ as permitted by valency. In some embodiments, X is 5-12 membered, 6-11 membered, 7-10 membered, or 8-9 membered heterocyclylene containing a heteroatom which is S, O, or N, each of which is optionally substituted with 1 or 2 $R^3$ as permitted by valency.

In some embodiments of the compounds of formula (I), or a salt, stereoisomer, or deuterated form thereof, X is $C_{3-7}$ cycloalkylene or $C_{4-6}$ cycloalkylene optionally substituted with 1 or 2 $R^3$ as permitted by valency. In some embodiments, X is unsubstituted $C_{3-7}$ cycloalkylene or $C_{4-6}$ cycloalkylene. In some embodiments, X is

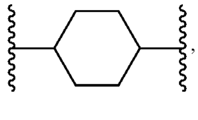, 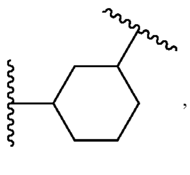, or

-continued

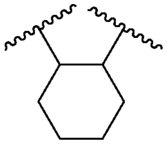.

In some embodiments of the compounds of formula (I), or a salt, stereoisomer, or deuterated form thereof, X is $C_{3-7}$ cycloalkenylene or $C_{4-6}$ cycloalkenylene optionally substituted with 1 or 2 $R^3$ as permitted by valency. In some embodiments, X is unsubstituted $C_{3-7}$cycloalkenylene or $C_{4-6}$ cycloalkenylene. In some embodiments, X is

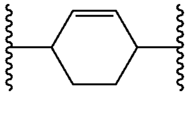, 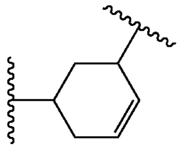,

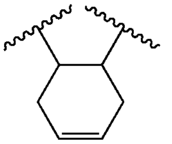, 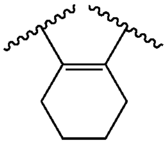, or

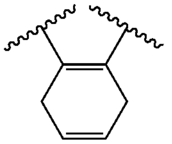.

In some embodiments of the compounds of formula (I), or a salt, stereoisomer, or deuterated form thereof, X is $C_{3-7}$ cycloalkenylene or $C_{4-6}$ cycloalkenylene substituted with —($C_{1-12}$ alkylene)-$N_3$, —($C_{1-9}$ alkylene)-$N_3$, —($C_{1-6}$ alkylene)-$N_3$, —($C_{2-5}$ alkylene)-$N_3$, or —($C_{3-4}$ alkylene)-$N_3$. In some embodiments, X is

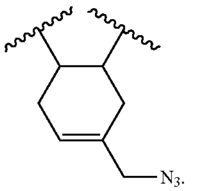 [SMILES: *C1CC=C(CN=[N+]=[N-])CC1*]

In some embodiments of the compounds of formula (I), or a salt, stereoisomer, or deuterated form thereof, X is a 5-12 membered, 6-11 membered, 7-10 membered, or 8-9 membered heterocyclylene containing a heteroatom which is S or O, and wherein the heterocyclylene is optionally substituted. In some embodiments, the heterocyclylene is optionally substituted with —($C_{1-6}$ alkylene)-$N_3$. In some embodiments, X is a 6-10 membered, or 7-9 membered heterocyclylene containing O, and wherein the heterocyclylene is substituted with —($C_{1-6}$ alkylene)-$N_3$. In some embodiments, X is

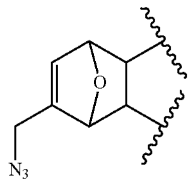.

(iii) Arylene or Heteroarylene as X

In some embodiments of the compounds of formula (I), or a salt, stereoisomer, or deuterated form thereof, X is arylene or heteroarylene, each of which is optionally substituted with 1 or 2 $R^3$ as permitted by valency.

In some embodiments of the compounds of formula (I), or a salt, stereoisomer, or deuterated form thereof, X is $C_{6-10}$ arylene that is optionally substituted. In some embodiments, X is $C_{6-10}$ arylene that is optionally substituted with 1 or 2 $R^3$ as permitted by valency.

In embodiments, X is unsubstituted $C_{6-10}$ arylene. In some embodiments, X is

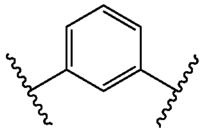 or 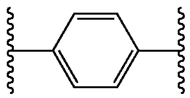

In embodiments, X is substituted $C_{6-10}$ arylene.

In embodiments, X is $C_{6-10}$ arylene substituted with —C(O)—$R^1$, and wherein $R^1$ is —OH, halogen, or a leaving group. In some embodiments, $R^1$ is a leaving group. In some embodiments, $R^1$ is a leaving group which is

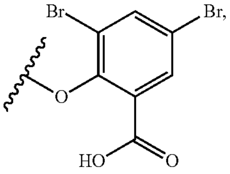 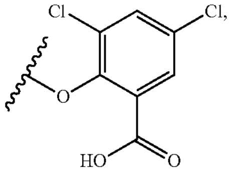

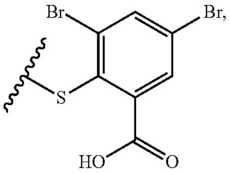 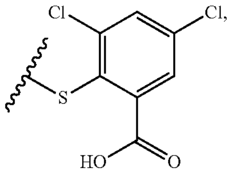

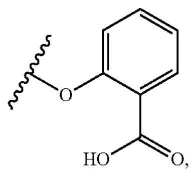 or 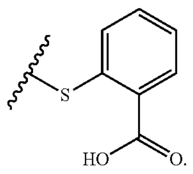

In some embodiments, X is

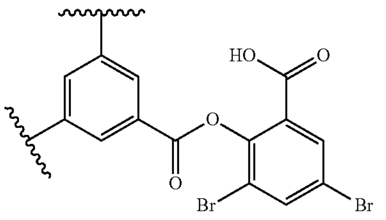

or

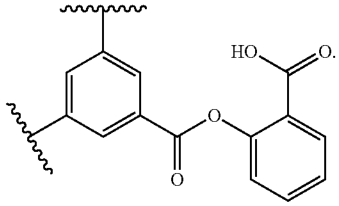

In embodiments, X is $C_{6-10}$ arylene substituted with —C(O)NH—($C_{1-12}$ alkylene)-$(OCH_2CH_2)_m$—$(CH_2)_n$—$N_3$, or —NHC(O)—($C_{1-12}$ alkylene)-$(OCH_2CH_2)_m$—$(CH_2)_n$—$N_3$, and wherein each m is independently an integer of 1-200, 2-175, 3-150, 4-125, 5-100, 6-75, 7-50, 8-45, 9-40, 10-35, 11-30, 12-25, 13-22, 14-20, 15-18, or 16-17, and each n is independently an integer of 0-100, 1-50, 2-40, 3-30, 4-25, 5-20, 6-18, 7-16, 8-14, 9-12, or 10-11.

In embodiments, X is $C_{6-10}$ arylene substituted with —C(O)NH—($C_{1-6}$ alkylene)-$(OCH_2CH_2)_m$—$N_3$, and wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, X is

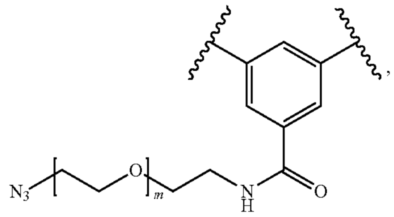

and wherein m is an integer of 2-50, 3-25, or 4-10. In embodiments, X is

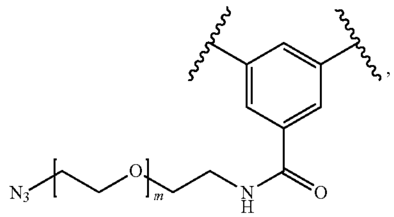

and wherein m is 4. In embodiments, X is

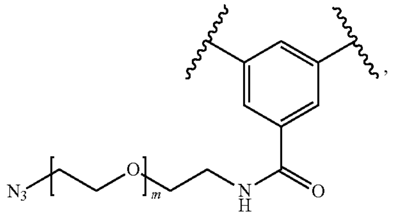

and wherein m is 9.

In embodiments, X is $C_{6-10}$ arylene substituted with —NHC(O)—($C_{1-6}$ alkylene)-$(OCH_2CH_2)_m$—$N_3$, and wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, X is

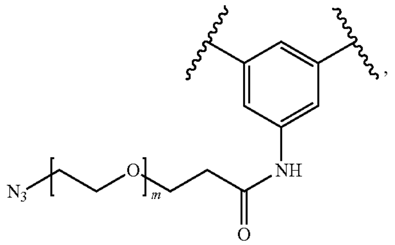

and wherein m is an integer of 2-50, 3-25, or 4-10. In embodiments, X is

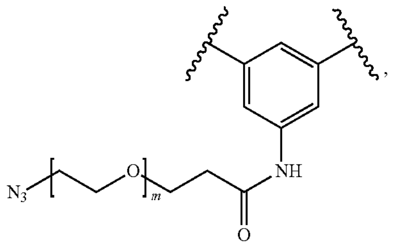

and wherein m is 4. In embodiments, X is

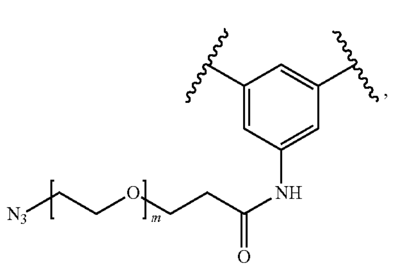

and wherein m is 9.

(iv) -$L^1$-$NR^A$-$L^2$- as X

In some embodiments of the compounds of formula (I), or a salt, stereoisomer, or deuterated form thereof, X is -$L^1$-$NR^A$-$L^2$-, and wherein: $R^A$ is H, —$C_{1-6}$ alkyl, aryl, —C(O)-aryl, —$SO_2$($C_{1-6}$ alkyl), —$SO_2$-aryl, or —($C_{1-12}$ alkylene)-$(OCH_2CH_2)_m$—$(CH_2)_n$—$N_3$, wherein m is an integer of 1-50, 2-40, 3-30, 4-25, 5-20, 6-18, 7-16, 8-14, 9-12, or 10-11, n is an integer of 0-25, 1-20, 2-15, 3-10, 4-8, or 5-7, and each alkyl, aryl, or alkylene is optionally and independently substituted; and $L^1$ and $L^2$ are each independently $C_{1-6}$ alkylene, $C_{2-6}$ alkenylene, $C_{2-6}$ alkynylene, $C_{3-6}$ cycloalkylene, $C_{3-6}$ cycloalkenylene, arylene, or heteroarylene, wherein $L^1$ and $L^2$ are optionally and independently substituted. In embodiments, each alkyl, aryl, or alkylene of $R^A$ is optionally and independently substituted with —$C_{1-6}$ alkyl. In embodiments, $L^1$ and $L^2$ are optionally and independently substituted with 1-3 $R^3$. In some embodiments, each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen.

In embodiments, $L^1$ and $L^2$ are the same. In embodiments, $L^1$ and $L^2$ are different.

In embodiments, $R^A$ is H. In embodiments, $L^1$ and $L^2$ are each independently $C_{1-6}$ alkylene or $C_{2-6}$ alkenylene. In embodiments, $R^A$ is H, and $L^1$ and $L^2$ are each independently $C_{1-6}$ alkylene or $C_{2-6}$ alkenylene. In embodiments, $L^1$ and $L^2$ are $C_{1-6}$ alkylene, $C_{2-5}$ alkylene, or $C_{3-4}$ alkylene. In embodiments, $L^1$ and $L^2$ are —$CH_2$—. In embodiments, X is

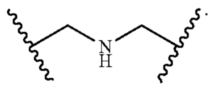

In embodiments, $R^A$ is $C_{6-10}$ aryl, and wherein the aryl of $R^A$ is optionally substituted. In embodiments, the aryl of $R^A$ is optionally substituted with —$C_{1-6}$ alkyl. In embodiments, $L^1$ and $L^2$ are each independently $C_{1-6}$ alkylene, or $C_{2-6}$ alkenylene. In embodiments, $R^A$ is $C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl. In embodiments, $R^A$ is phenyl. In embodiments, $L^1$ and $L^2$ are $C_{1-6}$ alkylene, $C_{2-5}$ alkylene, or $C_{3-4}$ alkylene. In embodiments, $L^1$ and $L^2$ are —$CH_2$—. In embodiments, X is

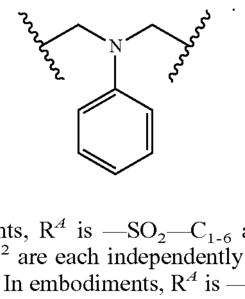

In embodiments, $R^A$ is —$SO_2$—$C_{1-6}$ alkyl. In embodiments, $L^1$ and $L^2$ are each independently $C_{1-6}$ alkylene, or $C_{2-6}$ alkenylene. In embodiments, $R^A$ is —$SO_2$—$C_{1-6}$ alkyl, and $L^1$ and $L^2$ are each independently $C_{1-6}$ alkylene, or $C_{2-6}$ alkenylene. In embodiments, $R^A$ is —$SO_2$—$CH_3$. In embodiments, $L^1$ and $L^2$ are $C_{1-6}$ alkylene, $C_{2-5}$ alkylene, or $C_{3-4}$ alkylene. In embodiments, $L^1$ and $L^2$ are —$CH_2$—. In embodiments, X is

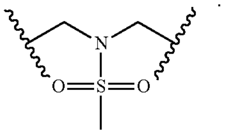 [SMILES: *CN(C*)S(C)(=O)=O]

In embodiments, $R^A$ is —$SO_2$—$C_{6-10}$ aryl, wherein the aryl of $R^A$ is optionally substituted. In embodiments, the aryl of $R^A$ is optionally substituted with —$C_{1-6}$ alkyl. In some embodiments, $L^1$ and $L^2$ are each independently $C_{1-6}$ alkylene, or $C_{2-6}$ alkenylene. In embodiments, $R^A$ is —$SO_2$—$C_{6-10}$ aryl, wherein the aryl of $R^A$ is optionally substituted with —$C_{1-6}$ alkyl, and $L^1$ and $L^2$ are each independently $C_{1-6}$ alkylene, or $C_{2-6}$ alkenylene. In embodiments, $R^A$ is

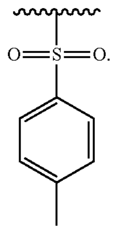

In embodiments, $L^1$ and $L^2$ are $C_{1-6}$ alkylene, $C_{2-s}$ alkylene, or $C_{3-4}$ alkylene. In embodiments, $L^1$ and $L^2$ are —$CH_2$—. In embodiments, X is

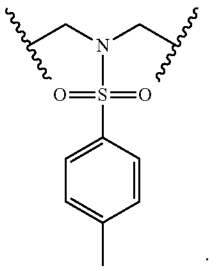 [SMILES: *CN(C*)S(=O)(=O)c1ccc(C)cc1]

In embodiments, $R^A$ is —C(O)—$C_{6-10}$ aryl, wherein the aryl of $R^A$ is optionally substituted. In some embodiments, the aryl of $R^A$ is optionally substituted with —$C_{1-6}$ alkyl. In embodiments, $L^1$ and $L^2$ are each independently $C_{1-6}$ alkylene, or $C_{2-6}$ alkenylene. In embodiments, $R^A$ is —C(O)—$C_{6-10}$ aryl, wherein the aryl of $R^A$ is optionally substituted with —$C_{1-6}$ alkyl, and $L^1$ and $L^2$ are each independently $C_{1-6}$ alkylene, or $C_{2-6}$ alkenylene. In embodiments, $R^A$ is

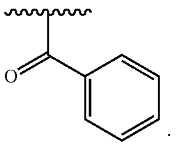 [SMILES: *C(=O)c1ccccc1]

In embodiments, $L^1$ and $L^2$ are $C_{1-6}$ alkylene, $C_{2-5}$ alkylene, or $C_{3-4}$ alkylene. In embodiments, $L^1$ and $L^2$ are —$CH_2$—. In embodiments, X is

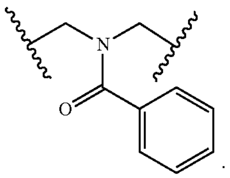 [SMILES: *CN(C*)C(=O)c1ccccc1]

In embodiments, $R^4$ is $-(C_{1-6}$ alkylene$)-(OCH_2CH_2)_m-(CH_2)_n-N_3$, wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, $L^1$ and $L^2$ are each independently $C_{1-6}$ alkylene, or $C_{2-6}$ alkenylene. In embodiments, $R^4$ is $-(C_{1-6}$ alkylene$)-(OCH_2CH_2)_m-(CH_2)_n-N_3$, and $L^1$ and $L^2$ are each independently $C_{1-6}$ alkylene, or $C_{2-6}$ alkenylene, wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, n is 0. In embodiments, $R^4$ is

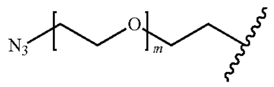

wherein m is 1-12, 2-6, or 3-5. In embodiments, $L^1$ and $L^2$ are $C_{1-6}$ alkylene, $C_{2-5}$ alkylene, or $C_{3-4}$ alkylene. In embodiments, $L^1$ and $L^2$ are $-CH_2-$. In embodiments, X is

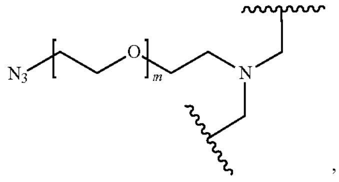

and m is 3.

Compounds of Formula (I-1)

In embodiments, the present disclosure provides a compound of formula (I-1):

(I-1)

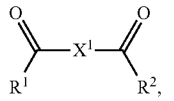

or a salt, a stereoisomer, or a deuterated form thereof, wherein:

$X^1$ is arylene or heteroarylene, wherein $X^1$ is optionally substituted with 1 or 2 $R^3$ as permitted by valency;

$R^1$ and $R^2$ are each independently a leaving group;

each $R^3$ is independently $-OH$, $-CN$, $-NO_2$, halogen, oxo, $-C_{1-6}$ alkyl, $-C_{1-6}$ haloalkyl, $-O(C_{1-6}$ alkyl), $-S(C_{1-6}$ alkyl), $-SO(C_{1-6}$ alkyl), $-SO_2(C_{1-6}$ alkyl), $-(C_{1-12}$ alkylene$)-N_3$, $-(C_{1-12}$ alkylene$)-(OCH_2CH_2)_m-(CH_2)_n-N_3$, $-C(O)NH-(C_{1-12}$ alkylene$)-(OCH_2CH_2)_m-(CH_2)_n-N_3$, $-NHC(O)-(C_{1-12}$ alkylene$)-(OCH_2CH_2)_m-(CH_2)_n-N_3$, $-O-(C_{1-12}$ alkylene$)-(OCH_2CH_2)_m-(CH_2)_n-N_3$, $-S-(C_{1-12}$ alkylene$)-(OCH_2CH_2)_m-(CH_2)_n-N_3$, or $-C(O)-R^1$, wherein each alkyl or alkylene is optionally and independently substituted with $-C_{1-6}$ alkyl, $-OH$, $-CN$, $-NO_2$, or halogen;

each m is independently an integer of 1-200; and each n is independently an integer of 0-50.

In embodiments of the compounds of formula (I-1), or a salt, stereoisomer, or deuterated form thereof, if $X^1$ is

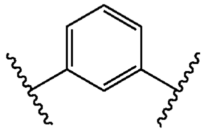

then the leaving group is not

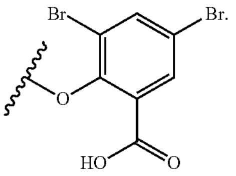

In embodiments of the compounds of formula (I-1), or a salt, stereoisomer, or deuterated form thereof, if $X^1$ is an arylene substituted with 1 $R^3$, then $R^3$ is different from $-C(O)-R^1$ or $-C(O)-R^2$.

In embodiments, the compound of formula (I-1), or a salt, or a stereoisomer thereof, comprises one or more $^{13}C$ isotopes of carbon atoms occurring in the compound.

In embodiments of the compounds of formula (I-1), or a salt, stereoisomer, or deuterated form thereof, $X^1$ is $C_{6-10}$ arylene that is optionally substituted. In some embodiments, $X^1$ is $C_{6-10}$ arylene that is optionally substituted with 1 or 2 $R^3$ as permitted by valency.

In embodiments, $X^1$ is unsubstituted $C_{6-10}$ arylene. In some embodiments, $X^1$ is

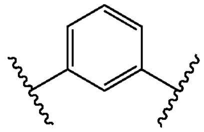

or

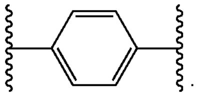

In embodiments, $X^1$ is substituted $C_{6-10}$ arylene. In embodiments, $X^1$ is $C_{6-10}$ arylene substituted with $-C(O)-R^1$, and wherein $R^1$ is $-OH$, halogen, or a leaving group. In some embodiments, $R^1$ is a leaving group. In some embodiments, $R^1$ is a leaving group which is

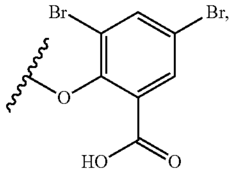

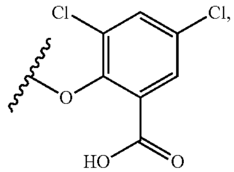

-continued

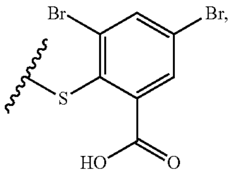
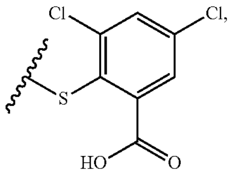
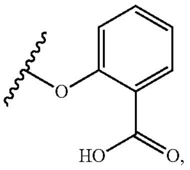
or
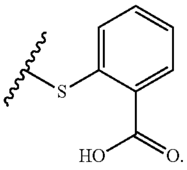

In some embodiments, $X^1$ is

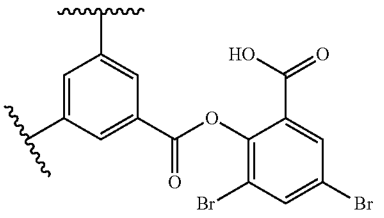
or
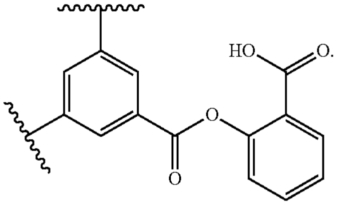

In embodiments, $X^1$ is $C_{6-10}$ arylene substituted with —C(O)NH—($C_{1-12}$ alkylene)-($OCH_2CH_2$)$_m$—($CH_2$)$_n$—$N_3$, or —NHC(O)—($C_{1-12}$ alkylene)-($OCH_2CH_2$)$_m$—($CH_2$)$_n$—$N_3$, and wherein each m is independently an integer of 1-200, and each n is independently an integer of 0-100. In embodiments, each m is independently an integer of 1-200, 2-175, 3-150, 4-125, 5-100, 6-75, 7-50, 8-45, 9-40, 10-35, 11-30, 12-25, 13-22, 14-20, 15-18, or 16-17. In embodiments, each n is independently an integer of 0-100, 1-50, 2-40, 3-30, 4-25, 5-20, 6-18, 7-16, 8-14, 9-12, or 10-11.

In embodiments, $X^1$ is $C_{6-10}$ arylene substituted with —C(O)NH—($C_{1-6}$ alkylene)-($OCH_2CH_2$)$_m$—$N_3$, and wherein m is an integer of 1-50. In embodiments, m is an integer of 1-50, 2-50, 2-40, 3-30, 4-25, 5-20, 6-18, 7-16, 8-14, 9-12, or 10-11. In embodiments, $X^1$ is

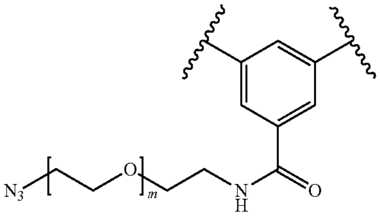
, and wherein m is an integer of 2-50, 3-25, or 4-10. In embodiments, $X^1$ is

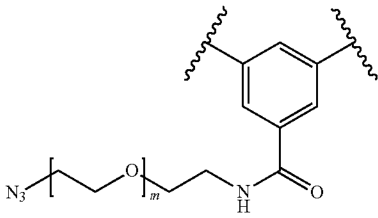
, and wherein m is 4. In embodiments, $X^1$ is

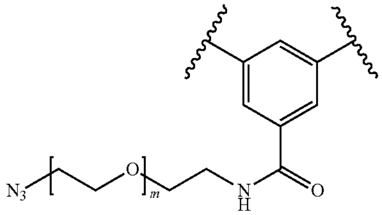
, and wherein m is 9.

In embodiments, $X^1$ is $C_{6-10}$ arylene substituted with —NHC(O)—($C_{1-6}$ alkylene)-($OCH_2CH_2$)$_m$—$N_3$, and wherein m is an integer of 1-50. In embodiments, m is an integer of 1-50, 2-40, 3-30, 4-25, 5-20, 6-18, 7-16, 8-14, 9-12, or 10-11. In embodiments, $X^1$ is

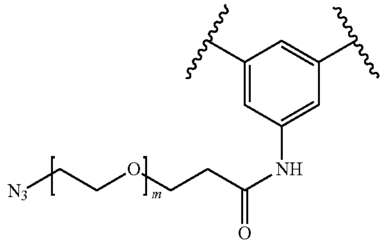
, and wherein m is an integer of 2-50, 3-25, or 4-10. In embodiments, $X^1$ is

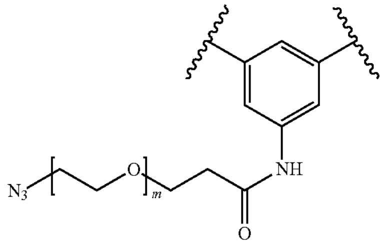
, and wherein m is 4. In embodiments, $X^1$ is

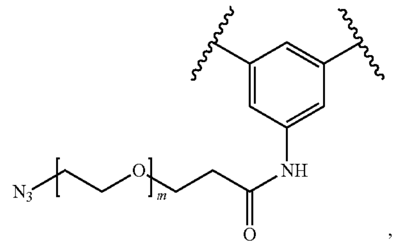
, and wherein m is 9.

Compounds of Formula (I-2)

In embodiments, the present disclosure provides a compound of formula (I-2):

(I-2)

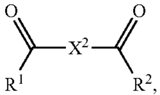
, or a salt, a stereoisomer, or a deuterated form thereof, wherein:

$X^2$ is $-L^1-NR^A-L^2-$, $R^1$ and $R^2$ are each independently a leaving group;

$R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-($OCH_2CH_2$)$_m$—($CH_2$)$_n$—$N_3$, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein L and $L^2$ are optionally and independently substituted with 1-3 $R^3$ as permitted by valency;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-12}$ alkylene)-$N_3$, —($C_{1-12}$ alkylene)-($OCH_2CH_2$)$_m$—($CH_2$)$_n$—$N_3$, —C(O)NH—($C_{1-12}$ alkylene)-($OCH_2CH_2$)$_m$—($CH_2$)$_n$—$N_3$, —NHC(O)—($C_{1-12}$ alkylene)-($OCH_2CH_2$)$_m$—($CH_2$)$_n$—$N_3$, —O—($C_{1-12}$ alkylene)-($OCH_2CH_2$)$_m$—($CH_2$)$_n$—$N_3$, —S—($C_{1-12}$ alkylene)-($OCH_2CH_2$)$_m$—($CH_2$)$_n$—$N_3$, or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

In embodiments, the compound of formula (I-2), or a salt, or a stereoisomer thereof, comprises one or more $^{13}C$ isotopes of carbon atoms occurring in the compound.

In embodiments of the compounds of formula (I-2), or a salt, a stereoisomer, or a deuterated form thereof, $R^A$ is H, —$C_{1-6}$ alkyl, aryl, —C(O)-aryl, —$SO_2$($C_{1-6}$ alkyl), —$SO_2$-aryl, or —($C_{1-12}$ alkylene)-($OCH_2CH_2$)$_m$—($CH_2$)$_n$—$N_3$, wherein m is an integer of 1-50, n is an integer of 0-25, and each alkyl, aryl, or alkylene is optionally and independently substituted with —$C_{1-6}$ alkyl; and $L^1$ and $L^2$ are each independently $C_{1-6}$ alkylene, $C_{2-6}$ alkenylene, $C_{2-6}$ alkynylene, $C_{3-6}$ cycloalkylene, $C_{3-6}$ cycloalkenylene, arylene, or heteroarylene, wherein $L^1$ and $L^2$ are optionally and independently substituted with 1-3 $R^3$.

In some embodiments of the compounds of formula (I-2), or a salt, stereoisomer, or deuterated form thereof, $X^2$ is $-L^1-NR^A-L^2-$, and wherein: $R^A$ is H, —$C_{1-6}$ alkyl, aryl, —C(O)-aryl, —$SO_2$($C_{1-6}$ alkyl), —$SO_2$-aryl, or —($C_{1-12}$ alkylene)-($OCH_2CH_2$)$_m$—($CH_2$)$_n$—$N_3$, wherein m is an integer of 1-50, 2-40, 3-30, 4-25, 5-20, 6-18, 7-16, 8-14, 9-12, or 10-11, n is an integer of 0-25, 1-20, 2-15, 3-10, 4-8, or 5-7, and each alkyl, aryl, or alkylene is optionally and independently substituted; and $L^1$ and $L^2$ are each independently $C_{1-6}$ alkylene, $C_{2-6}$ alkenylene, $C_{2-6}$ alkynylene, $C_{3-6}$ cycloalkylene, $C_{3-6}$ cycloalkenylene, arylene, or heteroarylene, wherein $L^1$ and $L^2$ are optionally and independently substituted. In embodiments, each alkyl, aryl, or alkylene of $R^A$ is optionally and independently substituted with —$C_{1-6}$ alkyl. In embodiments, $L^1$ and $L^2$ are optionally and independently substituted with 1-3 $R^3$. In some embodiments, each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-($OCH_2CH_2$)$_m$—($CH_2$)$_n$—$N_3$, —C(O)NH—($C_{1-12}$ alkylene)-($OCH_2CH_2$)$_m$—($CH_2$)$_n$—$N_3$, —NHC(O)—($C_{1-12}$ alkylene)-($OCH_2CH_2$)$_m$—($CH_2$)$_n$—$N_3$, —O—($C_{1-12}$ alkylene)-($OCH_2CH_2$)$_m$—($CH_2$)$_n$—$N_3$, —S—($C_{1-12}$ alkylene)-($OCH_2CH_2$)$_m$—($CH_2$)$_n$—$N_3$, or —C(O)—$R^1$, wherein each alkyl or alkylene is optionally and independently substituted with —$C_{1-6}$ alkyl, —OH, —CN, —$NO_2$, or halogen.

In embodiments, $L^1$ and $L^2$ are the same. In embodiments, $L^1$ and $L^2$ are different.

In embodiments, $R^A$ is H. In embodiments, $L^1$ and $L^2$ are each independently $C_{1-6}$ alkylene or $C_{2-6}$ alkenylene. In embodiments, $R^A$ is H, and $L^1$ and $L^2$ are each independently $C_{1-6}$ alkylene or $C_{2-6}$ alkenylene. In embodiments, $L^1$ and $L^2$ are $C_{1-6}$ alkylene, $C_{2-5}$ alkylene, or $C_{3-4}$ alkylene. In embodiments, $L^1$ and $L^2$ are —$CH_2$—. In embodiments, $X^2$ is

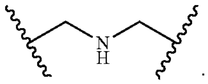 [SMILES: *CNC*]
.

In embodiments, $R^A$ is $C_{6-10}$ aryl, and wherein the aryl of $R^A$ is optionally substituted. In embodiments, the aryl of $R^A$ is optionally substituted with —$C_{1-6}$ alkyl. In embodiments, $L^1$ and $L^2$ are each independently $C_{1-6}$ alkylene, or $C_{2-6}$ alkenylene. In embodiments, $R^A$ is $C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl. In embodiments, $R^A$ is phenyl. In embodiments, $L^1$ and $L^2$ are $C_{1-6}$ alkylene, $C_{2-5}$ alkylene, or $C_{3-4}$ alkylene. In embodiments, $L^1$ and $L^2$ are —$CH_2$—. In embodiments, $X^2$ is

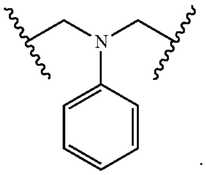 [SMILES: *CN(C*)c1ccccc1]
.

In embodiments, $R^A$ is —$SO_2$—$C_{1-6}$ alkyl. In embodiments, $L^1$ and $L^2$ are each independently $C_{1-6}$ alkylene, or $C_{2-6}$ alkenylene. In embodiments, $R^A$ is —$SO_2$—$C_{1-6}$ alkyl, and $L^1$ and $L^2$ are each independently $C_{1-6}$ alkylene, or $C_{2-6}$ alkenylene. In embodiments, $R^A$ is $—SO_2—CH_3$. In embodiments, $L^1$ and $L^2$ are $C_{1-6}$ alkylene, $C_{2-5}$ alkylene, or $C_{3-4}$ alkylene. In embodiments, $L^1$ and $L^2$ are $—CH_2—$. In embodiments, $X^2$ is

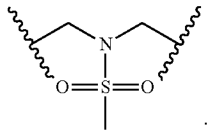 [SMILES: *CN(C*)S(C)(=O)=O]

In embodiments, $R^A$ is $—SO_2—C_{6-10}$ aryl, wherein the aryl of $R^A$ is optionally substituted. In embodiments, the aryl of $R^A$ is optionally substituted with $—C_{1-6}$ alkyl. In some embodiments, $L^1$ and $L^2$ are each independently $C_{1-6}$ alkylene, or $C_{2-6}$ alkenylene. In embodiments, $R^A$ is $—SO_2—C_{6-10}$ aryl, wherein the aryl of $R^A$ is optionally substituted with $—C_{1-6}$ alkyl, and $L^1$ and $L^2$ are each independently $C_{1-6}$ alkylene, or $C_{2-6}$ alkenylene. In embodiments, $R^A$ is

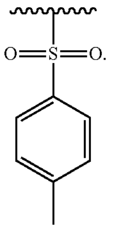 [SMILES: *S(=O)(=O)c1ccc(C)cc1]

In embodiments, $L^1$ and $L^2$ are $C_{1-6}$ alkylene, $C_{2-5}$ alkylene, or $C_{3-4}$ alkylene. In embodiments, $L^1$ and $L^2$ are $—CH_2—$. In embodiments, $X^2$ is

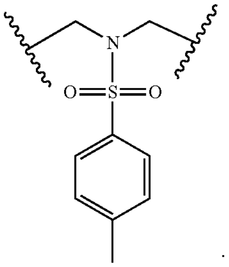 [SMILES: *CN(C*)S(=O)(=O)c1ccc(C)cc1]

In embodiments, $R^A$ is $—C(O)—C_{6-10}$ aryl, wherein the aryl of $R^A$ is optionally substituted. In some embodiments, the aryl of $R^A$ is optionally substituted with $—C_{1-6}$ alkyl. In embodiments, $L^1$ and $L^2$ are each independently $C_{1-6}$ alkylene, or $C_{2-6}$ alkenylene. In embodiments, $R^A$ is $—C(O)—C_{6-10}$ aryl, wherein the aryl of $R^A$ is optionally substituted with $—C_{1-6}$ alkyl, and $L^1$ and $L^2$ are each independently $C_{1-6}$ alkylene, or $C_{2-6}$alkenylene. In embodiments, $R^A$ is

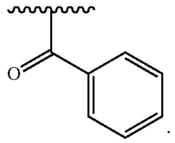 [SMILES: *C(=O)c1ccccc1]

In embodiments, $L^1$ and $L^2$ are $C_{1-6}$ alkylene, $C_{2-5}$ alkylene, or $C_{3-4}$ alkylene. In embodiments, $L^1$ and $L^2$ are $—CH_2—$. In embodiments, $X^2$ is

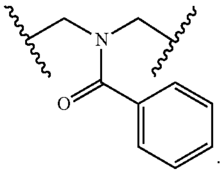 [SMILES: *CN(C*)C(=O)c1ccccc1]

In embodiments, $R^A$ is $—(C_{1-6}$ alkylene)-$(OCH_2CH_2)_m—(CH_2)_n—N_3$, wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, $L^1$ and $L^2$ are each independently $C_{1-6}$ alkylene, or $C_{2-6}$ alkenylene. In embodiments, $R^A$ is $—(C_{1-6}$ alkylene)-$(OCH_2CH_2)_m—(CH_2)_n—N_3$, and $L^1$ and $L^2$ are each independently $C_{1-6}$ alkylene, or $C_{2-6}$ alkenylene, wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, n is 0. In embodiments, $R^A$ is

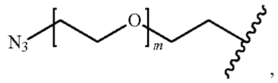

wherein m is 1-12, 2-6, or 3-5. In embodiments, $L^1$ and $L^2$ are $C_{1-6}$ alkylene, $C_{2-5}$ alkylene, or $C_{3-4}$ alkylene. In embodiments, $L^1$ and $L^2$ are $—CH_2—$. In embodiments, $X^2$ is

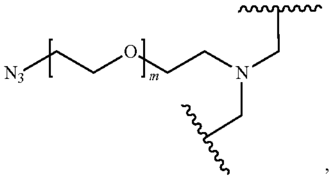

and m is 3.

Compounds of Formula (I-3)

In embodiments, the present disclosure provides a compound of formula (I-3):

(I-3)

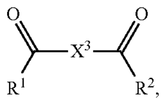

or a salt, a stereoisomer, or a deuterated form thereof, wherein:

$X^3$ is $C_{1-24}$ alkylene, $C_{2-24}$ alkenylene, or $C_{2-24}$ alkynylene, wherein $X^2$ is optionally substituted with 1-6 $R^3$ as permitted by valency;

$R^1$ and $R^2$ are each independently a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-12}$ alkylene)-$N_3$, —($C_{1-12}$ alkylene)-($OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

In embodiments of the compounds of formula (I-3), when $X^3$ is unsubstituted, then the leaving group is not

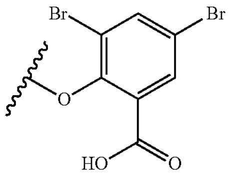

or

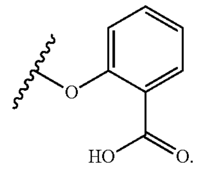

In embodiments, the compound of formula (I-3), or a salt, or a stereoisomer thereof, comprises one or more $^{13}C$ isotopes of carbon atoms occurring in the compound.

In some embodiments of the compounds of formula (I-3), or a salt, stereoisomer, or deuterated form thereof, $X^3$ is $C_{1-12}$ alkylene, $C_{2-12}$ alkenylene, or $C_{2-12}$ alkynylene, each of which is optionally substituted with 1-6 $R^3$ as permitted by valency. In some embodiments, each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen.

In some embodiments, $X^3$ is $C_{1-12}$ alkylene, $C_{2-11}$ alkylene, $C_{3-10}$ alkylene, $C_{4-9}$ alkylene, $C_{5-8}$ alkylene, or $C_{6-7}$ alkylene, each of which is optionally substituted with 1-6, 2-5, or 3-4 $R^3$ as permitted by valency. In some embodiments, $X^3$ is $C_{2-12}$ alkenylene, $C_{3-11}$ alkenylene, $C_{4-10}$ alkenylene, $C_{5-9}$ alkenylene, $C_{6-8}$ alkenylene, or $C_7$ alkenylene, each of which is optionally substituted with 1-6, 2-5, or 3-4 $R^3$ as permitted by valency. In some embodiments, $X^3$ is $C_2$. 12 alkynylene, $C_{3-11}$ alkynylene, $C_{4-10}$ alkynylene, $C_{5-9}$ alkynylene, $C_{6-8}$ alkynylene, or $C_7$ alkynylene, each of which is optionally substituted with 1-6, 2-5, or 3-4 $R^3$ as permitted by valency. In some embodiments, $X^3$ is unsubstituted $C_{1-12}$ alkylene, $C_{2-12}$ alkenylene, or $C_{2-12}$ alkynylene. In some embodiments, $X^3$ is straight (i.e., unbranched) $C_{1-12}$ alkylene, $C_{2-12}$ alkenylene, or $C_{2-12}$ alkynylene.

In some embodiments of the compounds of formula (I-3), or a salt, stereoisomer, or deuterated form thereof, $X^3$ is $C_{1-6}$ alkylene, $C_{2-6}$ alkenylene, or $C_{2-6}$ alkynylene, each of which is optionally substituted with 1 or 2 $R^3$ as permitted by valency. In some embodiments, $X^3$ is unsubstituted $C_{1-6}$ alkylene, $C_{2-6}$ alkenylene, or $C_{2-6}$ alkynylene. In some embodiments, $X^3$ is straight $C_{1-6}$ alkylene, $C_{2-6}$ alkenylene, or $C_{2-6}$ alkynylene.

In some embodiments of the compounds of formula (I-3), or a salt, stereoisomer, or deuterated form thereof, $X^3$ is $C_{1-6}$ alkylene optionally substituted with 1 or 2 $R^3$ as permitted by valency. In some embodiments, $X^3$ is unsubstituted $C_{1-6}$ alkylene. In some embodiments, $X^3$ is straight $C_{1-6}$ alkylene. In embodiments, $X^3$ is

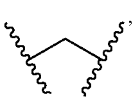

,

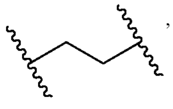

,

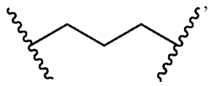

,

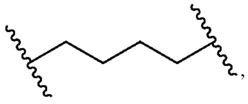

,

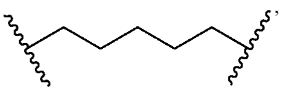

, or

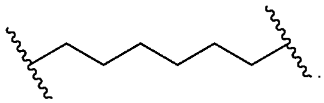

.

In some embodiments of the compounds of formula (I-3), or a salt, stereoisomer, or deuterated form thereof, $X^3$ is $C_{2-6}$ alkenylene optionally substituted with 1 or 2 $R^3$ as permitted by valency. In some embodiments, $X^3$ is unsubstituted $C_{2-6}$ alkenylene. In some embodiments, $X^3$ is straight $C_{2-6}$ alkenylene. In some embodiments, $X^3$ is

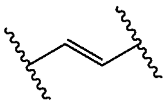

or

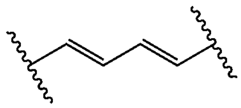

.

In some embodiments of the compounds of formula (I-3), or a salt, stereoisomer, or deuterated form thereof, $X^3$ is $C_{2-6}$ alkynylene optionally substituted with 1 or 2 $R^3$ as permitted by valency. In some embodiments, $X^3$ is unsubstituted $C_{2-6}$ alkynylene. In some embodiments, X is straight $C_{2-6}$ alkynylene. In embodiments, $X^3$ is

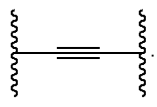

.

In some embodiments of the compounds of formula (I-3), or a salt, stereoisomer, or deuterated form thereof, $X^3$ is $C_{1-6}$ alkylene, $C_{2-6}$ alkenylene, or $C_{2-6}$ alkynylene, each of which is substituted with —S—($C_{1-6}$ alkylene)-$(OCH_2CH_2)_m$—$(CH_2)_n$—$N_3$, or —O—($C_{1-6}$ alkylene)-$(OCH_2CH_2)_m$—$(CH_2)_n$—$N_3$, and wherein each m is independently an integer of 1-50, 2-40, 3-30, 4-25, 5-20, 6-18, 7-16, 8-14, 9-12, or 10-11, and each n is independently an integer of 0-25, 1-20, 2-15, 3-10, 4-8, or 5-7. In some embodiments, $X^3$ is $C_{1-6}$ alkylene substituted with —S—($C_{1-6}$ alkylene)-$(OCH_2CH_2)_m$—$(CH_2)_n$—$N_3$, and wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In some embodiments, $X^3$ is

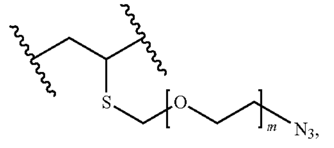

and wherein m is an integer of 1-25, 2-20, 3-15, 4-10, or 5-8. In some embodiments, m is 3-8, 4-7, or 5-6. In some embodiments, $X^3$ is

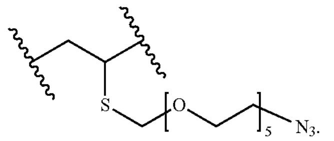

In embodiments, $X^3$ is $C_{1-6}$ alkylene substituted with $—S—(C_{1-6}$ alkylene)-$(OCH_2CH_2)_m—(CH_2)_n—N_3$, and wherein m is an integer of 1-50, and n is an integer of 0-25. In embodiments, $X^3$ is

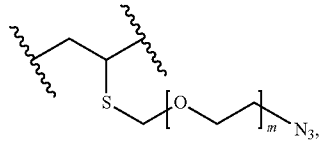

and wherein m is an integer of 1-25. In embodiments, $X^3$ is

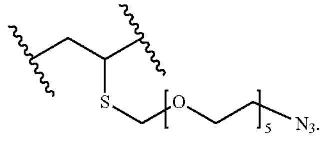

In embodiments, $X^3$ is $C_{1-24}$ alkylene $C_{2-20}$ alkylene, $C_{3-18}$ alkylene, $C_{4-14}$ alkylene, $C_{5-12}$ alkylene, or $C_{6-10}$ alkylene substituted with $—(C_{1-12}$ alkylene)-$N_3$, $—(C_{2-10}$ alkylene)-$N_3$, $—(C_{3-8}$ alkylene)-$N_3$, or $—(C_{4-6}$ alkylene)-$N_3$. In embodiments, $X^3$ is $C_{1-6}$ alkylene substituted with $—(C_{1-12}$ alkylene)-$N_3$. In embodiments, $X^3$ is $C_{1-6}$ alkylene substituted with $—(C_{2-8}$ alkylene)-$N_3$. In embodiments, $X^3$ is $C_{2-4}$ alkylene substituted with $—(C_2$ alkylene)-$N_3$, $—(C_3$ alkylene)-$N_3$, $—(C_4$ alkylene)-$N_3$, $—(C_5$ alkylene)-$N_3$, $—(C_6$ alkylene)-$N_3$, $—(C_7$ alkylene)-$N_3$, or $—(C_8$ alkylene)-$N_3$. In embodiments, $X^3$ is

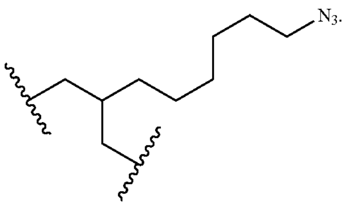 [SMILES: *CC(C*)CCCCCCN=[N+]=[N-]]

Compounds of Formula (I-4)

In embodiments, the present disclosure provides a compound of formula (I-4):

(I-4)

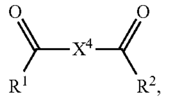

or a salt, a stereoisomer, or a deuterated form thereof, wherein:

$X^4$ is $C_{3-9}$ cycloalkylene, $C_{3-9}$ cycloalkenylene, 5-12 membered heterocyclylene containing 1 or 2 heteroatoms selected from N, S, or O, wherein $X^4$ is optionally substituted with 1-6 $R^3$ as permitted by valency;

$R^1$ and $R^2$ are each independently a leaving group;

each $R^3$ is independently —OH, —CN, $—NO_2$, halogen, oxo, $—C_{1-6}$ alkyl, $—C_{1-6}$ haloalkyl, $—O(C_{1-6}$ alkyl), $—S(C_{1-6}$ alkyl), $—SO(C_{1-6}$ alkyl), $—SO_2(C_{1-6}$ alkyl), $—(C_{1-12}$ alkylene)-$N_3$, $—(C_{1-12}$ alkylene)-$(OCH_2CH_2)_m—(CH_2)_n—N_3$, $—C(O)NH—(C_{1-12}$ alkylene)-$(OCH_2CH_2)_m—(CH_2)_n—N_3$, $—NHC(O)—(C_{1-12}$ alkylene)-$(OCH_2CH_2)_m—(CH_2)_n—N_3$, $—O—(C_{1-12}$ alkylene)-$(OCH_2CH_2)_m—(CH_2)_n—N_3$, $—S—(C_{1-12}$ alkylene)-$(OCH_2CH_2)_m—(CH_2)_n—N_3$, or $—C(O)—R^1$, wherein each alkyl or alkylene is optionally and independently substituted with $—C_{1-6}$ alkyl, —OH, —CN, $—NO_2$, or halogen;

each m is independently an integer of 1-200; and each n is independently an integer of 0-50.

In embodiments, the compound of formula (I-4), or a salt, or a stereoisomer thereof, comprises one or more $^{13}C$ isotopes of carbon atoms occurring in the compound.

In embodiments of the compound of formula (I-4), or a salt, a stereoisomer, or a deuterated form thereof, $X^4$ is $C_{3-9}$ cycloalkylene, $C_{3-9}$ cycloalkenylene, or 5-12 membered heterocyclylene, each of which is optionally substituted with 1 or 2 $R^3$ as permitted by valency. In some embodiments, each $R^3$ is independently —OH, —CN, $—NO_2$, halogen, oxo, $—C_{1-6}$ alkyl, $—C_{1-6}$ haloalkyl, $—O(C_{1-6}$ alkyl), $—S(C_{1-6}$ alkyl), $—SO(C_{1-6}$ alkyl), $—SO_2(C_{1-6}$ alkyl), $—(C_{1-6}$ alkylene)-$N_3$, $—(C_{1-12}$ alkylene)-$(OCH_2CH_2)_m—(CH_2)_n—N_3$, $—C(O)NH—(C_{1-12}$ alkylene)-$(OCH_2CH_2)_m—(CH_2)_n—N_3$, $—NHC(O)—(C_{1-12}$ alkylene)-$(OCH_2CH_2)_m—(CH_2)_n—N_3$, $—O—(C_{1-12}$ alkylene)-$(OCH_2CH_2)_m—(CH_2)_n—N_3$, $—S—(C_{1-12}$ alkylene)-$(OCH_2CH_2)_m—(CH_2)_n—N_3$, or $—C(O)—R^1$, wherein each alkyl or alkylene is optionally and independently substituted with $—C_{1-6}$ alkyl, —OH, —CN, $—NO_2$, or halogen. In some embodiments, $X^4$ is unsubstituted $C_{3-9}$ cycloalkylene, $C_{3-9}$ cycloalkenylene, or 5-12 membered heterocyclylene.

In some embodiments, $X^4$ is $C_{3-9}$ cycloalkylene, $C_{4-8}$ cycloalkylene, $C_{5-7}$ cycloalkylene, or $C_6$ cycloalkylene, each of which is optionally substituted with 1 or 2 $R^3$ as permitted by valency. In some embodiments, $X^4$ is $C_{3-9}$ cycloalkenylene, $C_{4-8}$ cycloalkenylene, $C_{5-7}$ cycloalkenylene, or $C_6$ cycloalkenylene, each of which is optionally substituted with 1 or 2 $R^3$ as permitted by valency. In some embodiments, $X^4$ is 5-12 membered, 6-11 membered, 7-10 membered, or 8-9 membered heterocyclylene containing a heteroatom which is S, O, or N, each of which is optionally substituted with 1 or 2 $R^3$ as permitted by valency.

In some embodiments of the compounds of formula (I-4), or a salt, stereoisomer, or deuterated form thereof, $X^4$ is $C_{3-7}$ cycloalkylene or $C_{4-6}$ cycloalkylene optionally substituted with 1 or 2 $R^3$ as permitted by valency. In some embodiments, $X^4$ is unsubstituted $C_{3-7}$ cycloalkylene or $C_{4-6}$ cycloalkylene. In embodiments, $X^4$ is

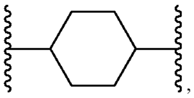,
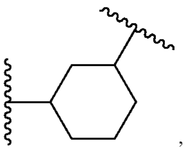, or
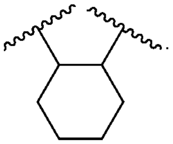.

In some embodiments of the compounds of formula (I-4), or a salt, stereoisomer, or deuterated form thereof, $X^4$ is $C_{3-7}$ cycloalkenylene or $C_{4-6}$ cycloalkenylene optionally substituted with 1 or 2 $R^3$ as permitted by valency. In some embodiments, $X^4$ is unsubstituted $C_{3-7}$ cycloalkenylene or $C_{4-6}$ cycloalkenylene. In embodiments, $X^4$ is

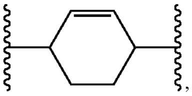,
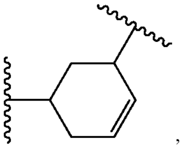,
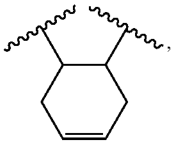,
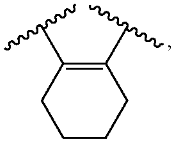, or
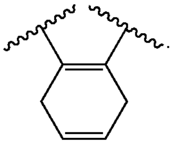.

In some embodiments of the compounds of formula (I-4), or a salt, stereoisomer, or deuterated form thereof, $X^4$ is $C_{3-7}$ cycloalkenylene or $C_{4-6}$ cycloalkenylene substituted with —($C_{1-12}$ alkylene)-$N_3$, —($C_{1-9}$ alkylene)-$N_3$, —($C_{1-6}$ alkylene)-$N_3$, —($C_{2-5}$ alkylene)-$N_3$, or —($C_{3-4}$ alkylene)-$N_3$. In embodiments, $X^4$ is

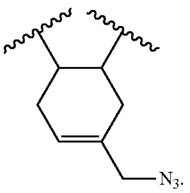 [SMILES: *C1CC=C(CN=[N+]=[N-])CC1*]

In embodiments, $C_{3-9}$ cycloalkylene, $C_{3-9}$ cycloalkenylene, or 5-12 membered heterocyclylene is a bridged ring system, a fused ring system, or a spiro ring system.

In some embodiments of the compounds of formula (I-4), or a salt, stereoisomer, or deuterated form thereof, $X^4$ is a 5-12 membered, 6-11 membered, 7-10 membered, or 8-9 membered heterocyclylene containing a heteroatom which is S or O, and wherein the heterocyclylene is optionally substituted. In some embodiments, the heterocyclylene is optionally substituted with —($C_{1-6}$ alkylene)-$N_3$. In some embodiments, $X^4$ is a 6-10 membered, or 7-9 membered heterocyclylene containing O, and wherein the heterocyclylene is substituted with —($C_{1-6}$ alkylene)-$N_3$. In embodiments, $X^4$ is

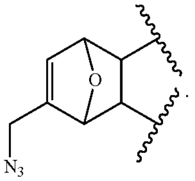 [SMILES: *C1C2C=C(CN=[N+]=[N-])C(O2)C1*].

$R^1$ and $R^2$ as Leaving Groups

In some embodiments of the compounds of formula (I), or a salt, stereoisomer, or deuterated form thereof, $R^1$ and $R^2$ are each independently —OH, halogen, or a leaving group. In some embodiments, $R^1$ and $R^2$ are each independently halogen (e.g., —F, —Cl, —Br, —I), or a leaving group. In some embodiments, $R^1$ and $R^2$ are each independently a leaving group. In some embodiments, $R^1$ and $R^2$ are the same. In some embodiments, $R^1$ and $R^2$ are different.

In embodiments of the compound of formula (I-1), (I-2), (I-3), or (I-4), or a salt, a stereoisomer, or a deuterated form thereof, $R^1$ and $R^2$ are each independently a leaving group, which is

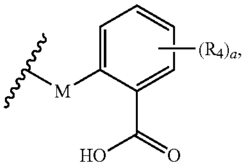, wherein M is O or S, each $R^4$ is independently halogen or —$C_{1-6}$ alkyl; and a is an integer of 0-4, or 1-3, or 2.

In embodiments, if $X^1$ of the compound of formula (I-1) is

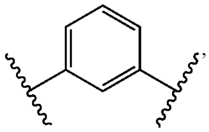 [SMILES: *c1cccc(*)c1], then the leaving group is not

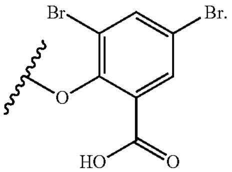 [SMILES: *Oc1c(Br)cc(Br)cc1C(=O)O]

In embodiments, if $X^1$ of the compound of formula (I-1) is an arylene substituted with 1 $R^3$, then $R^3$ is different from —C(O)—$R^1$ or —C(O)—$R^2$.

In embodiments, when $X^3$ of the compound of formula (I-3) is unsubstituted, then the leaving group is not

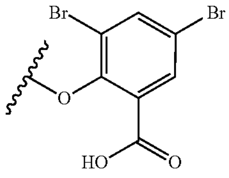

or

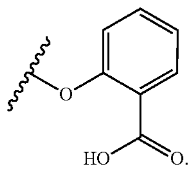 [SMILES: *Oc1ccccc1C(=O)O]

In some embodiments, M is O, and a is 0, and the leaving group is

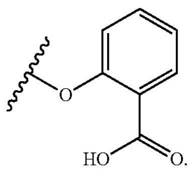

In some embodiments, M is S, and a is 0, and the leaving group is

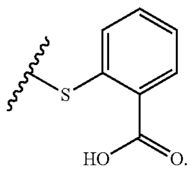

In some embodiments, a is 1, 2, or 3. In some embodiments, each $R^4$ is halogen (—F, —Cl, —Br, —I). In some embodiments, each $R^4$ is independently —F, —Cl, or —Br. In some embodiments, a is 2 and each $R^4$ is —Br, and the leaving group is

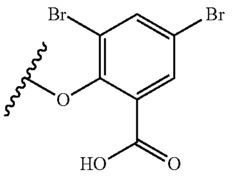

or

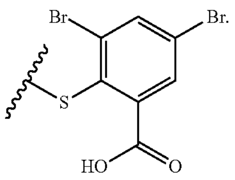

In some embodiments, a is 2 and each $R^4$ is —Cl, and the leaving group is

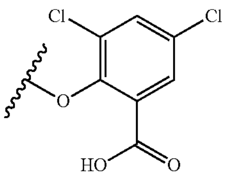

or

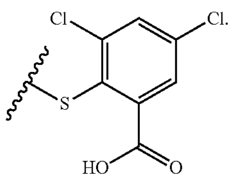

In some embodiments, a is 1, and $R^4$ is —Br, and the leaving group is

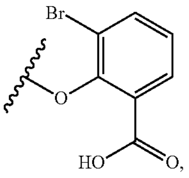

,

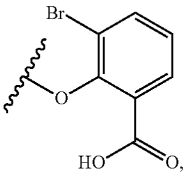

,

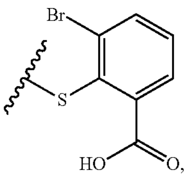

, or

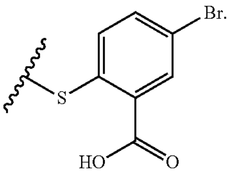

In some embodiments of the compounds of formula (I-1), (1-2), (I-3), or (I-4), or a salt, stereoisomer, or deuterated form thereof, $R^1$ and $R^2$ are

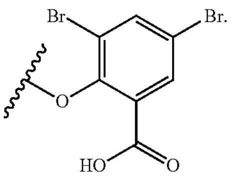 [SMILES: *Oc1c(Br)cc(Br)cc1C(=O)O]

In some embodiments of the compounds of formula (I-1), (I-2), (I-3), or (I-4), or a salt, stereoisomer, or deuterated form thereof, $R^1$ and $R^2$ are

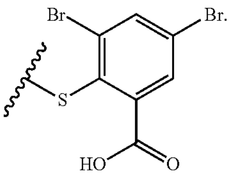

In some embodiments of the compounds of formula (I-1), (I-2), (1-3), or (I-4), or a salt, stereoisomer, or deuterated form thereof, $R^1$ and $R^2$ are

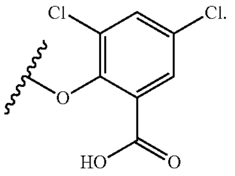

In some embodiments of the compounds of formula (I-1), (I-2), (I-3), or (I-4), or a salt, stereoisomer, or deuterated form thereof, $R^1$ and $R^2$ are

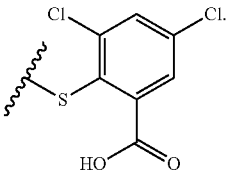 [SMILES: *Sc1c(Cl)cc(Cl)cc1C(=O)O]

In some embodiments of the compounds of formula (I-1), (I-2), (I-3), or (I-4), or a salt, stereoisomer, or deuterated form thereof, $R^1$ and $R^2$ are

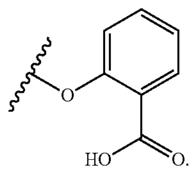 [SMILES: *Oc1ccccc1C(=O)O]

In some embodiments of the compounds of formula (I-1), (I-2), (I-3), or (I-4), or a salt, stereoisomer, or deuterated form thereof, $R^1$ and $R^2$ are

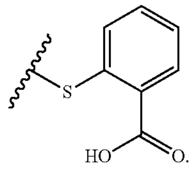 [SMILES: *Sc1ccccc1C(=O)O]

In embodiments of the compound of formula (I-1), (I-2), (I-3), or (I-4), or a salt, a stereoisomer, or a deuterated form thereof, the leaving group is

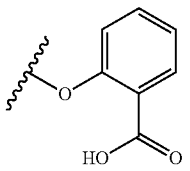

or

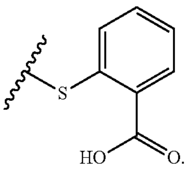 [SMILES: *Sc1ccccc1C(=O)O]

In embodiments of the compound of formula (I-1), (I-2), (I-3), or (I-4), or a salt, a stereoisomer, or a deuterated form thereof, the leaving group is

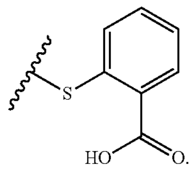

In embodiments of the compound of formula (I-1), (I-2), (I-3), or (I-4), or a salt, a stereoisomer, or a deuterated form thereof, each $R^4$ is halogen. In embodiments, each $R^4$ is independently —F, —Cl, or —Br. In embodiments, the leaving group is

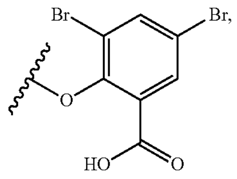

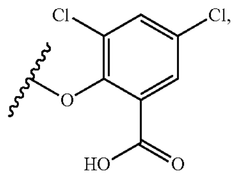

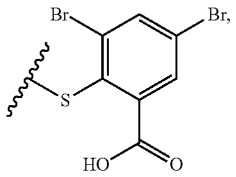

or

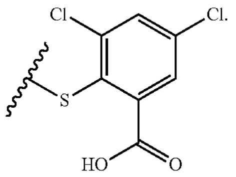

In embodiments, the leaving group is

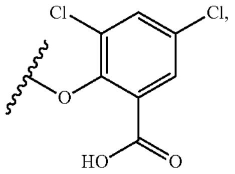

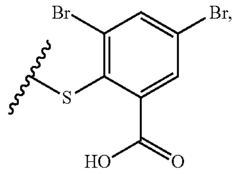

or

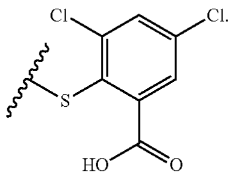

In some embodiments of the compounds of formula (I-1), (I-2), (I-3), or (I-4), or a salt, stereoisomer, or deuterated form thereof, $R^1$ and $R^2$ are each independently a leaving group, which is —O—($C_{1-6}$ alkylene)-$SO_3H$. In some embodiments, $R^1$ and $R^2$ are each independently a leaving group selected from the group consisting of —O—($CH_2$)—$SO_3H$, —O—($CH_2CH_2$)—$SO_3H$, —O—($CH_2CH_2CH_2$)—$SO_3H$, and —O—($CH_2CH_2CH_2CH_2$)—$SO_3H$. In some embodiments, the leaving group is —O—($CH_2CH_2$)—$SO_3H$. In some embodiments of the compounds of formula (I-1), (I-2), (I-3), or (I-4), or a salt, stereoisomer, or deuterated form thereof, $R^1$ and $R^2$ are —O—($CH_2CH_2$)—$SO_3H$.

TABLE A
| Various exemplary compounds of the disclosure | | |
|---|---|---|
| Comp. ID | Abbreviation | Structure |
| 1 | DBSF | 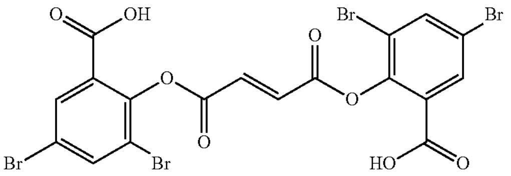 [SMILES: O=C(/C=C/C(=O)Oc1c(Br)cc(Br)cc1C(=O)O)Oc1c(Br)cc(Br)cc1C(=O)O] |
| 2 | DBSG | 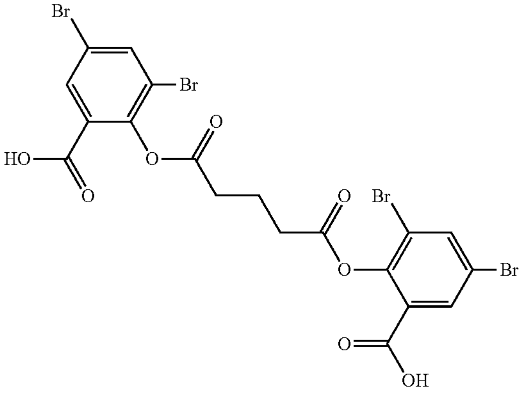 [SMILES: O=C(CCCC(=O)Oc1c(Br)cc(Br)cc1C(=O)O)Oc1c(Br)cc(Br)cc1C(=O)O] |
| 3 | DBSS | 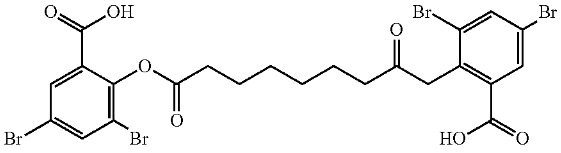 [SMILES: O=C(CCCCCCC(=O)Oc1c(Br)cc(Br)cc1C(=O)O)Cc1c(Br)cc(Br)cc1C(=O)O] |
| 4 | TTDS | 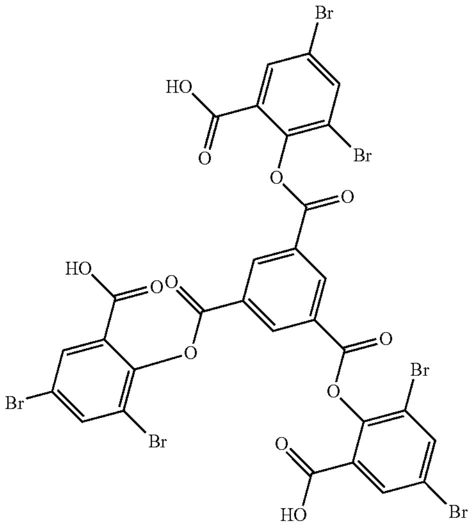 [SMILES: O=C(Oc1c(Br)cc(Br)cc1C(=O)O)c1cc(C(=O)Oc2c(Br)cc(Br)cc2C(=O)O)cc(C(=O)Oc2c(Br)cc(Br)cc2C(=O)O)c1] |

TABLE A-continued
| Various exemplary compounds of the disclosure | | |
|---|---|---|
| Comp. ID | Abbreviation | Structure |
| 5 | TTS | 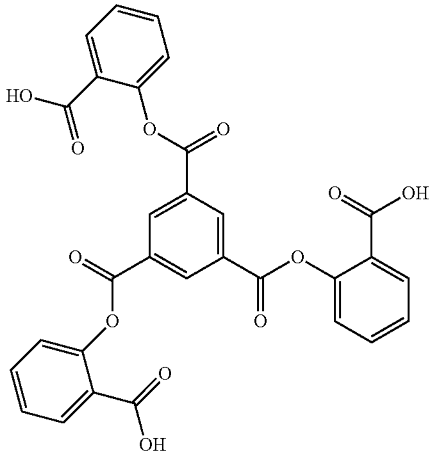 [SMILES: O=C(Oc1ccccc1C(=O)O)c1cc(C(=O)Oc2ccccc2C(=O)O)cc(C(=O)Oc2ccccc2C(=O)O)c1] |
| 6 | DBSM | 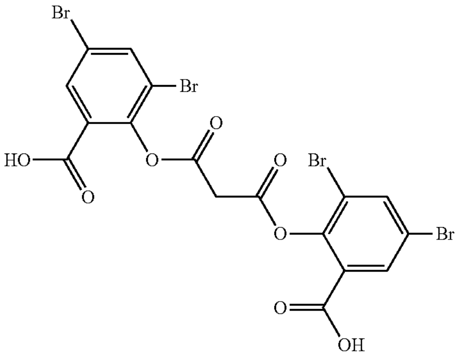 [SMILES: O=C(CC(=O)Oc1c(Br)cc(Br)cc1C(=O)O)Oc1c(Br)cc(Br)cc1C(=O)O] |
| 7 | DBST | 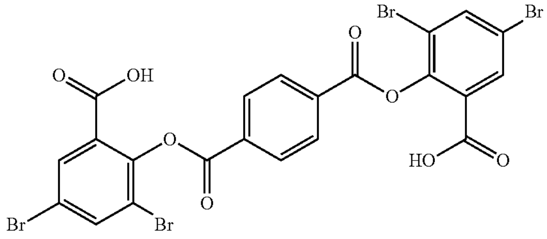 [SMILES: O=C(Oc1c(Br)cc(Br)cc1C(=O)O)c1ccc(C(=O)Oc2c(Br)cc(Br)cc2C(=O)O)cc1] |
| 8 | DBSI | 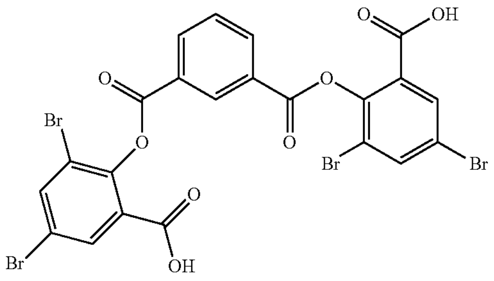 [SMILES: O=C(Oc1c(Br)cc(Br)cc1C(=O)O)c1cccc(C(=O)Oc2c(Br)cc(Br)cc2C(=O)O)c1] |

TABLE A-continued
| Various exemplary compounds of the disclosure | | |
|---|---|---|
| Comp. ID | Abbreviation | Structure |
| 9 | BSI | 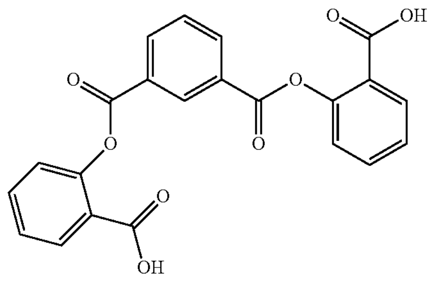 [SMILES: O=C(Oc1ccccc1C(=O)O)c1cccc(C(=O)Oc2ccccc2C(=O)O)c1] |
| 10 | BSAF | 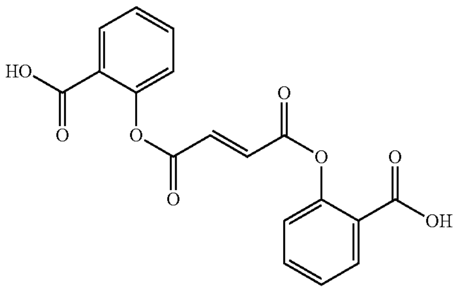 [SMILES: O=C(/C=C/C(=O)Oc1ccccc1C(=O)O)Oc1ccccc1C(=O)O] |
| 11 | BSEIA | 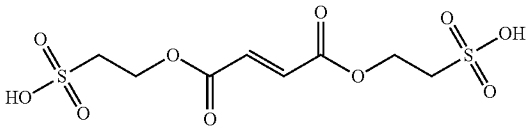 [SMILES: O=C(/C=C/C(=O)OCCS(=O)(=O)O)OCCS(=O)(=O)O] |
| 12 | BTASF | 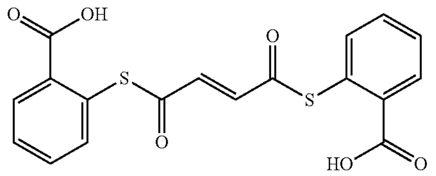 [SMILES: O=C(/C=C/C(=O)Sc1ccccc1C(=O)O)Sc1ccccc1C(=O)O] |
| 13 | DCSF | 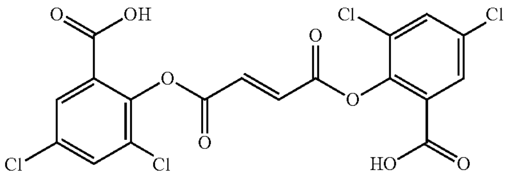 [SMILES: O=C(/C=C/C(=O)Oc1c(Cl)cc(Cl)cc1C(=O)O)Oc1c(Cl)cc(Cl)cc1C(=O)O] |
| 14 | DCSIA | 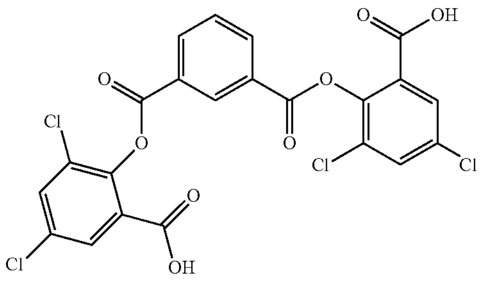 [SMILES: O=C(Oc1c(Cl)cc(Cl)cc1C(=O)O)c1cccc(C(=O)Oc2c(Cl)cc(Cl)cc2C(=O)O)c1] |

TABLE A-continued
| Various exemplary compounds of the disclosure | | |
|---|---|---|
| Comp. ID | Abbreviation | Structure |
| 15 | DBSNP-4 | 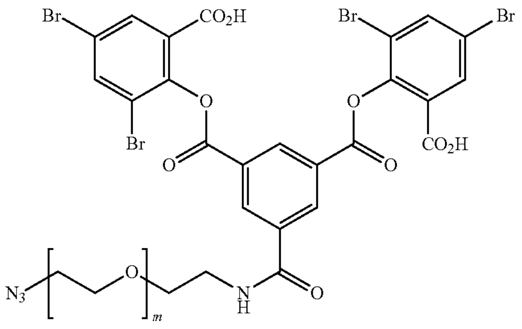 m = 4 |
| 16 | DBSNP-9 | 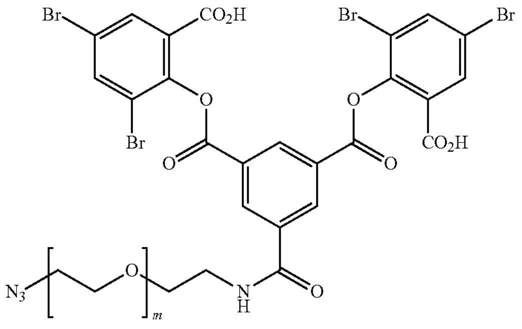 m = 9 |
| 17 | DBSNP-42 | 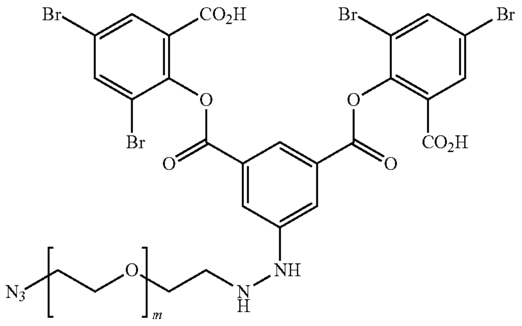 m = 4 |
| 18 | DBSNP-92 | 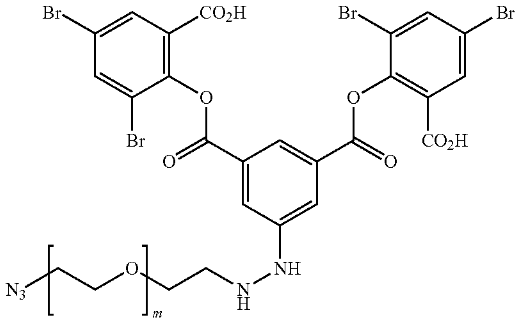 m = 9 |

TABLE A-continued
| Various exemplary compounds of the disclosure | | |
|---|---|---|
| Comp. ID | Abbreviation | Structure |
| 19 | TIDA | 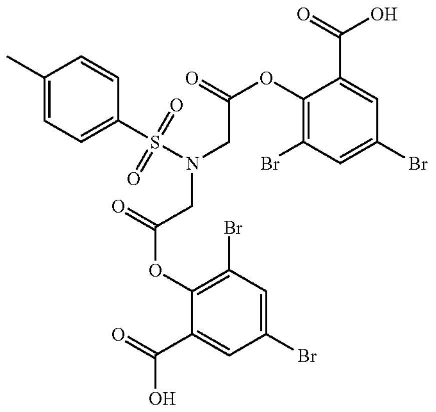 [SMILES: Cc1ccc(S(=O)(=O)N(CC(=O)Oc2c(Br)cc(Br)cc2C(=O)O)CC(=O)Oc2c(Br)cc(Br)cc2C(=O)O)cc1] |
| 20 | AIDA | 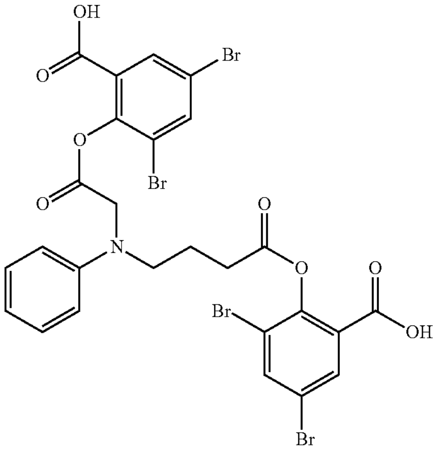 [SMILES: O=C(CCCN(CC(=O)Oc1c(Br)cc(Br)cc1C(=O)O)c1ccccc1)Oc1c(Br)cc(Br)cc1C(=O)O] |
| 21 | MIDA | 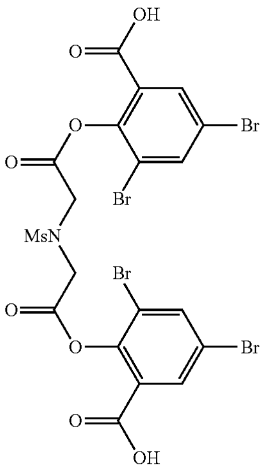 |

TABLE A-continued
| Various exemplary compounds of the disclosure | | |
|---|---|---|
| Comp. ID | Abbreviation | Structure |
| 22 | IDDBSN | 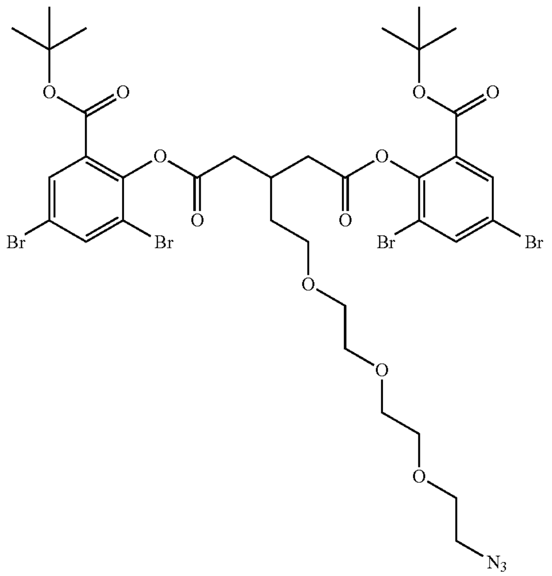 [SMILES: CC(C)(C)OC(=O)c1cc(Br)cc(Br)c1OC(=O)CC(CCOCCOCCOCCN=[N+]=[N-])CC(=O)Oc1c(Br)cc(Br)cc1C(=O)OC(C)(C)C] |
| 23 | AZS3 | 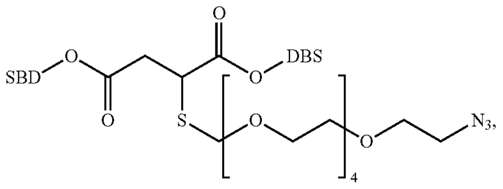 DBS represents 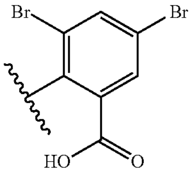 [SMILES: *c1c(Br)cc(Br)cc1C(=O)O] |
| 24 | FuranDA | 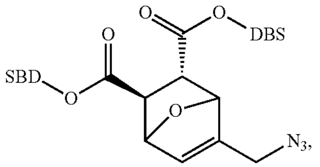 DBS represents 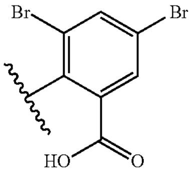 [SMILES: *c1c(Br)cc(Br)cc1C(=O)O] |

TABLE A-continued
| Various exemplary compounds of the disclosure | | |
|---|---|---|
| Comp. ID | Abbreviation | Structure |
| 25 | | 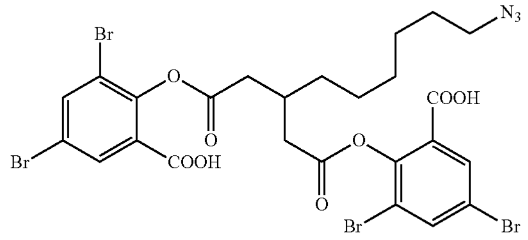 [SMILES: [N-]=[N+]=NCCCCCCC(CC(=O)Oc1c(Br)cc(Br)cc1C(=O)O)CC(=O)Oc1c(Br)cc(Br)cc1C(=O)O] |
In embodiments, the compound of formula (I) or (I-3) is not
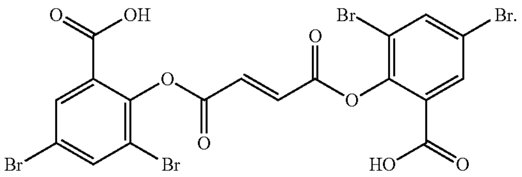 [SMILES: O=C(/C=C/C(=O)Oc1c(Br)cc(Br)cc1C(=O)O)Oc1c(Br)cc(Br)cc1C(=O)O]
In embodiments, the compound of formula (I) or (I-1) is not
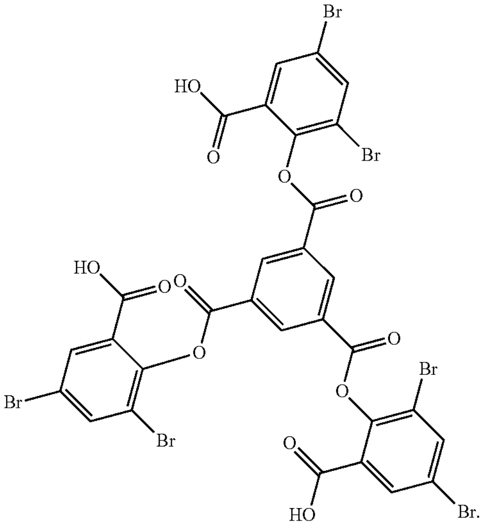 [SMILES: O=C(Oc1c(Br)cc(Br)cc1C(=O)O)c1cc(C(=O)Oc2c(Br)cc(Br)cc2C(=O)O)cc(C(=O)Oc2c(Br)cc(Br)cc2C(=O)O)c1]
In embodiments, the compound of formula (I) or (I-3) is not
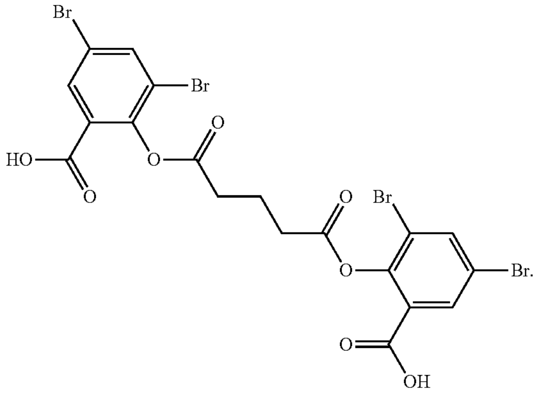 [SMILES: O=C(CCCC(=O)Oc1c(Br)cc(Br)cc1C(=O)O)Oc1c(Br)cc(Br)cc1C(=O)O]
In embodiments, the compound of formula (I) or (I-3) is not
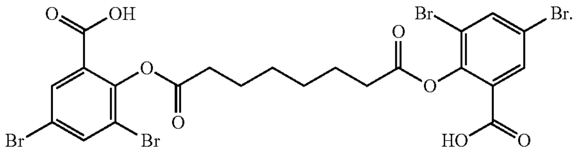 [SMILES: O=C(CCCCCCC(=O)Oc1c(Br)cc(Br)cc1C(=O)O)Oc1c(Br)cc(Br)cc1C(=O)O]
In embodiments, the compound of formula (I) or (I-1) is not
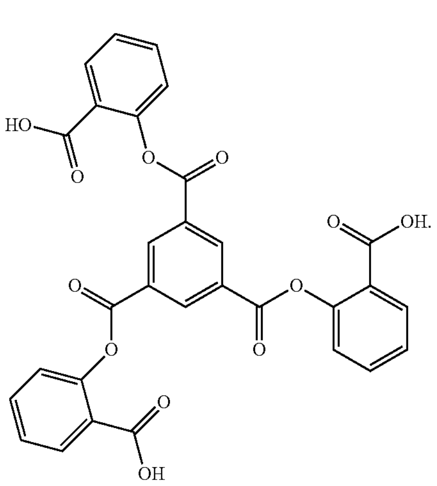 [SMILES: O=C(Oc1ccccc1C(=O)O)c1cc(C(=O)Oc2ccccc2C(=O)O)cc(C(=O)Oc2ccccc2C(=O)O)c1]

In embodiments, the compound of formula (I) or (I-3) is not

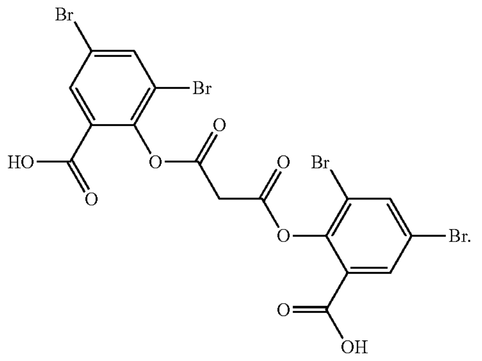 [SMILES: O=C(CC(=O)Oc1c(Br)cc(Br)cc1C(=O)O)Oc1c(Br)cc(Br)cc1C(=O)O]

In embodiments, the compound of formula (I) or (I-1) is not

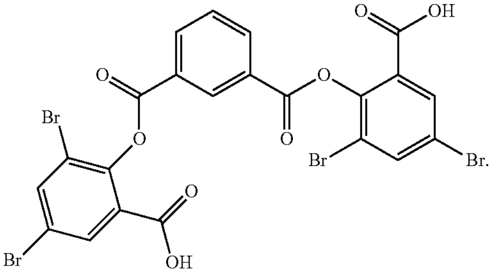

In embodiments, the compound of formula (I) or (I-3) is not

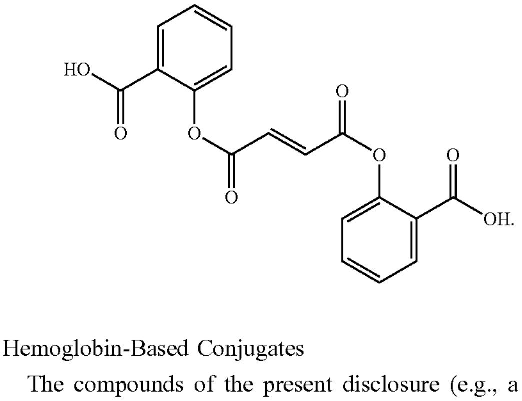

Hemoglobin-Based Conjugates

The compounds of the present disclosure (e.g., a compound of formula (I), (I-1), (I-2), (I-3), or (I-4), or Table A, or a salt, stereoisomer, or deuterated form thereof) may be used on their own or used as a multifunctional linker compound to link a protein, a peptide, or an amino acid. In embodiments, the compound disclosed herein can act as a bifunctional linker (e.g.,

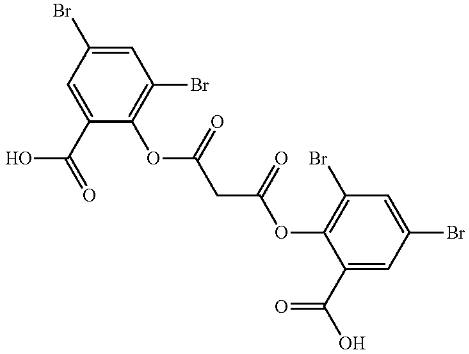

,

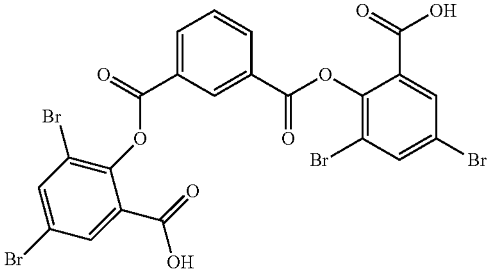 [SMILES: O=C(Oc1c(Br)cc(Br)cc1C(=O)O)c1cccc(C(=O)Oc2c(Br)cc(Br)cc2C(=O)O)c1]

).

In embodiments, the compound disclosure herein can act as a trifunctional linker (e.g.,

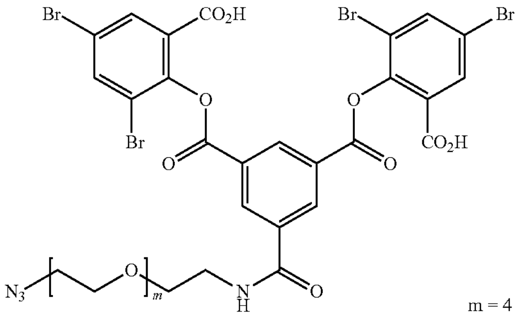

m = 4,

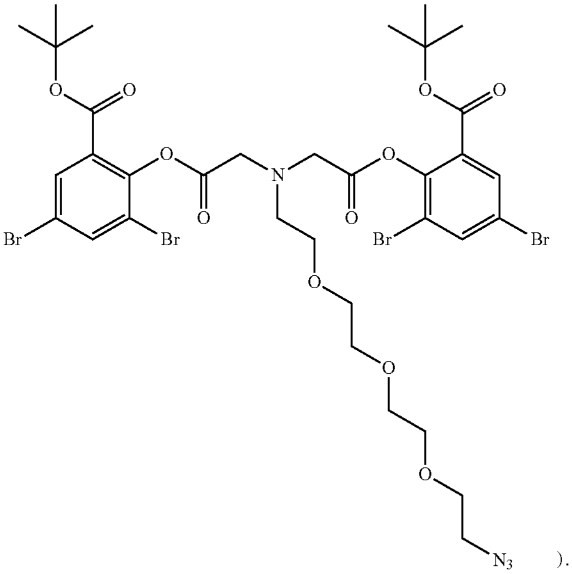

).

In another aspect of the present disclosure, a conjugated composition is provided. The conjugated composition comprises a reacted unit of a molecule and a compound of the present disclosure (e.g., a compound of formula (I), (I-1), (1-2), (I-3), or (I-4), or Table A, or a salt, stereoisomer, or deuterated form thereof). As used herein, the molecule is a compound having at least one functional group (e.g., a terminal amine group) capable of reacting with the compounds disclosed herein. In embodiments, the molecule has at least two functional groups capable of reacting with the compounds disclosed herein. In embodiments, the conjugated composition is obtained by crosslinking the molecule with the compound of the disclosure. In embodiments, the molecule is a protein, or a peptide. In embodiments, the molecule is a protein. In embodiments, the molecule is a protein having two or more lysine residues. In embodiments, the conjugated composition is obtained by crosslinking two or more lysine residues (e.g., two, three lysine residues) of the protein with the compound of the present disclosure, or a salt, a stereoisomer, or a deuterated form thereof. In some embodiments, the protein is a hemoglobin protein.

Bovine hemoglobin is a heterotetramer consisting of two alpha and two beta hemoglobin subunits. Each alpha monomer binds to a beta monomer forming an ab heterodimer. Two ab dimers associate to form the heterotetramer. These tetramers are relatively stable (although they can dissociate to alpha-beta dimers, which are toxic, see below) and can change between the relaxed oxygenated R-state and the deoxygenated T-state. For its native function, the hemoglobin transits through these two states to either release or bind oxygen. The ability of hemoglobin to cycle through these two states is described by the $P_{50}$ value. A high $P_{50}$ value correlates with an inability to bind oxygen efficiently while a low $P_{50}$ value correlates with tight oxygen binding but a reduced ability to release bound oxygen.

When the tetramer dissociates into its two heterodimers it can start to dissociate into the individual monomers, which are cleared through the kidney. Unfortunately, the clearance of larger hemoglobin amounts can cause severe distress in the kidneys and terminal kidney failure.

Accordingly, there is a need to develop stabilized hemoglobin protein.

In embodiments, the present disclosure further provides a hemoglobin-based conjugate, comprising a reacted unit of a hemoglobin and a compound of the present disclosure (e.g., a compound of formula (I), (I-1), (I-2), (I-3), or (I-4), or Table A), or a salt, stereoisomer, or deuterated form thereof.

In embodiments, the hemoglobin-based conjugate is obtained by crosslinking the hemoglobin with the compound of the present disclosure (e.g., a compound of formula (I), (I-1), (I-2), (I-3), or (I-4), or Table A), or a salt, stereoisomer, or deuterated form thereof. In embodiments, the hemoglobin-based conjugate is obtained by crosslinking two or more lysine residues (e.g., two, three lysine residues) of the hemoglobin with the compound of the present disclosure, or a salt, stereoisomer, or deuterated form thereof. In embodiments, the hemoglobin is bovine, human, equine, porcine, ovine, simian, or fish hemoglobin. In embodiments, the hemoglobin is bovine hemoglobin.

Numbered Embodiments of the Disclosure

In addition to the disclosure above, the Examples below, and the appended claims, the disclosure sets forth the following numbered embodiments.

1. A compound of formula (I)

(I)

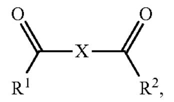

or a salt, a stereoisomer, or a deuterated form thereof, wherein:

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, arylene, heteroarylene, or $-L^1-NR^A-L^2-$, wherein X is optionally substituted with 1-6 $R^3$ as permitted by valency;

$R^1$ and $R^2$ are each independently —OH, halogen, or a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-12}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

$R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-$(OCH_2CH_2)_m$—$(CH_2)_n$—$N_3$, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

2. The compound of embodiment 1, or a salt, a stereoisomer, or a deuterated form thereof, wherein $R^1$ and $R^2$ are a leaving group, and wherein:

the leaving group is

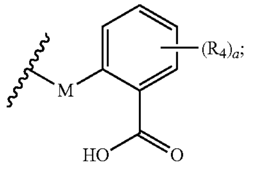

M is O or S;

each $R^4$ is independently halogen or —$C_{1-6}$ alkyl; and a is an integer of 0-4.

3. The compound of embodiment 2, or a salt, a stereoisomer, or a deuterated form thereof, wherein the leaving group is

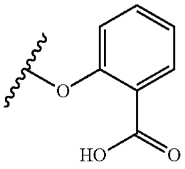
or
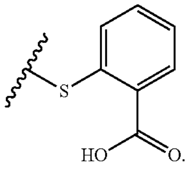

4. The compound of embodiment 2, or a salt, a stereoisomer, or a deuterated form thereof, wherein a is 1, 2, or 3.
5. The compound of embodiment 4, or a salt, a stereoisomer, or a deuterated form thereof, wherein each $R^4$ is halogen.
6. The compound of embodiment 4 or 5, or a salt, a stereoisomer, or a deuterated form thereof, wherein each $R^4$ is independently —F, —Cl, or —Br.
7. The compound of any one of embodiments 2 and 4-6, or a salt, a stereoisomer, or a deuterated form thereof, wherein the leaving group is

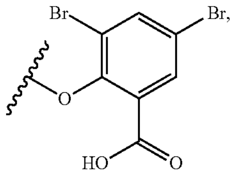
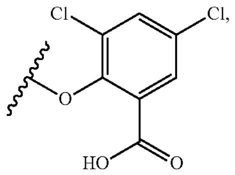
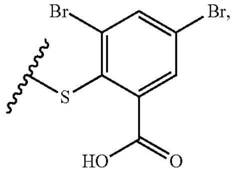
or
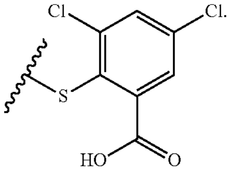

8. The compound of embodiment 1, or a salt, a stereoisomer, or a deuterated form thereof, wherein $R^1$ and $R^2$ are a leaving group, and wherein the leaving group is —O—($C_{1-6}$ alkylene)-$SO_3H$.
9. The compound of embodiment 8, or a salt, a stereoisomer, or a deuterated form thereof, wherein the leaving group is —O—($CH_2CH_2$)—$SO_3H$.
10. The compound of any one of embodiments 1-9, or a salt, a stereoisomer, or a deuterated form thereof, wherein X is $C_{1-12}$ alkylene, $C_{2-12}$ alkenylene, or $C_{2-12}$ alkynylene, each of which is optionally substituted with 1-6 $R^3$ as permitted by valency.
11. The compound of any one of embodiments 1-10, or a salt, a stereoisomer, or a deuterated form thereof, wherein X is $C_{1-6}$ alkylene, $C_{2-6}$ alkenylene, or $C_{2-6}$ alkynylene, each of which is optionally substituted with 1 or 2 $R^3$ as permitted by valency.
12. The compound of any one of embodiments 1-11, or a salt, a stereoisomer, or a deuterated form thereof, wherein X is $C_{1-6}$ alkylene optionally substituted with 1 or 2 $R^3$ as permitted by valency.
13. The compound of embodiment 12, or a salt, a stereoisomer, or a deuterated form thereof, wherein X is

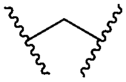
,
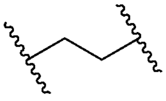
,
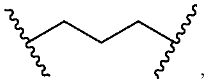
,

-continued

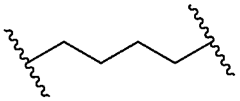
,
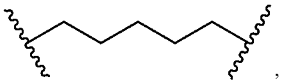
, or
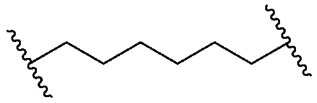
.

14. The compound of embodiment 12, or a salt, a stereoisomer, or a deuterated form thereof, wherein X is $C_{1-6}$ alkylene substituted with —S—($C_{1-6}$ alkylene)-$(OCH_2CH_2)_m$—$(CH_2)_n$—$N_3$, and wherein m is an integer of 1-50, and n is an integer of 0-25.
15. The compound of embodiment 12 or 14, or a salt, a stereoisomer, or a deuterated form thereof, wherein X is

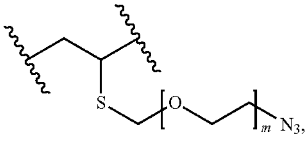

and wherein m is an integer of 1-25.
16. The compound of embodiment 12, 14, or 15, or a salt, a stereoisomer, or a deuterated form thereof, wherein X is

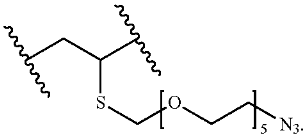

17. The compound of any one of embodiments 1-11, or a salt, a stereoisomer, or a deuterated form thereof, wherein X is $C_{2-6}$ alkenylene optionally substituted with 1 or 2 $R^3$ as permitted by valency.
18. The compound of embodiment 17, or a salt, a stereoisomer, or a deuterated form thereof, wherein X is

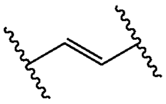
or
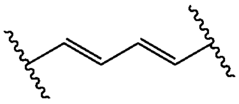
.

19. The compound of any one of embodiments 1-11, or a salt, a stereoisomer, or a deuterated form thereof, wherein X is $C_{2-6}$ alkynylene optionally substituted with 1 or 2 $R^3$ as permitted by valency.
20. The compound of embodiment 19, or a salt, a stereoisomer, or a deuterated form thereof, wherein X is

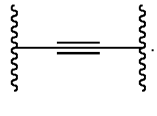

21. The compound of any one of embodiments 1-9, or a salt, a stereoisomer, or a deuterated form thereof, wherein X is $C_{3-9}$ cycloalkylene, $C_{3-9}$ cycloalkenylene, or 5-12 membered heterocyclylene, each of which is optionally substituted with 1 or 2 $R^3$ as permitted by valency.

22. The compound of embodiment 21, or a salt, a stereoisomer, or a deuterated form thereof, wherein X is $C_{3-7}$ cycloalkylene optionally substituted with 1 or 2 $R^3$ as permitted by valency.

23. The compound of embodiment 21 or 22, or a salt, a stereoisomer, or a deuterated form thereof, wherein X is

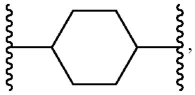,
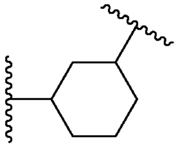, or
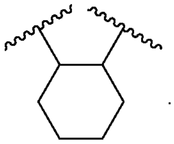.

24. The compound of embodiment 21, or a salt, a stereoisomer, or a deuterated form thereof, wherein X is $C_{3-7}$ cycloalkenylene optionally substituted with 1 or 2 $R^3$ as permitted by valency.

25. The compound of embodiment 21 or 24, or a salt, a stereoisomer, or a deuterated form thereof, wherein X is

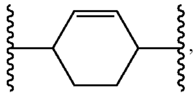,
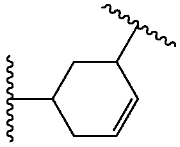,
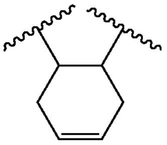,
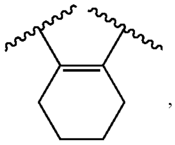, or
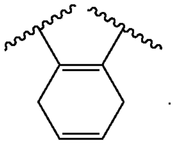.

26. The compound of embodiment 24, or a salt, a stereoisomer, or a deuterated form thereof, wherein X is $C_{3-7}$ cycloalkenylene substituted with —($C_{1-6}$ alkylene)-$N_3$.

27. The compound of embodiment 21 or 26, or a salt, a stereoisomer, or a deuterated form thereof, wherein X is

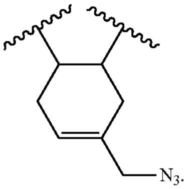 [SMILES: *C1CC=C(CN=[N+]=[N-])CC1*]

28. The compound of embodiment 21, or a salt, a stereoisomer, or a deuterated form thereof, wherein X is a 5-12 membered heterocyclylene containing a heteroatom which is S or O, and wherein the heterocyclylene is optionally substituted with —($C_{1-6}$ alkylene)-$N_3$.

29. The compound of embodiment 21 or 28, or a salt, a stereoisomer, or a deuterated form thereof, wherein X is

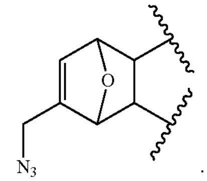.

30. The compound of any one of embodiments 1-9, or a salt, a stereoisomer, or a deuterated form thereof, wherein X is arylene or heteroarylene, each of which is optionally substituted with 1 or 2 $R^3$ as permitted by valency.

31. The compound of embodiment 30, or a salt, a stereoisomer, or a deuterated form thereof, wherein X is $C_{6-10}$ arylene optionally substituted with 1 or 2 $R^3$ as permitted by valency.

32. The compound of embodiment 30 or 31, or a salt, a stereoisomer, or a deuterated form thereof, wherein X is

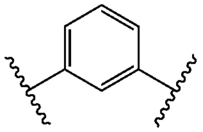 or
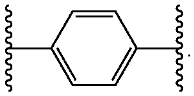.

33. The compound of embodiment 30 or 31, or a salt, a stereoisomer, or a deuterated form thereof, wherein X is $C_{6-10}$ arylene substituted with —C(O)—$R^1$, and wherein $R^1$ is —OH, halogen, or a leaving group.

34. The compound of embodiment 33, or a salt, a stereoisomer, or a deuterated form thereof, wherein $R^1$ is a leaving group.

35. The compound of embodiment 34, or a salt a stereoisomer, or a deuterated form thereof, wherein the leaving group is

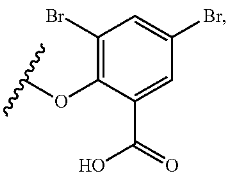,
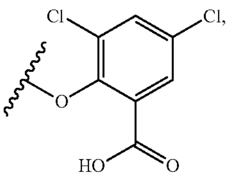,

-continued

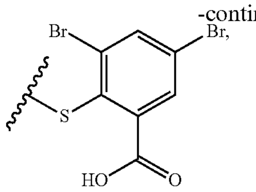

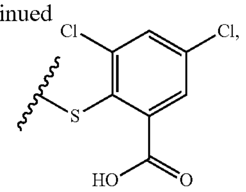

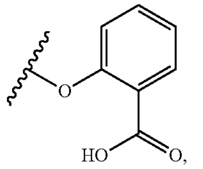

or

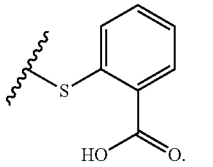

36. The compound of embodiment 33, 34, or 35, or a salt, a stereoisomer, or a deuterated form thereof, wherein X is

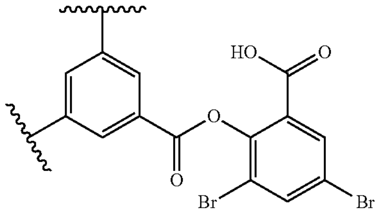

or

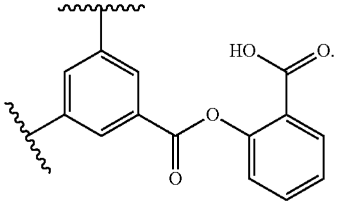

37. The compound of embodiment 30 or 31, or a salt, a stereoisomer, or a deuterated form thereof, wherein X is $C_{6-10}$ arylene substituted with —C(O)NH—($C_{1-12}$ alkylene)-($OCH_2CH_2)_m$—$(CH_2)_n$—$N_3$, or —NHC(O)—($C_{1-12}$ alkylene)-$(OCH_2CH_2)_m$—$(CH_2)_n$—$N_3$, and wherein each m is independently an integer of 1-200, and each n is independently an integer of 0-100.

38. The compound of embodiment 37, or a salt, a stereoisomer, or a deuterated form thereof, wherein X is $C_{6-10}$ arylene substituted with —C(O)NH—($C_{1-6}$ alkylene)-$(OCH_2CH_2)_m$—$N_3$, and wherein m is an integer of 2-50.

39. The compound of embodiment 38, or a salt, a stereoisomer, or a deuterated form thereof, wherein X is

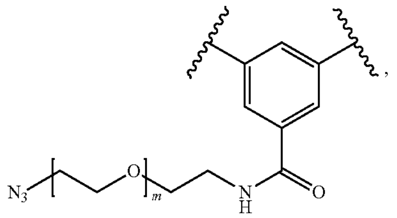

and wherein m is 4 or 9.

40. The compound of embodiment 37, or a salt, a stereoisomer, or a deuterated form thereof, wherein X is $C_{6-10}$ arylene substituted with —NHC(O)—($C_{1-6}$ alkylene)-$(OCH_2CH_2)_m$—$N_3$, and wherein m is an integer of 2-50.

41. The compound of embodiment 40, or a salt, a stereoisomer, or a deuterated form thereof, wherein X is

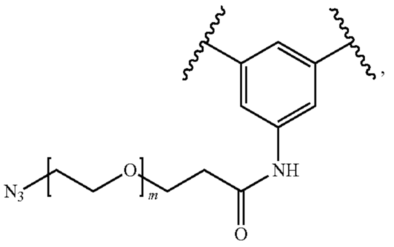

and wherein m is 4 or 9.

42. The compound of any one of embodiments 1-9, or a salt, a stereoisomer, or a deuterated form thereof, wherein X is -$L^1$-$NR^A$-$L^2$-, and wherein:

$R^A$ is H, —$C_{1-6}$ alkyl, aryl, —C(O)-aryl, —$SO_2$($C_{1-6}$ alkyl), —$SO_2$-aryl, or —($C_{1-12}$ alkylene)-$(OCH_2CH_2)_m$—$(CH_2)$—$N_3$, wherein m is an integer of 1-50, n is an integer of 0-25, and each alkyl, aryl, or alkylene is optionally and independently substituted with —$C_{1-6}$ alkyl; and $L^1$ and $L^2$ are each independently $C_{1-6}$ alkylene, $C_{2-6}$ alkenylene, $C_{2-6}$ alkynylene, $C_{3-6}$ cycloalkylene, $C_{3-6}$ cycloalkenylene, arylene, or heteroarylene, wherein $L^1$ and $L^2$ are optionally and independently substituted with 1-3 $R^3$.

43. The compound of embodiment 42, or a salt, a stereoisomer, or a deuterated form thereof, wherein $R^A$ is H, and $L^1$ and $L^2$ are each independently $C_{1-6}$ alkylene or $C_{2-6}$ alkenylene.

44. The compound of embodiment 42 or 43, or a salt, a stereoisomer, or a deuterated form thereof, wherein X is

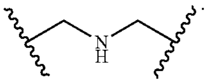 [SMILES: *CNC*]

45. The compound of embodiment 42, or a salt, a stereoisomer, or a deuterated form thereof, wherein $R^A$ is $C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl.

46. The compound of embodiment 42 or 45, or a salt, a stereoisomer, or a deuterated form thereof, wherein X is

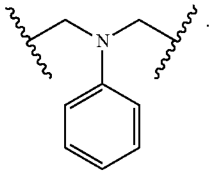 [SMILES: *CN(C*)c1ccccc1]

47. The compound of embodiment 42, or a salt, a stereoisomer, or a deuterated form thereof, wherein $R^A$ is —$SO_2$—$C_{1-6}$ alkyl, and $L^1$ and $L^2$ are each independently $C_{1-6}$ alkylene, or $C_{2-6}$ alkenylene.

48. The compound of embodiment 42 or 47, or a salt, a stereoisomer, or a deuterated form thereof, wherein X is

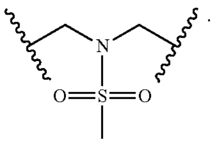 [SMILES: *CN(C*)S(C)(=O)=O]

49. The compound of embodiment 42, or a salt, a stereoisomer, or a deuterated form thereof, wherein $R^A$ is —$SO_2$—$C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl.

50. The compound of embodiment 42 or 49, or a salt, a stereoisomer, or a deuterated form thereof, wherein X is

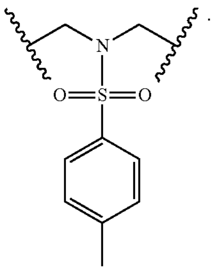 [SMILES: *CN(C*)S(=O)(=O)c1ccc(C)cc1]

51. The compound of embodiment 42, or a salt, a stereoisomer, or a deuterated form thereof, wherein $R^A$ is —C(O)—$C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl.

52. The compound of embodiment 42 or 51, or a salt, a stereoisomer, or a deuterated form thereof, wherein X is

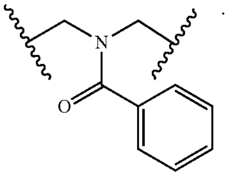

53. The compound of embodiment 42, or a salt, a stereoisomer, or a deuterated form thereof, wherein $R^A$ is —($C_{1-6}$ alkylene)-$(OCH_2CH_2)_m$—$(CH_2)_n$—$N_3$, and $L^1$ and $L^2$ are each independently $C_{1-6}$ alkylene, or $C_{2-6}$ alkenylene, wherein m is an integer of 1-50, and n is an integer of 0-25.

54. The compound of embodiment 42 or 53, wherein X is

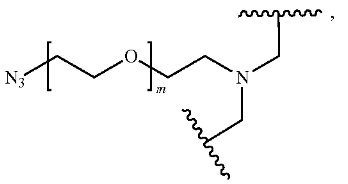

and m is 3.

55. The compound of embodiment 1, wherein the compound is:

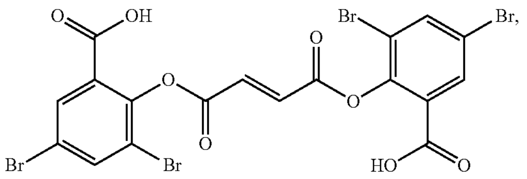

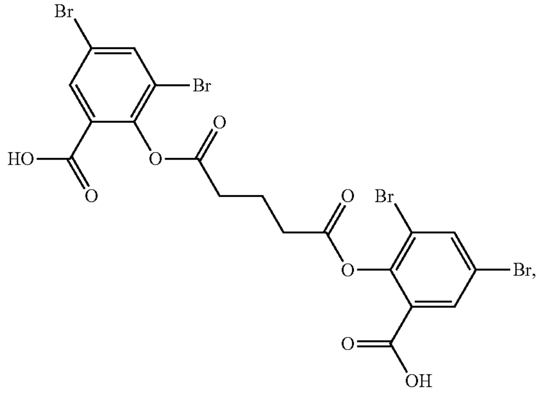

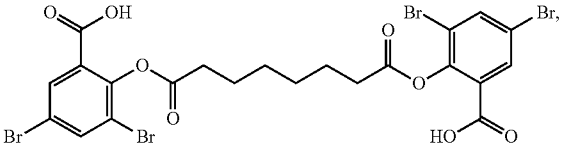

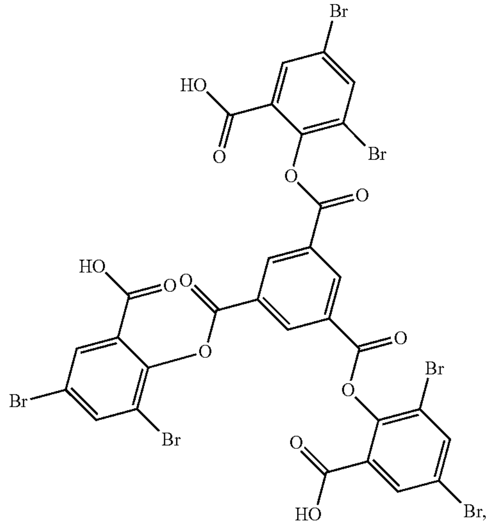

-continued
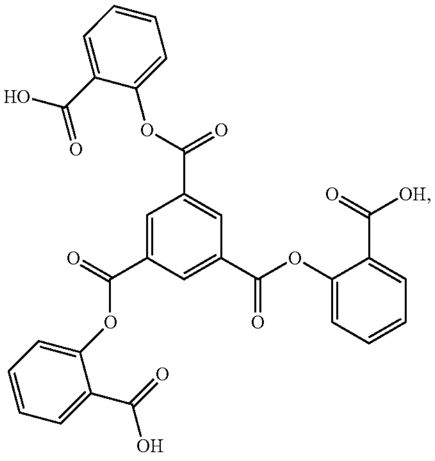
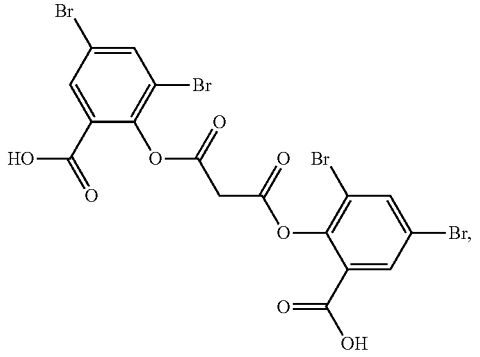
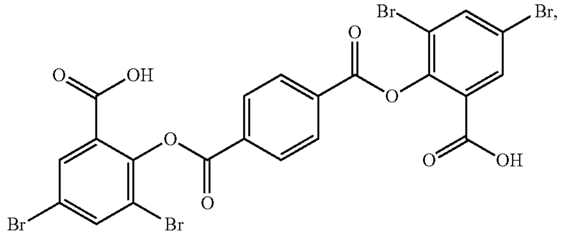
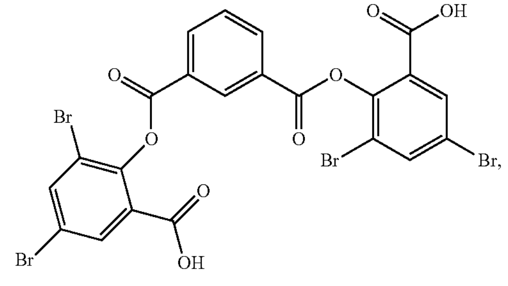
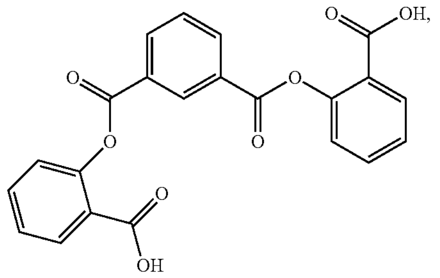
-continued
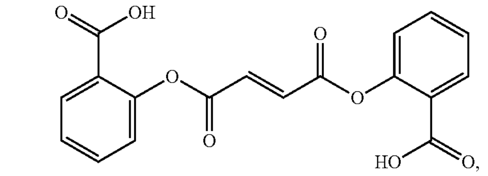
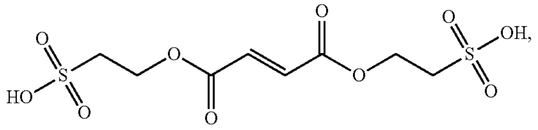
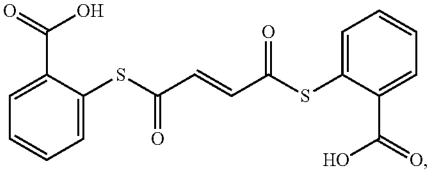
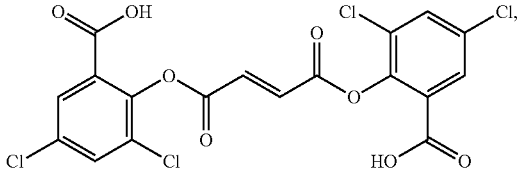
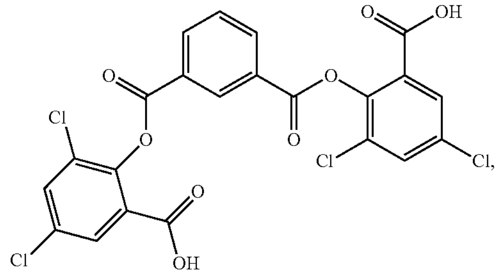
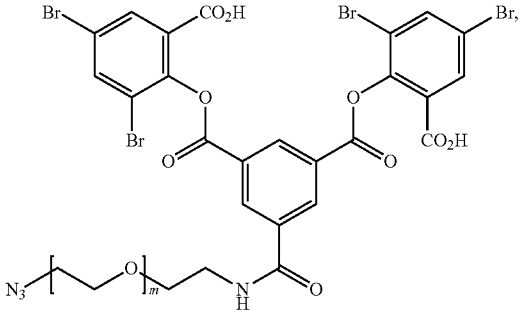
m = 4
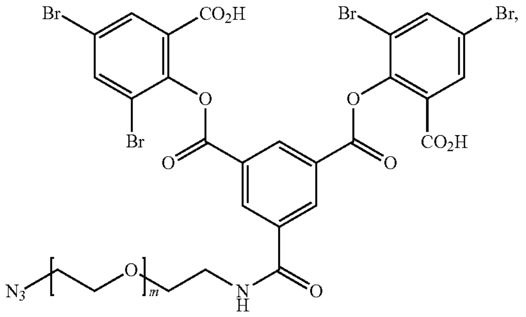
m = 9

-continued
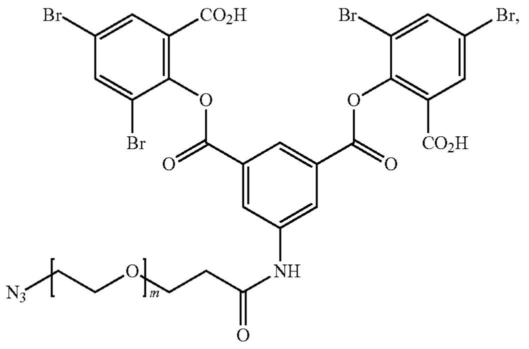
m = 4
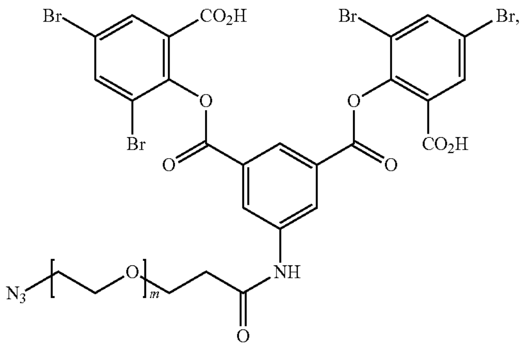
m = 9
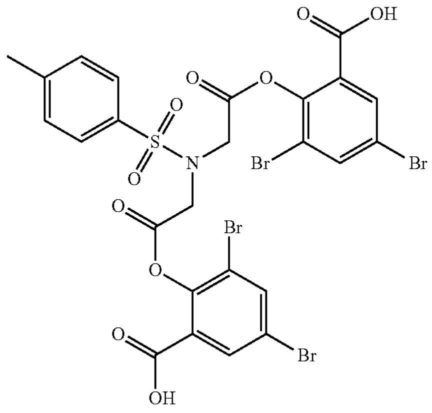
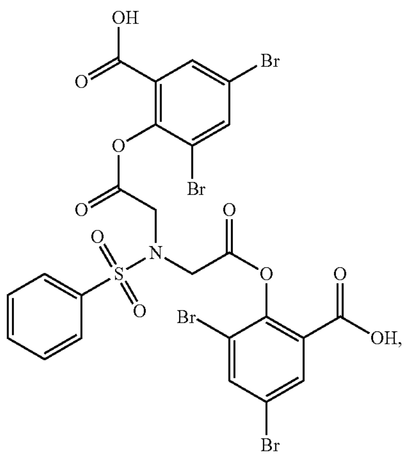
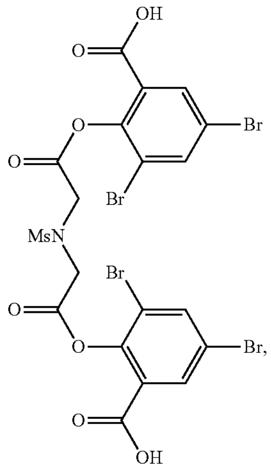
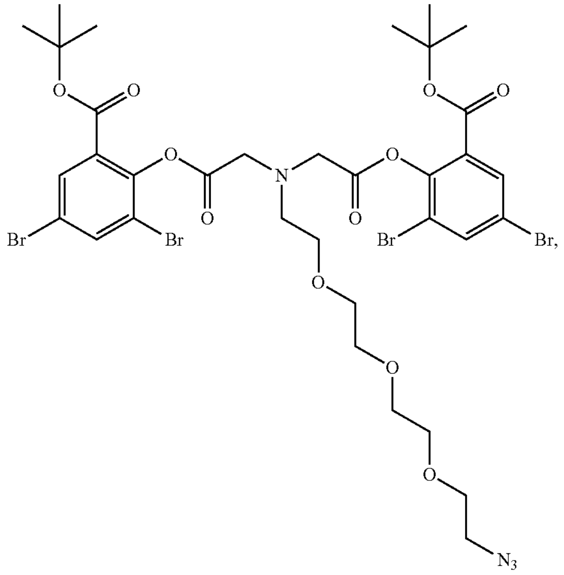
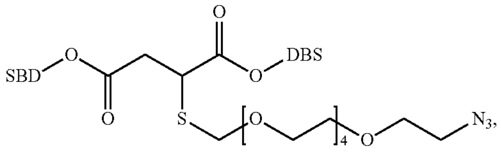
or
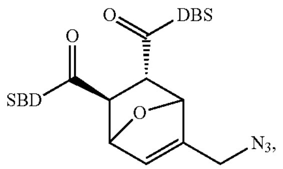
or a salt, a stereoisomer, or a deuterated form thereof, wherein DBS represents
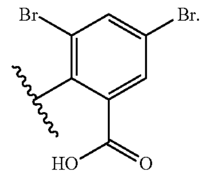 [SMILES: *c1c(Br)cc(Br)cc1C(=O)O]

56. A conjugated composition, comprising a reacted unit of a molecule and a compound of any one of embodiments 1-55, or a salt, a stereoisomer, or a deuterated form thereof.

57. The conjugated composition of embodiment 56, which is obtained by crosslinking the molecule with the compound of any one of embodiments 1-55, or a salt, a stereoisomer, or a deuterated form thereof.

58. The conjugated composition of embodiment 56 or 57, wherein the molecule is a protein.

59. The conjugated composition of embodiment 58, wherein the protein has two or more lysine residues, and the conjugated composition is obtained by cross-linking two or more lysine residues of the protein with the compound of any one of embodiments 1-55, or a salt, a stereoisomer, or a deuterated form thereof.

EXAMPLES

The present disclosure is further illustrated by reference to the following Examples. However, it should be noted that these Examples, like the embodiments described above, are illustrative and are not to be construed as restricting the scope of the disclosure in any way.

In embodiments, compounds of the present disclosure can be synthesized using the following methods. General reaction conditions are given, and reaction products can be purified by generally known methods including silica gel chromatography using various organic solvents such as hexane, dichloromethane, ethyl acetate, methanol and the like or preparative reverse phase high pressure liquid chromatography.

Example 1: Synthesis of bis(3,5-dibromosalicyl)glutarate (DBSG)

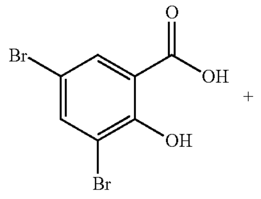

3,5-dibromosalicylic acid

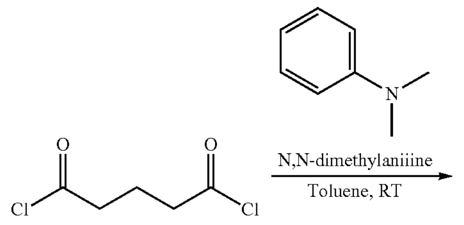

glutaryl dichloride

-continued

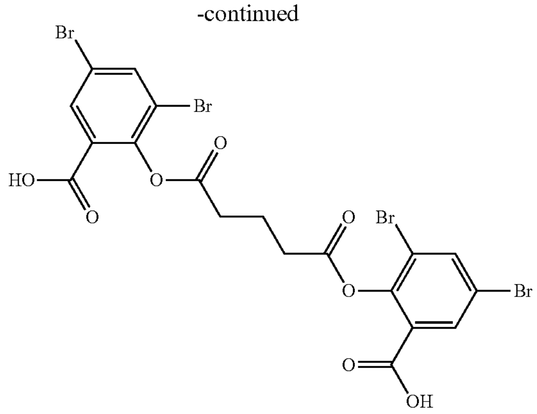

DBSG

To a 250 mL round bottomed flask equipped with a stirrer bar was added glutaryl dichloride (4.23 g, 0.02 g mmol) in dry toluene (100 mL). 3,5-dibromosalicylic acid (15.09 g, 0.051 mmol) and N,N-dimethylaniline (12 g, 0.1 mol) was added and the mixture was stirred at 25° C. for 3 hours. Water (30 mL) and concentrated HCl (7 mL) was added, and the combination was stirred at RT for 20 minutes. The precipitate was filtered under vacuum and recrystallised from 1:1 ethyl acetate:methyl tert-Butyl Ether (MTBE) to yield an off-white solid as DBSG product.

Example 2: Synthesis of bis(3,5-dibromosalicyl)malonate (DBSM)

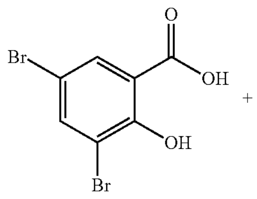

3,5-dibromosalicylic acid

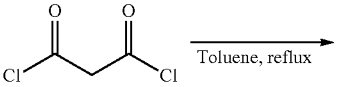

malonyl chloride

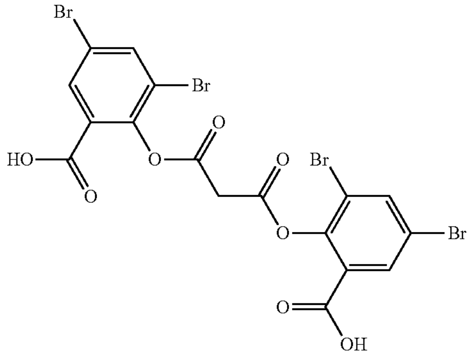

DBSM

To a 100 mL round bottomed flask equipped with a stirrer bar was added 3,5-dibromosalicylic acid (2 g, 0.0064 mol) in dry toluene (45 mL). The solution was heated to reflux.

The solution was cooled to room temperature before a solution of malonyl chloride (0.9 g, 0.0064 mol) in toluene (5 mL) was added and the combination was refluxed for 24 hours. The mixture was cooled to room temperature and the product was filtered and washed with toluene. The crude product was recrystallised from 1:1 ethyl acetate:toluene to yield a light brown solid as DBSM product.

Example 3: Synthesis of bis(3,5-dibromosalicyl)terephthalate (DBST)

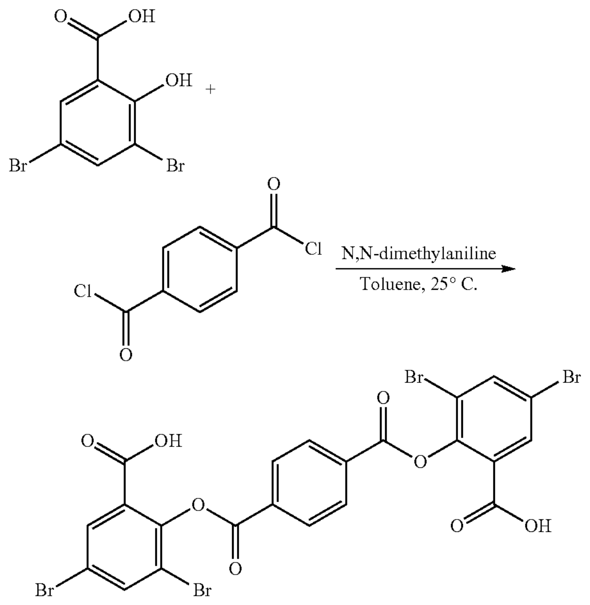

DBST

To a 100 mL round bottomed flaks was added terephthaloyl chloride (2.03 g, 0.01 mol) and dry toluene (50 mL). 3,5-dibromosalicylic acid (5.92 g, 0.02 mol) and N,N-dimethylaniline (4.85 g, 0.04 mol) and the mixture was stirred at 25° C. for 3 hours. Water (30 mL) and concentrated HCl (4 mL) was added and the mixture was stirred for 20 minutes and filtered. The filtrate was extracted, and the organic layer was dried with $MgSO_4$, concentrated and combined with the solid filtered before. The crude product was recrystallised with acetone:water (2:1) to yield an off-white solid as DBST product.

Example 4: Synthesis of bis(3,5-dibromosalicyl)fumarate (DBSF)

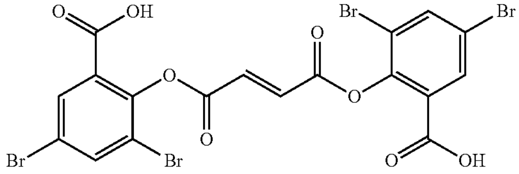

DBSF

To a 3-necked 100 mL round bottomed flask equipped with a stirrer bar was added 3,5-dibromo-2-hydroxybenzoic acid (3.776 g, 12.76 mmol) and N,N-dimethylaniline (3.213 mL, 25.3 mmol) in dry toluene (50 mL) at 0° C. under a flow of $N_2$. The mixture was warmed to RT before fumaroyl dichloride (0.675 ml, 6.24 mmol) was added dropwise. The reaction was stirred overnight under $N_2$. The reaction mixture was reverse quenched by dropwise addition into 0.05 M HCl (15 mL). A precipitate started to form on quenching. The mixture was stirred for 15 minutes before the precipitate was filtered off. The filter cake was washed with water (10 mL) and toluene (10 mL) and pulled to dryness. The crude product was purified via recrystallisation twice with water: acetone 1:1 (5 volumes) to yield DBSF product. Quantitative $^1$H-NMR showed a purity of 93% using tetrachloronitrobenzene as an internal standard.

Example 5: Synthesis of di-bromo-salicyl-subarate (DBSS)

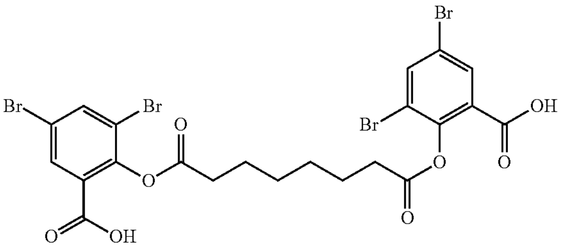

DBSS

To a 3-necked 100 mL round bottomed flask equipped with a stirrer bar was added 3,5-dibromo-2-hydroxybenzoic acid (3.776 g, 12.76 mmol) and N,N-dimethylaniline (3.213 ml, 25.3 mmol) in dry toluene (50 ml) at 0° C. under a flow of $N_2$. The mixture was warmed to RT before decanedioyl dichloride (1.502 ml, 7.03 mmol) was added dropwise. The reaction was stirred overnight under $N_2$. The reaction mixture was reverse quenched by dropwise addition into 0.05 M HCl (15 mL). A precipitate started to form on quenching. The mixture was stirred for 15 minutes before the precipitate was filtered off. The filter cake was washed with water (10 ml) and toluene (10 mL) and pulled to dryness. The crude product was purified via recrystallisation twice with water: acetone 1:1 (5 volumes) to yield DBSS product. Quantitative $^1$H-NMR showed a purity of 92% using tetrachloronitrobenzene as an internal standard.

Example 6: Synthesis of trimesoyltris(1-(tert-butoxycarbonyl)-3,5-dibromosalicylate (TTDS)

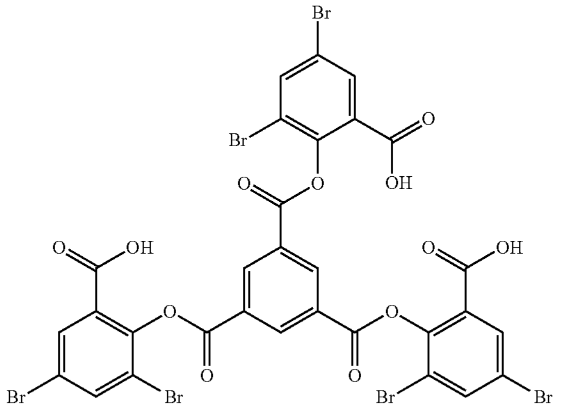

TTDS

Synthesis Method 1 of TTDS

Synthesis method 1 of TTDS was designed based on literature procedures (Delaney et al., *Arch. Biochem. Biophys.,* 1984, 228, 627; Kluger et al., J. Am. Chem. Soc., 1992, 114, 9276).

Step 1. Protection of 3,5-dibromosalicylate

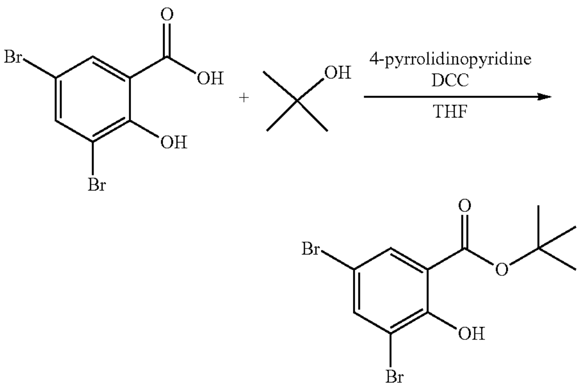

To a 250 mL round bottomed flask equipped with a stirrer bar was added 3,5-dibromosalicylic acid (Fluorochem, 2 g, 6.76 mmol) and 4-pyrrolidinopyridine (40 mg, 0.27 mmol) in dry t-butanol (50 mL). To this stirred suspension was slowly added a solution of DCC (N,N-dicyclohexylcarbodiimide, 1.464 g) in anhydrous THF (10 mL). The reaction was stirred at room temperature under nitrogen and monitored by TLC (3:1 heptane:EtOAc+0.1% TFA) for 2 hours before being concentrated to a residue by rotary evaporation. The residue was taken up in diethyl ether (80 mL) and heated to 40° C. Oxalic acid (1 g) was added portionwise to the stirred solution. The mixture was cooled to room temperature and the precipitates filtered off under vacuum. The filtrate was concentrated in vacuo to yield 1.45 g of crude off-white solid which was used without any further purification.

Step 2. Synthesis of trimesoyltris(1-(tert-butoxycarbonyl)-3,5-dibromosalicylate

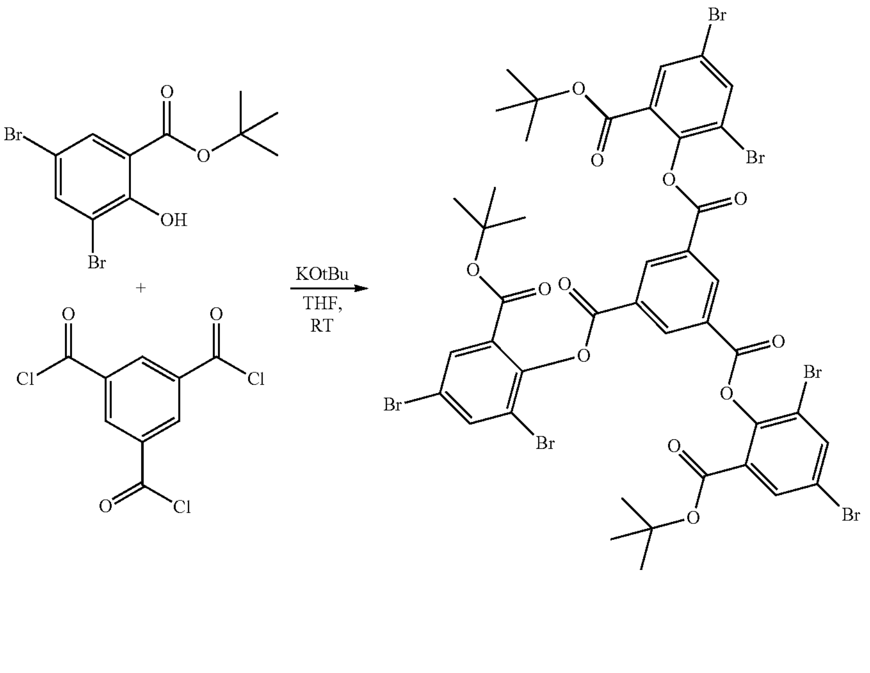

To a 250 mL round bottomed flask was added crude tert-butyl-3,5-dibromosalicylate from step 1 and anhydrous THF (60 mL). Potassium tert-butoxide (4.38 mmol, added as a 1 M solution in THF, Sigma-Aldrich) was added and the mixture stirred at room temperature for 15 minutes. A solution of trimesoyl trichloride (Apollo Scientific, 0.38 g, 1.46 mmol) in anhydrous THF (10 mL) was added dropwise over 15 minutes. The reaction mixture was stirred overnight at room temperature and followed by TLC (3:1 heptane: EtOAc). Diethyl ether (30 mL) was added and the organic washed with 2×30 mL portions of water. The material was dried with $MgSO_4$, filtered under vacuum and the filtrate was concentrated in vacuo to yield 1.5 g of off-white solid which was used in the next synthetic step without any further purification. $^1$H-NMR analysis is consistent with desired product.

Step 3. Deprotection of trimesoyltris(1-(tert-butoxycarbonyl)-3,5-dibromosalicylate

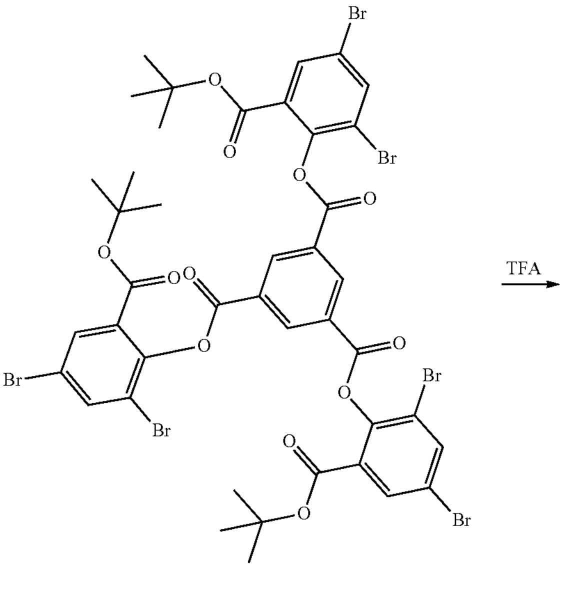

-continued

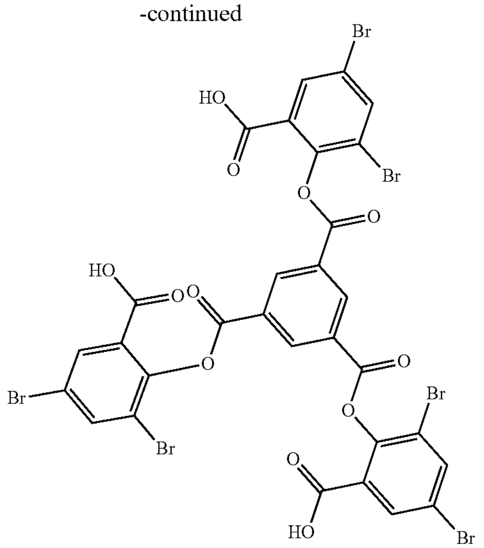

TTDS

To a 100 mL round bottomed flask was added crude material from step 2. Anhydrous trifluoroacetic acid (40 mL) was added slowly with stirring and the material was held at room temperature for 1 hour. The material was cooled to 0-5° C. and cold diethyl ether (40 mL) was added slowly and the whole held around 5° C. for 6 hours. The crystals formed were filtered off, dried under vacuum to yield TTDS (1.4 g) as an off-white solid.

Synthesis Method 2 of TTDS

Synthesis method 2 of TTDS was designed based on literature procedures (Delaney et al., *Arch. Biochem. Biophys.,* 1984, 228, 627; Kluger et al., J. Am. Chem. Soc., 1992, 114, 9276).

Step 1. Protection of 3,5-dibromosalicylate

To a 1 L round bottomed flask equipped with a stirrer bar was added 3,5-dibromosalicylic acid (Fluorochem, 20 g, 67.6 mmol) and 4-pyrrolidinopyridine (400 mg, 1.35 mmol) in dry t-butanol (500 mL). To this stirred suspension was slowly added a solution of DCC (N,N-dicyclohexylcarbodiimide, 14.64 g) in anhydrous THF (100 mL). The reaction was stirred at room temperature under nitrogen for 2 hours and followed by TLC (3:1 heptane:EtOAc+0.1% TFA) before being concentrated to a residue by rotary evaporation. The residue was taken up in diethyl ether (400 mL) and heated to 40° C. Oxalic acid (10 g) was added portionwise to the stirred solution. The mixture was cooled to room temperature and the precipitates filtered off under vacuum. The filtrate was concentrated in vacuo to yield 23.7 g of crude off-white solid which was used without any further purification.

Step 2. Synthesis of trimesoyltris(1-(tert-butoxycarbonyl)-3,5-dibromosalicylate To a 2 L round bottomed flask was added crude tert-butyl-3,5-dibromosalicylate from step 1 and anhydrous THF (600 mL). Potassium tert-butoxide (67.3 mmol, added as a 1 M solution in THF, Sigma-Aldrich) was added and the mixture stirred at room temperature for 15 minutes. A solution of trimesoyl trichloride (Apollo Scientific, 5.96 g, 22.4 mmol) in anhydrous THF (200 mL) was added dropwise over 15 minutes. The reaction mixture was stirred overnight at room temperature and followed by TLC (3:1 heptane:EtOAc). Diethyl ether (500 mL) was added and the organic washed with 2×400 mL portions of water. The material was dried with $MgSO_4$, filtered under vacuum and the filtrate was concentrated in vacuo to yield 21.8 g of off-white solid which was used in the next synthetic step without any further purification. $^1$H-NMR analysis is consistent with desired product.

Step 3. Deprotection of TTDS

To a 1 L round bottomed flask was added crude material from step 2. Anhydrous trifluoroacetic acid (800 mL) was added slowly with stirring and the material was held at room temperature for 1 hour. The material was cooled to 0-5° C. and cold diethyl ether (200 mL) was added slowly and the whole held around 5° C. for 6 hours. The crystals formed were filtered off, dried under vacuum to yield TTDS (10.8 g) as an off-white solid.

Synthesis of Protected tBu-DBS

To a 250 mL round bottomed flask equipped with a stirrer bar was added 3,5-dibromosalicylic acid (Fluorochem, 20 g, 6.76 mmol) and 4-pyrrolidinopyridine (400 mg, 0.27 mmol) in dry t-butanol (500 mL). To this stirred suspension was slowly added a solution of DCC (N,N-dicyclohexylcarbodiimide, 14.64 g) in anhydrous THF (100 mL). The reaction was stirred at room temperature under nitrogen for 2 hours before being concentrated to a residue by rotary evaporation. The residue was taken up in MTBE (800 mL) and heated to 40° C. Oxalic acid (10 g) was added portionwise to the stirred solution. The mixture was cooled to room temperature and the precipitates filtered off under vacuum. The filtrate was concentrated in vacuo to yield 21.9 g of crude off-white solid which was used without any further purification.

To a 100 mL round bottomed flask equipped with a stirrer bar was added 1 g crude tert-butyl-3,5-dibromosalicylate from LMD-0013E-077 and anhydrous THF (30 mL). Potassium tert-butoxide (2.84 mmol, added as a 1 M solution in THF or as a solid) was added and the mixture stirred at room temperature for 15 minutes. A solution of trimesoyl trichloride (0.251 g, 0.947 mmol) in anhydrous THF (10 mL) was added dropwise over 15 minutes. The reaction mixture was stirred overnight at room temperature. MTBE (50 mL) was added and the organic washed with 2×40 mL portions of water. The material was dried with $MgSO_4$, filtered under vacuum and the filtrate was concentrated in vacuo to yield a solid product which was analysed by $^1$H-NMR.

Synthesis Method 3 of TTDS (Direct Synthesis of TTDS Using $Et_3N$)

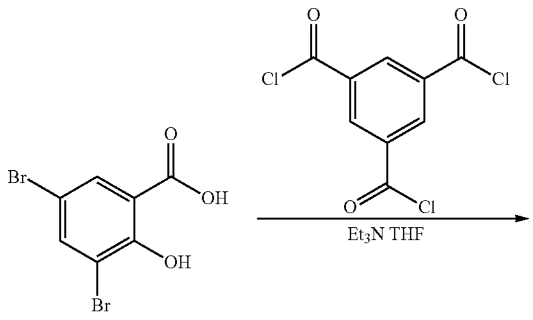

-continued

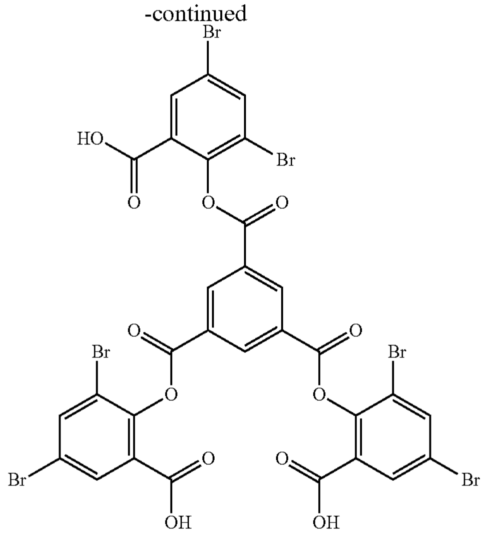

To a 100 mL round bottomed flask equipped with a stirrer bar was added 3,5-dibromosalicylic acid (1 g, 3.38 mmol) in anhydrous THE (40 mL). Triethylamine (0.942 mL, 6.76 mmol) was added in one portion. The flask was stirred for 15 minutes at room temperature before a solution of trimesoyl trichloride (Apollo scientific, bottle II, 0.3 g, 1.126 mmol) in anhydrous THF (10 mL) was added dropwise with stirring. The reaction was stirred overnight at room temperature before deionised water (10 mL) and concentrated HCl (1 mL) was added. The reaction was stirred for a further 1 hour before the precipitates formed were filtered off, dried under vacuum, and analysed by $^1$H-NMR. Overlay of the formed material and previously isolated TTDS shows some product formation but also several other peaks which have not yet been assigned.

Esterification of TTDS

The esterification of TTS was developed to protect the carboxy groups (B. Neises, W. Steglich, *Angew. Chem. Int. Ed.,* 1978, 17, 522-524).

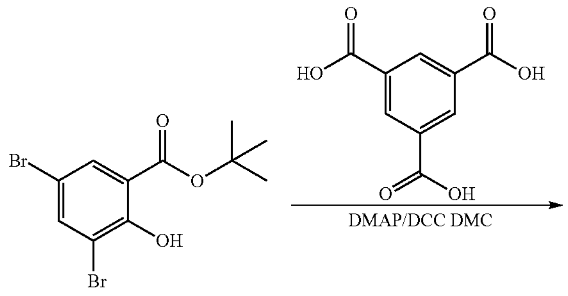

-continued

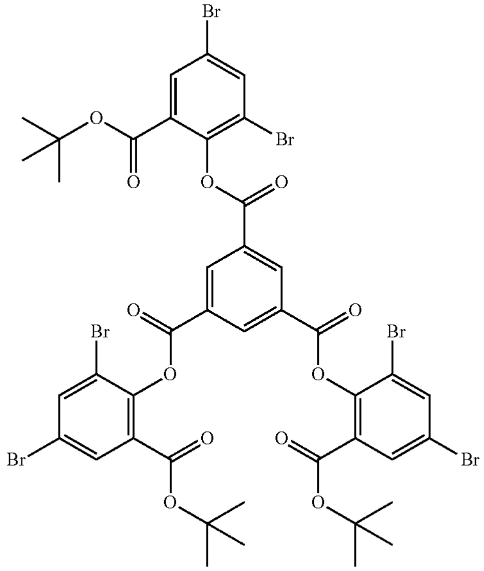

To a 100 mL round bottomed flask equipped with a stirrer bar was added trimesic acid (Sigma Aldrich, 280 mg, 1.19 mmol), dicyclohexylcarbodiimide (DCC, 3.3 eq, 0.736 g) and dimethylaminopyridine (DMAP, 24 mg, 5 mol %) in dichloromethane (25 mL). The reaction was stirred for 15 minutes at room temperature before a solution of t-Bu-protected 3,5-dibromosalicylic acid (LMD-0013E-077, 1.125 g) in DCM (10 mL) was added. The reaction mixture was stirred at room temperature for 3 hours before being washed with brine. The organic layer was dried over $MgSO_4$ and concentrated under vacuum to yield an off-white solid. Overlay of the formed material and previously isolated t-Bu protected TTDS shows some product formation.

Synthesis Method 4 of TTDS (Direct Synthesis of TTDS Using Dimethylaniline in Toluene)

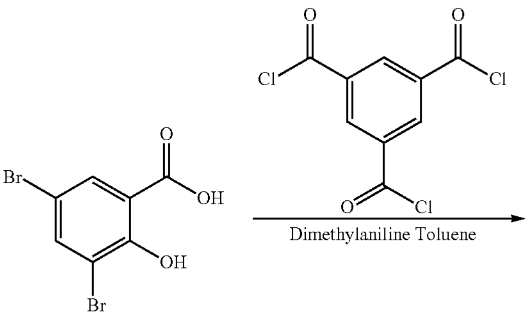

-continued

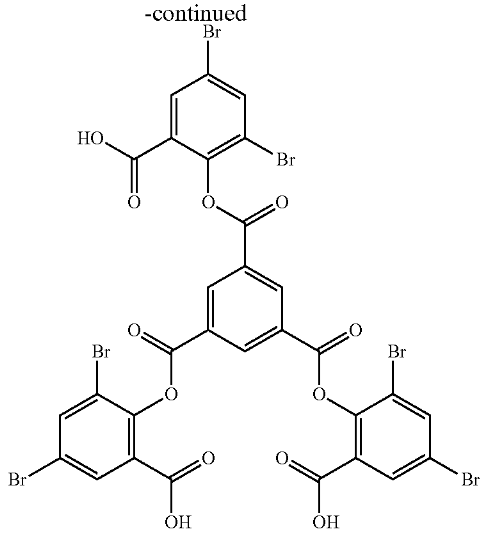

To a 4 mL glass vial equipped with a stirrer bar was added 3,5-dibromosalicylic acid (100 mg) in anhydrous toluene (1.5 mL). Dimethylaniline (55 mg, 6 eq.) was added and the mixture was stirred at 25° C. for 3 hours. Water (0.5 mL) and concentrated HCl (0.2 mL) was added and the mixture was stirred for 20 minutes and filtered. The filtrate was extracted and the organic layer was dried with $MgSO_4$, concentrated and combined with the solid filtered before. $^1$H-NMR shows TTDS product formation.

Synthesis Method 5 of TTDS (Direct Synthesis of TTDS Using $Et_3N$ and DMAP)

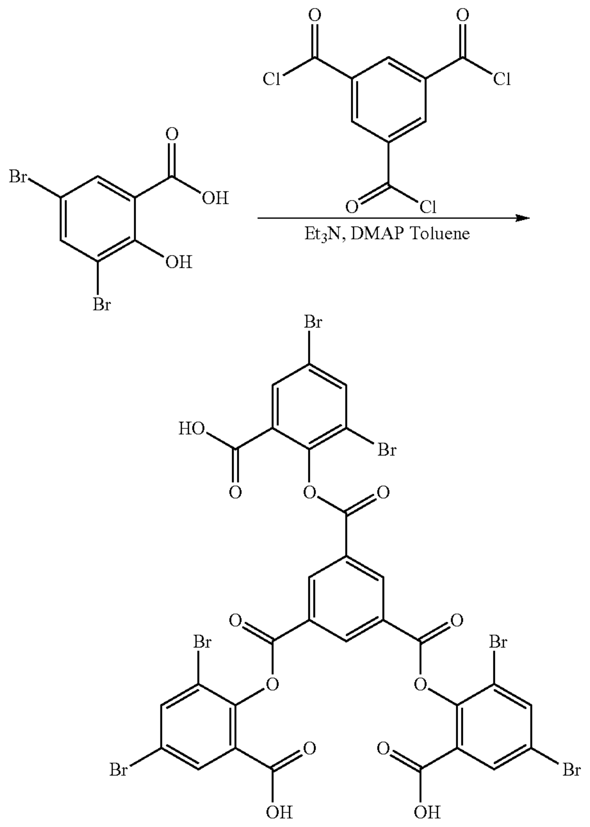

To a 4 mL glass vial equipped with a stirrer bar was added 3,5-dibromosalicylic acid (100 mg) in anhydrous toluene (1.5 mL). Triethylamine (94 µl, 6 eq.) and DMAP (2 mg, 5 mol %) was added and the mixture was stirred at 25° C. for 3 hours. Water (0.5 mL) and concentrated HCl (0.2 mL) was added and the mixture was stirred for 20 minutes and filtered. The filtrate was extracted and the organic layer was dried with $MgSO_4$, concentrated and combined with the solid filtered before. $^1$H-NMR shows TTDS product formation.

Synthesis Method 6 of TTDS (Oxidation of Aldehyde)

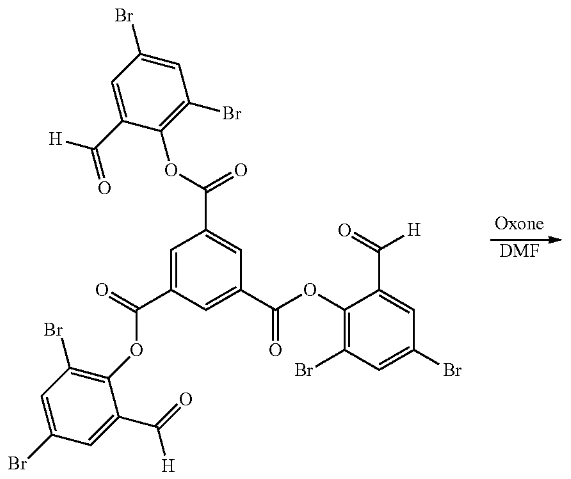

040-3

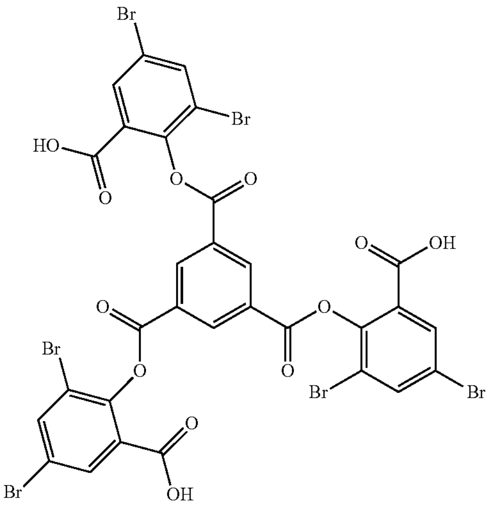

Oxone (236 mg, 384 umol) was added to the trialdehyde "040-3" (127 mg, 128 umol), triethyl orthoacetate (1.50 mL) and DMF (1.50 mL). The reaction was stirred for 5 h at rt. Then, the reaction poured into 50 mL EtOAc, washed with 1 M HCl (25 mL) and washed with (5×25 mL) dilute brine. Concentrated to about 15 mL then about 15 mL heptane was added and concentrated further. NMR analysis shows clean formation of TTDS. Triethyl orthoacetate was used as a water scavenger.

Example 7: Synthesis of trimesyl tris(salicylate) (TTS)

Step 1. Synthesis of Salicyl Aldehyde Benzene Triester

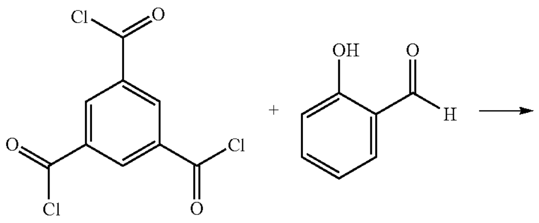

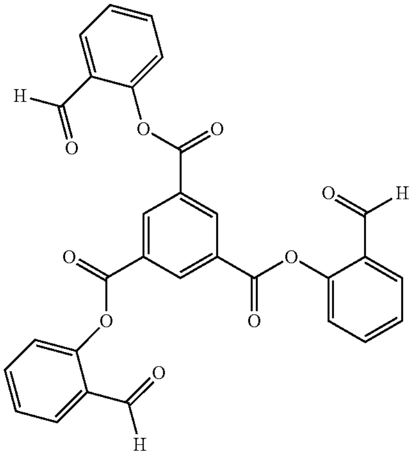

038-1

Potassium tert-butoxide (119 mg, 1.04 mmol) was added to a flask containing THF (3.15 mL) and salicylaldehyde (111 uL, 1.04 mmol). Color of the reaction mixture changed to yellow and precipitation (ppt) was formed. After 30 minutes, 1,3,5-benzenetricarbonyl trichloride (60.6 uL, 333 umol) was added. The reaction became yellow-brown and clearer. After 1.5 h, no starting material (SM) was observed on TLC. The reaction mixture was diluted with 20 mL EtOAc, washed with 20 mL 1 M HCl, water, brine, dried over sodium sulfate and concentrated to give 516 mg off-white solid. 28 mg was dissolved in EtOAc. Required boiling solvent to get the powder dissolved. The crude product was run on column 0-40% EtoAc in hexanes. Product crystallized as it came out of the nozzle. 14 mg product was recovered. Silica gel flash column chromatography was used to purify the rest of the mixture (0-40% EtOAc in hexanes).

Step 2. Oxidation of Salicyl Aldehyde Benzene Triester

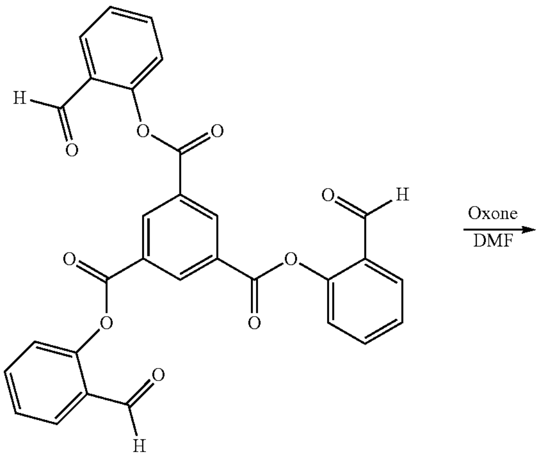

038-1

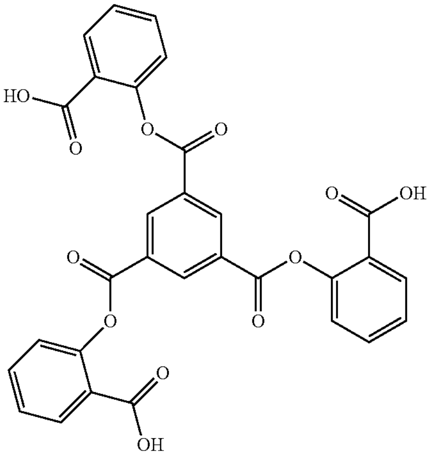

TTS

Oxone (3.57 g, 5.80 mmol) was added to salicyl aldehyde benzene triester "038-1" (1.01 g, 1.93 mmol) in DMF (40 mL) at room temperature (rt). The reaction mixture was stirred 10 h. The reaction mixture was worked up by addition of 150 mL of EtOAc, washed with 150 mL 1 M HCl, 4×10% brine (150 mL), and brine 50 mL, followed by dehydration with sodium sulfate, and concentration. NMR shows clean formation of TTS.

Example 8: Synthesis of bis(3,5-dibromosalicyl)isophthalate (DBSI)

Step 1

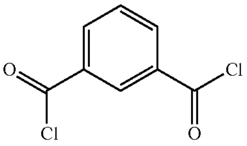

+

-continued

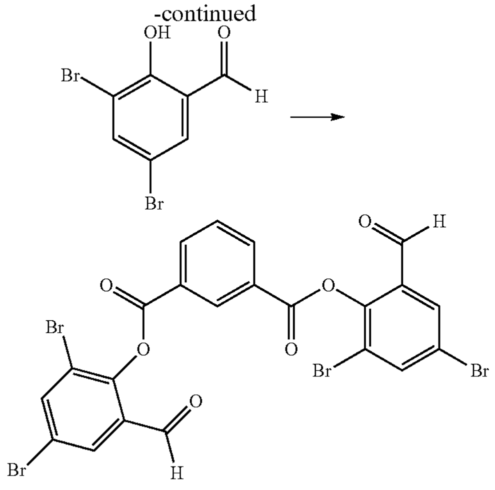

052

3,5-dibromosalicylaldehyde (3.30 g, 11.6 mmol) was added to THF (116 mL) followed by potassium t-butoxide (1.30 g, 11.6 mmol) at rt. Yellow precipitate was formed. Isophthaloyl chloride (1.34 mL, 5.78 mmol) was added to the reaction mixture and stirred overnight. TLC shows the reaction is complete. EtOAc (300 mL) was added. The reaction mixture was then washed with 50 mL 1 M HCl, 300 mL water, and 50 mL brine. Dried over sodium sulfate, concentrated, then a small amount of heptane was added and concentrated. Then placed under high vac for 30 min. NMR shows clean formation of the product 052.

Step 2

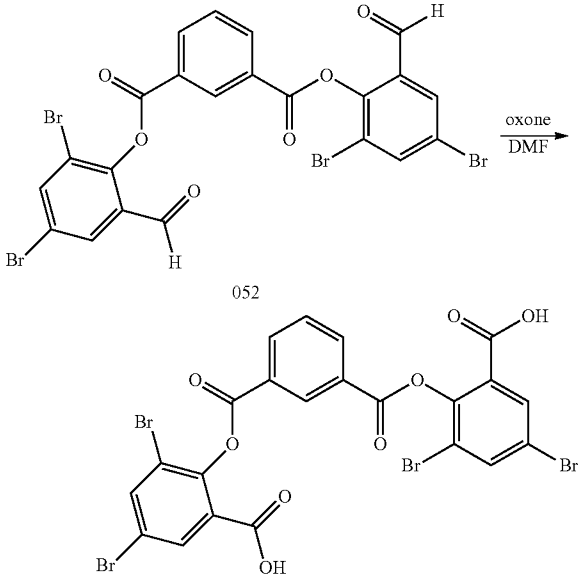

052

DBSI

Oxone (2.99 g, 4.87 mmol) was added to 052 (1.68 g, 2.44 mmol) in DMF (25 mL) at rt. TLC indicated reaction is complete after 3 h. Reaction mixture was diluted with 150 mL ethyl acetate, washed with 50 mL 1M HCl, then washed with 5×50 mL dilute brine then 50 mL brine. Dried with sodium sulfate, and concentrated using Hi-vac. Then, heptane was added and evaporated twice to give 1.47 g (84%) product DBSI.

Example 9: Synthesis of bis(salicyl)isophthalate (BSI)

Step 1. Salicyl-isophthalate

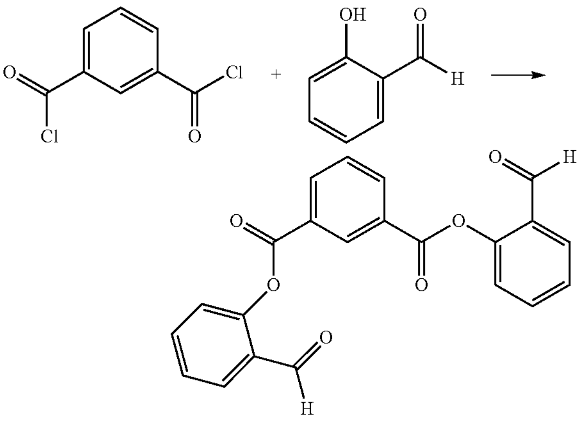

Potassium t-butoxide (1.12 g, 10.0 mmol) was added to salicylaldehyde (1.07 mL, 10.0 mmol) in THF (50.0 mL). Reaction mixture became yellow and precipitate was formed. After 1.5 h, TLC indicates completion of the reaction. 150 mL EtOAc was added to the reaction mixture. The reaction mixture was then washed with 25 mL 1M HCl, 50 mL water, 25 mL brine. Concentrated then placed under hi-vac. NMR shows clean formation of the product (salicyl isophthalate).

Step 2. Oxidation of salicyl-isophthalate

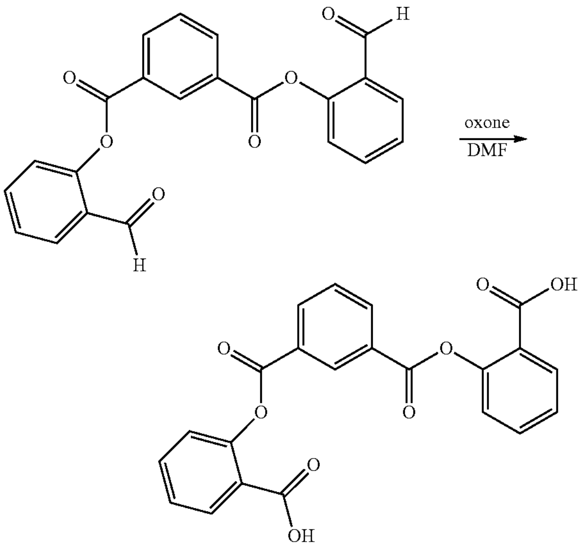

BSI

Potassium peroxymonosulfate (4.11 g, 6.68 mmol) was added to salicyl isophthalate (1.25 g, 3.34 mmol) in DMF (35 mL) at rt. After 4 h, the reaction was completed as indicated by TLC. 100 mL EtOAc was added to the reaction mixture, which was then washed with 1M HCl followed by 5×50 mL water, brine. The reaction mixture was dried over sodium sulfate and concentrated to afford product BSI (92% yield).

Example 10: Synthesis of bis-salicylfumerate (BSAF)

Step 1

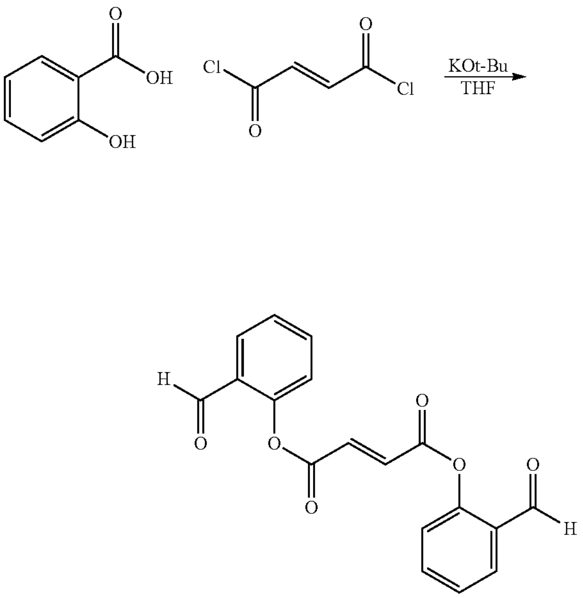

072

Potassium tert-butoxide (469 mg, 4.09 mmol) was added to salicylaldehyde (436 uL, 4.09 mmol) in THF (40 mL) at rt. After 15 minutes, fumaryl chloride (233 uL, 2.05 mmol) was added. The color of reaction mixture turned brown, and precipitation (ppt) was dissolved. After 4 h, TLC showed the reaction was completed. Worked up with HCL, water, brine, concentrated to give 509 mg of product 072 (77%).

Step 2

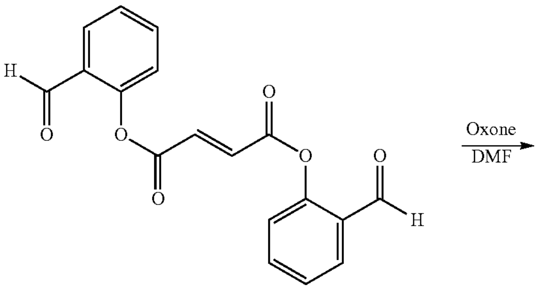

072

-continued

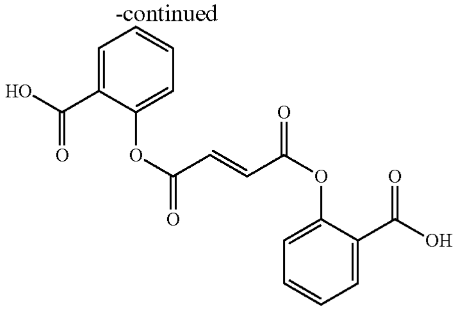

BSAF

Compound 072 (304 mg, 937 umol) and oxone (576 mg, 937 umol) were mixed in DMF (9 mL) at rt. After 4 h, TLC shows reaction complete. Extracted into ethyl acetate, washed with water, brine, dried over sodium sulfate and concentrated. 189 mg crude BSAF was collected after recrystallization. 95 mg BSAF was collected after second recrystallization.

Example 11: Synthesis of bis-thiosalicyl fumerate

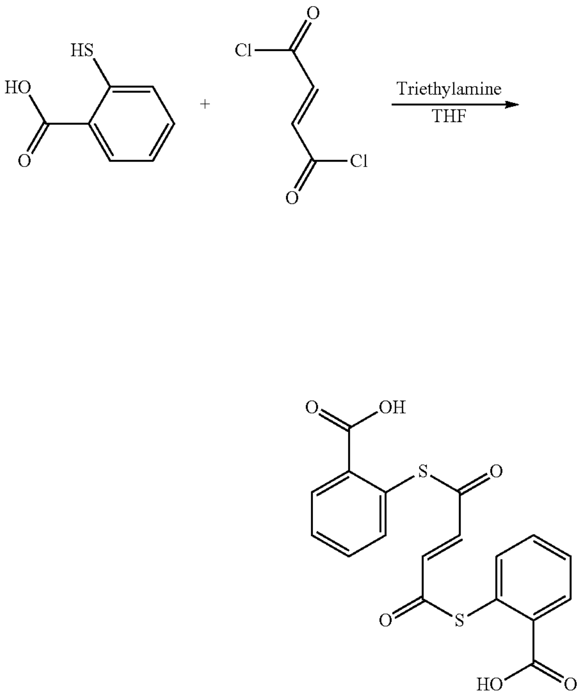

BTASF

Triethylamine (878 uL, 6.30 mmol) was added dropwise to thiosalicylic acid (0.971 g, 6.30 mmol) and fumaryl chloride (358 uL, 3.15 mmol) in THF (60 mL) at rt. Immediate precipitation (ppt) formed. After 20 min, TLC shows the reaction is done. The reaction mixture was taken up in ethyl acetate, washed with 1 M HCl, water, and brine, dried over sodium sulfate, and entreatedated to yield crude BTASF. The crude product was taken up in acetone and then filtered. BTASF was obtained as off-white solid (847 mg, 35%).

Example 12: Synthesis of Mesyl Iminodiacetic Acid (MIDA)

Step 1

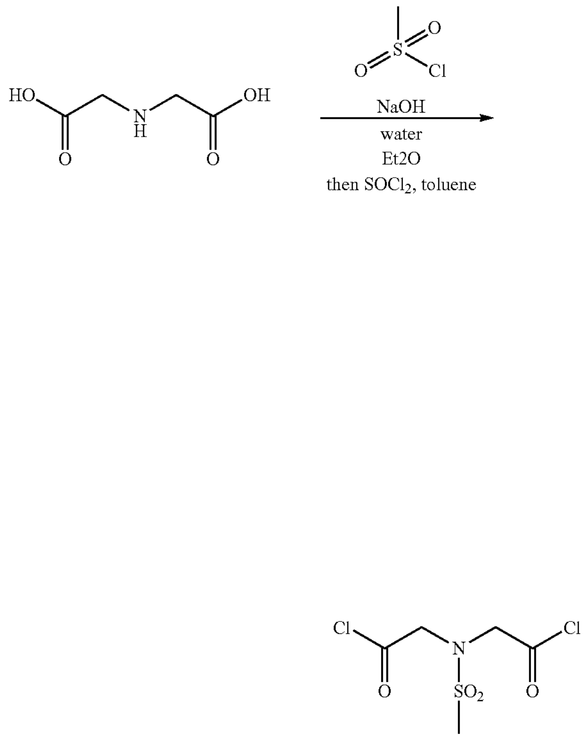

151

Sodium hydroxide (10.6 mL, 400 mmol) was dissolved in water (200 mL). Then, iminodiacetic acid (13.3 g, 100 mmol) was added at rt. Methanesulfonyl chloride (12.4 mL, 160 mmol) was dissolved in $Et_2O$ (100 mL) and added dropwise over 1 h. The reaction was stirred for 5 h then ethyl ether was removed in vacuo. The pH of the reaction mixture was adjusted to 1 with HCl. The mixture was extracted with EtOAc, dried and concentrated resulting in a colorless solid (250 mg). The colorless solid was then put into toluene and treated with thionyl chloride and stirred overnight. Mixture was concentrated and confirmed to be product 151 by NMR.

Step 2

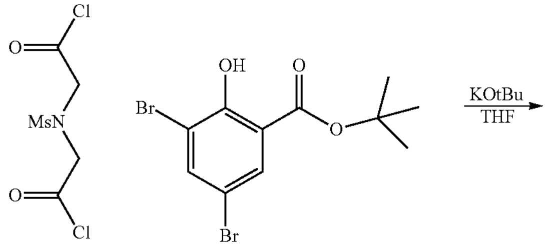

151

-continued

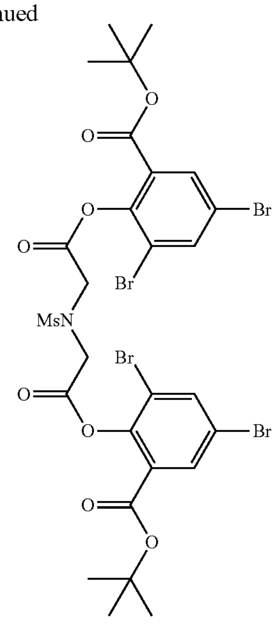

153

Potassium tert-butoxide (118 mg, 1.03 mmol) was added to 3,5-dibromosalicylic acid t-butyl ester (363 mg, 1.03 mmol) in THF (5.16 mL) at rt. Yellow color and no precipitate was observed in the mixture. After 1 h of stirring, 151 (128 mg, 516 umol) was added. After 2 h, all volatiles were removed in vacuo yielding 505 mg tan solid (111% based on free compound).

Step 3

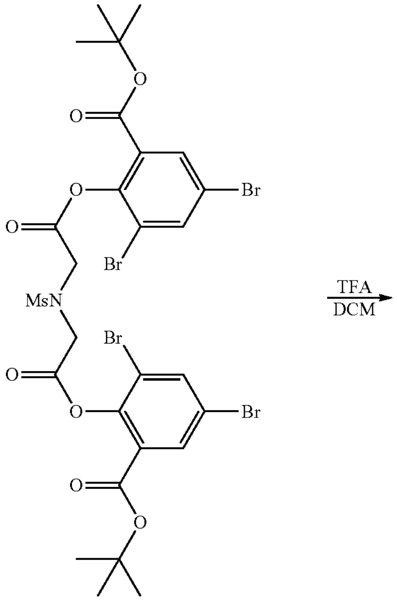

153

-continued

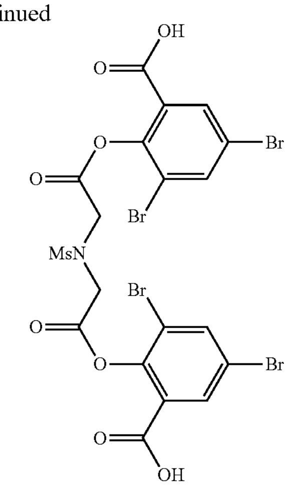

MIDA

Compound 153 (505 mg, 574.0 umol) was added to DCM (3 mL) at rt. Trifluoroacetic acid (3.00 mL, 39.2 mmol) was added and stirred until TLC determined the reaction was complete. The reaction mixture was then concentrated. Product MIDA was isolated (393 mg, 89% yield).

Example 13: Synthesis of Tosyl Iminodiacetic Acid (TIDA)

Step 1

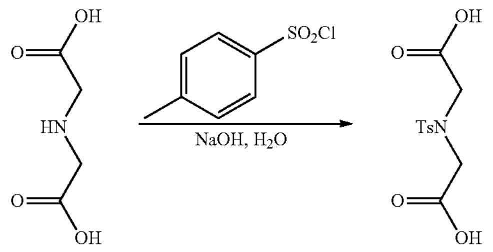

156

The intermediate compound 156 was made analogously to compound 151, in 56% yield.

Step 2

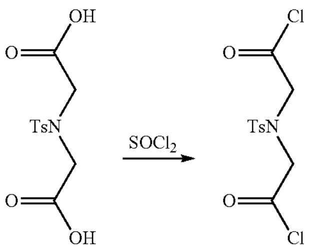

156 157

Thionyl chloride (16.7 mL, 229 mmol) and 156 (6.59 g, 22.9 mmol) was mixed at rt. One drop of DMF was added. After 4 h, a milky white solution/suspension was formed. The reaction mixture was heated slightly with heating mantle overnight then concentrated in vacuo. The product, 157 along with by-products were then washed with heptane, concentrated in vacuo and placed on high vacuum.

Step 3

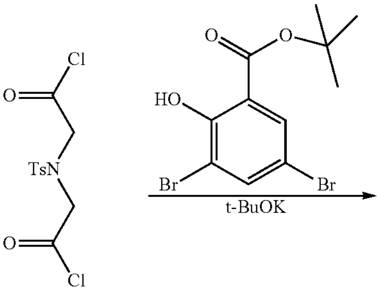

157

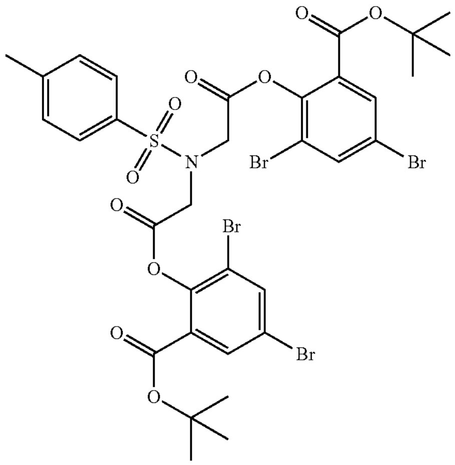

159

3,5-Dibromosalicylic acid t-butyl ester (1.20 g, 3.41 mmol) was added to potassium tert-butoxide (781 mg, 6.82 mmol) at rt. 157 (1.11 g, 3.41 mmol) in THF (40.0 mL) was added. The mixture was stirred 5 h then concentrated in vacuo. Compound 159 was isolated and used for the next step.

Step 4

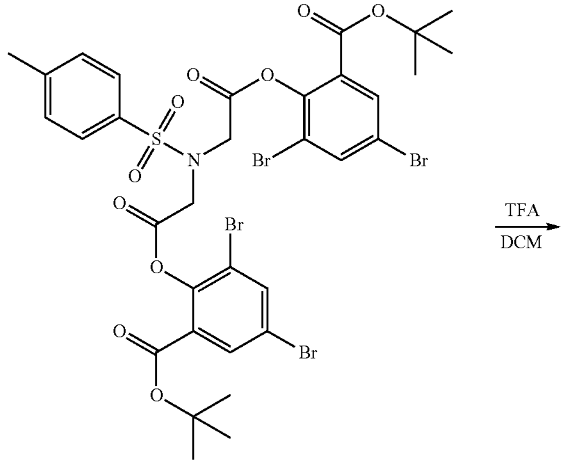

159

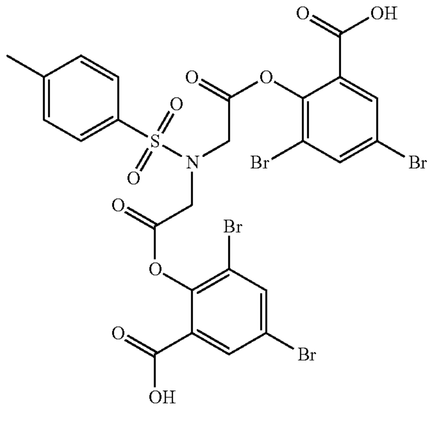

TIDA

Compound 159 (1.88 g, 1.97 mmol) was mixed with trifluoroacetic acid (5.00 mL, 65.3 mmol) and DCM (5 mL) and stirred at rt until TLC indicated the reaction was done then was concentrated in vacuo yielding 2.10 g product as TIDA as the product (127% yield based on pure product).

Example 14: Synthesis of Aniline Iminodiacetic Acid (AIDA)

Step 1

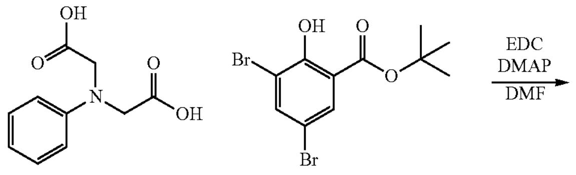

-continued

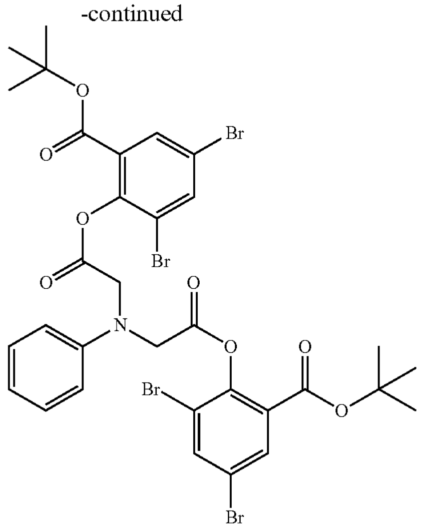

166-2 t-Buty-1,3-dibromosalicylate (763 mg, 2.17 mmol) phenyliminodiacetic acid (216 mg, 1.03 mmol) was mixed with EDC (594 mg, 3.10 mmol) in DCM (50 mL) at rt. Reaction was run overnight. A sample was taken for flash chromatography. Then the reaction was partially concentrated and columned with silica gel FCC (0-10% EtOAc in heptane) to obtain product 166-2.

Step 2

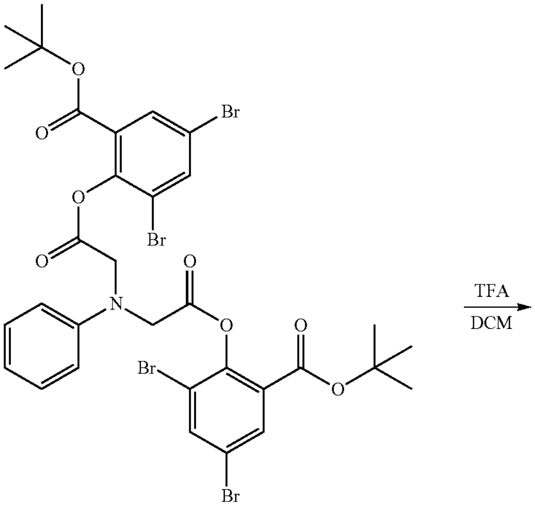

166-2

-continued

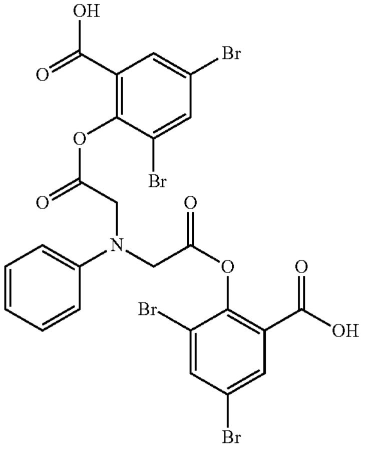

AIDA

Compound 166-2 (120 mg, 137 umol), trifluoroacetic acid (1.00 mL, 13.1 mmol) and DCM (265 uL) were stirred at rt. After 5 h, the mixture was concentrated, then taken up in hot MeCN and decanted from solid. The decanted liquid was allowed to cool and then placed in the freezer then concentrated to provide product AIDA.

Example 15: Synthesis of Azide Functionalized Isophthalate-Based Crosslinkers For isophthalate-based crosslinkers, the synthesis of two types of $N_3$-PEGn-bis-3,5-dibromosalicyl isophthalate crosslinkers ($N_3$-PEGn-IA-DBS linkers) shown below have been established. The crosslinkers can be used as a selective intramolecular crosslink to stabilize the bovine hemoglobin (bHb) tetramer and carry a single site of functionalization for subsequent multimerization chemistry via a click cycloaddition reaction. Both Type 1 and Type 2 crosslinkers with PEG4 and PEG 9 chains, as shown below, were synthesized.

Type 1

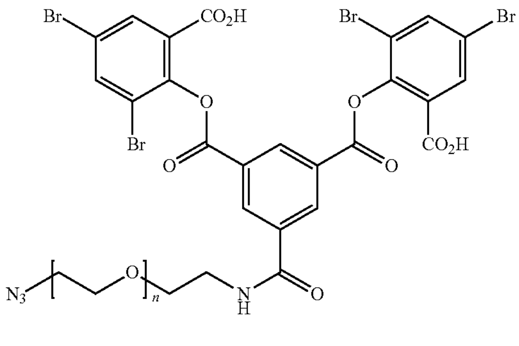

-continued

Type 2

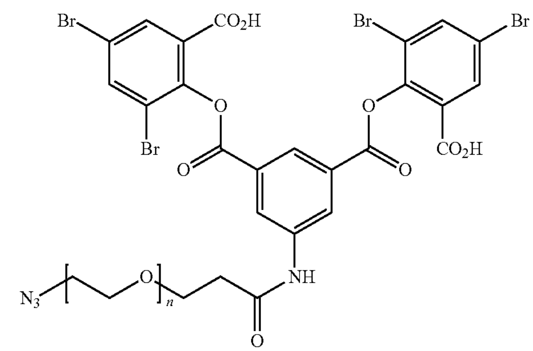

n = 4 or 9

Type 1 Crosslinkers

Introduction.

Figure 7:
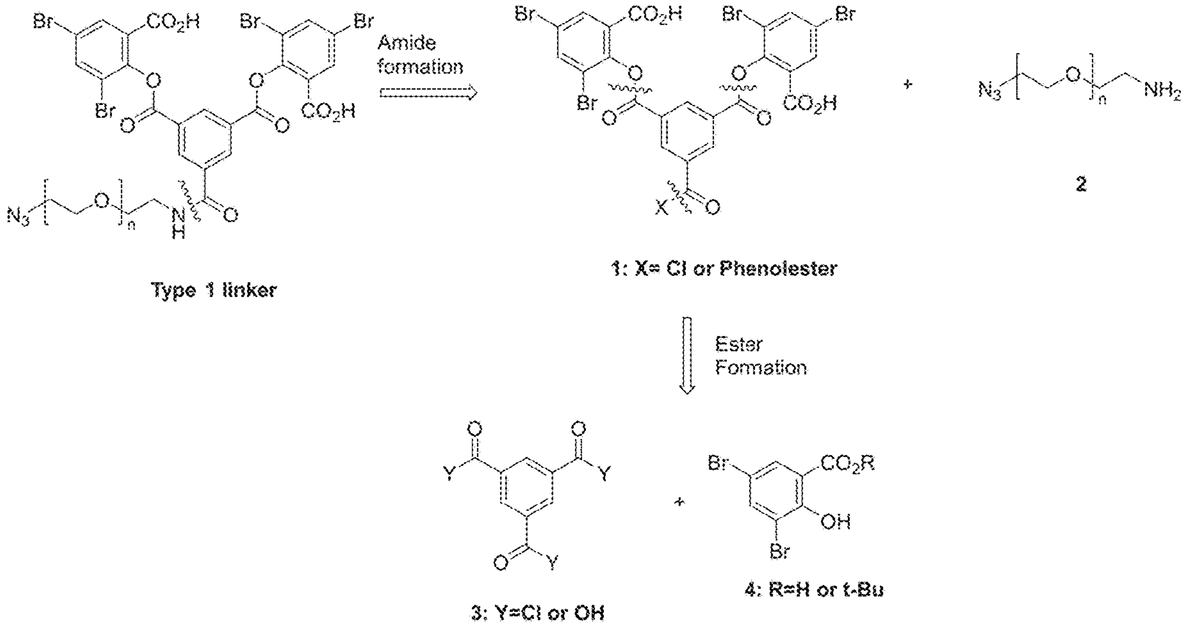
FIG. 7 is a retrosynthetic analysis of Type 1 $N_3$-PEGn-IA-DBS linkers (e.g., DBSNP-4, DBSNP-9 in Table A below).

The Type 1 crosslinker is an acid type linker—in which the PEG chain is introduced by reaction of an acid with $N_3$-PEGn-$NH_2$. FIG. 7 shows a retrosynthetic analysis of the Type 1 linker.

As shown in FIG. 7, reaction of compound 1 and 0.33 equivalents of $N_3$-PEGn-$NH_2$ (2) would form the desired azide-functionalized isophthalate-based crosslinker in an amidation reaction in which only one of the three DBS esters reacts. Compound 1 could be formed by ester formation by reaction of trimesic acid (3, Y═OH) plus a carbodiimide reagent or an activated derivative (3, Y═Cl) with a protected ester derivative of 3,5-dibromosalicylic acid. The activated trimesic acid 3 could be trimesoyl chloride or a similarly reactive compound.

Two materials, t-Bu DBS and t-Bu TTDS are crucial intermediates for the synthesis of both linkers. This section will discuss the synthesis of both of these materials.

Step 1. Synthesis of t-Bu DBS

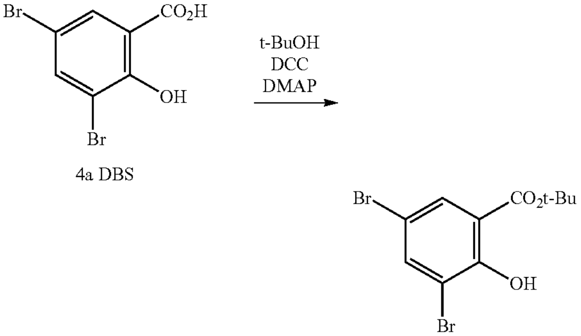

4a DBS 4b t-Bu DBS

The synthesis of t-Bu DBS from DBS was reported in the literature. Instead of using DMAP as catalyst, the literature suggested using 4-pyrrolindinepyridine as catalyst. After completion of the reaction, the catalyst was removed by addition of oxalic acid to form a salt which was subsequently crystallised from ether. The procedure was repeated several times, however, only twice obtained the desired material which successfully processed to the next step in the t-Bu TTDS formation. A number of other trials for the synthesis of the t-Bu DBS either from different source starting materials, solvents or by different bases failed to give the desired material which smoothly reacted with trimesoyl chloride in the following step.

Before commencing the synthesis of t-Bu DBS, further investigation was carried out in order to ascertain why certain batches of t-Bu DBS in previous project were unable to be carried through to the desired product. Analysis of a non-functioning batch of tBu-DBS was carried out by $^{1}$H-NMR (FIG. 9).

Figure 9:
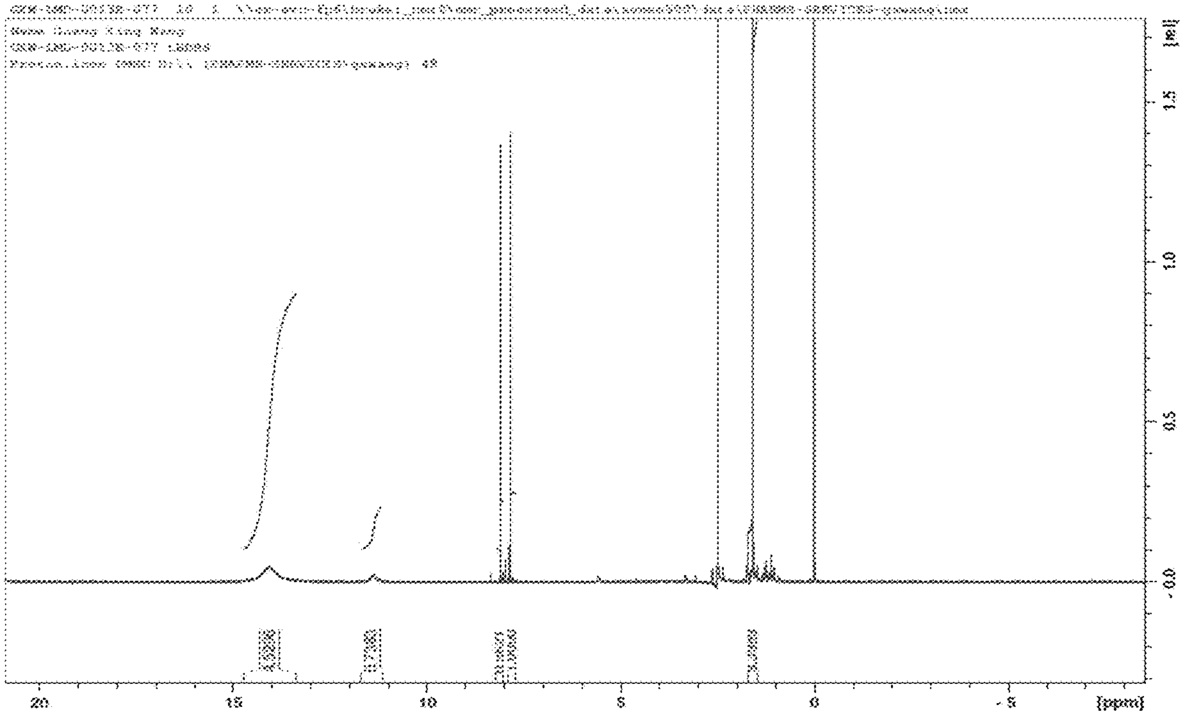
FIG. 9 is a $^1H$ NMR spectrum of non-functioning batch of tBu-3,5-dibromosalicylic acid (tBu-DBS).

As shown in FIG. 9, $^{1}$H NMR confirmed that the majority peaks of the obtained material matched the product with some impurity peaks presented. A broad peak appearing at 14 ppm was attributed to oxalic acid which was used during the work up and isolation of the t-Bu DBS. This peak appears to be of a higher concentration than in previous working batches of t-Bu DBS. This level of residual oxalic acid prevented the deprotonation of phenol to phenoxide, as the oxalic acid consumed all the base added, potentially explaining why certain batches were unsuccessful in being carried through to later stages of the synthesis.

After identifying the difficulty of removing the oxalic acid, the synthesis was performed without addition of any oxalic acid. Experimental procedure of t-Bu DBS is as follows.

Figure 10:
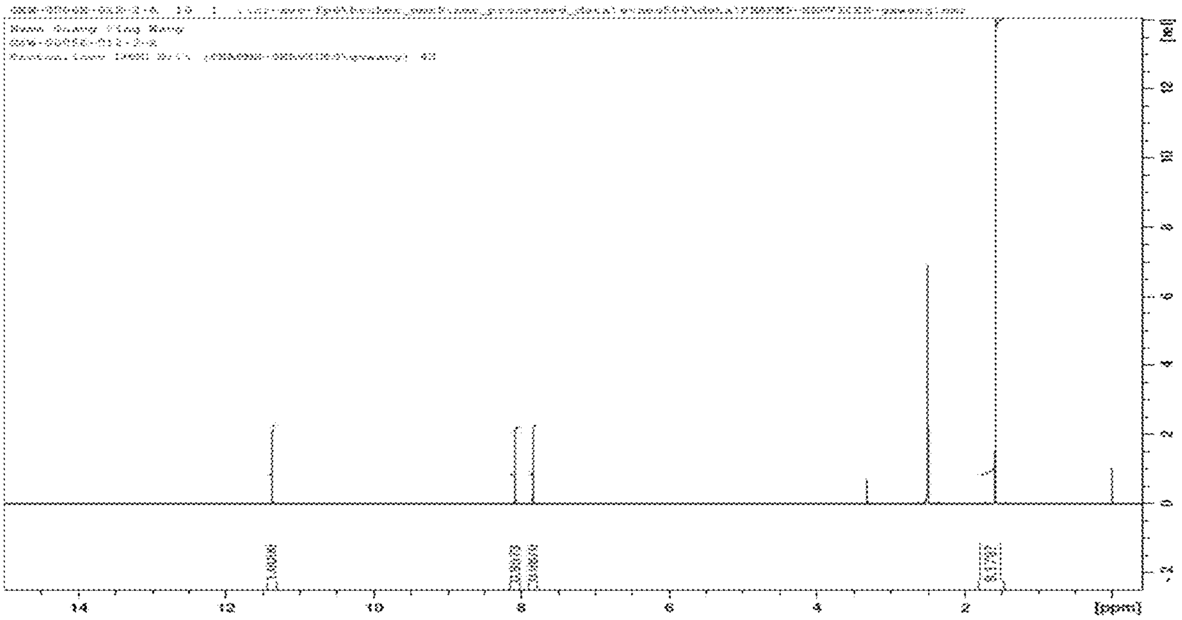
FIG. 10 is a $^1H$ NMR spectrum of tBu-DBS.

To a suspension of DBS (50 g, 0.179 mol) and DMAP (1.03 g, 8.45 mmol, 0.05 equiv) in anhydrous t-BuOH (500 mL) and dry THF (300 mL) was added a solution of DCC (38.4 g, 0.186 mol, 1.1 equiv) in THF (100 mL) at RT. The mixture was stirred at RT for 4 h. The precipitated DCU was removed by filtration. The filtrate was evaporated, and the residue refluxed with ether (500 mL). After cooling to RT, the solid was removed and washed with ether. The combined washes and filtrate were evaporated under reduced pressure to give a white solid. The solid was crystallised from EtOH (300 mL). The product was dried under vacuum at 40° C. to a constant weight to give product as a cotton-like white solid (50.86 g, 86% Isolated Yield). This procedure has been repeated 4 times. In total, >120 g of t-Bu DBS was obtained.

t-Bu ester formation of the DBS was performed in a solvent mixture of t-BuOH and THF using DCC as coupling reagent and DMAP as catalyst. The reaction was completed after 4 h at RT. The DCU formed was then removed and solvents were evaporated, further DCU was removed by refluxing with ether. Instead of oxalate salt formation, the catalyst was removed by crystallisation from EtOH. After these treatments, the product was obtained as a white cotton-like solid. $^{1}$H NMR (FIG. 10) clearly and cleanly confirmed the desired product.

Step 2. Synthesis of t-Bu TTDS

With pure t-Bu DBS in hand, the synthesis of t-Bu TTDS was performed as follows.

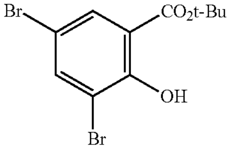

4b t-Bu DBS

+

-continued

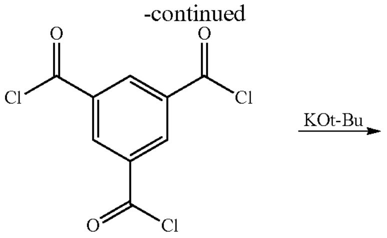

3a

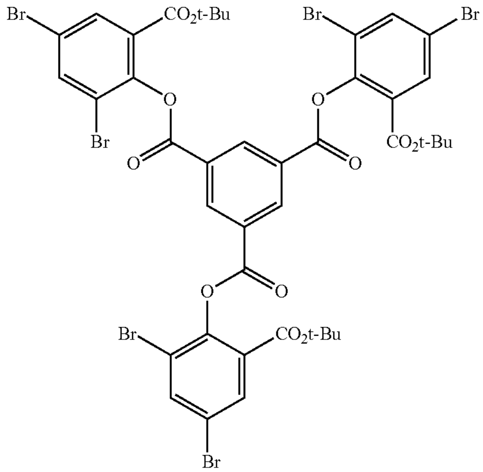

t-Bu TTDS

Figure 11:
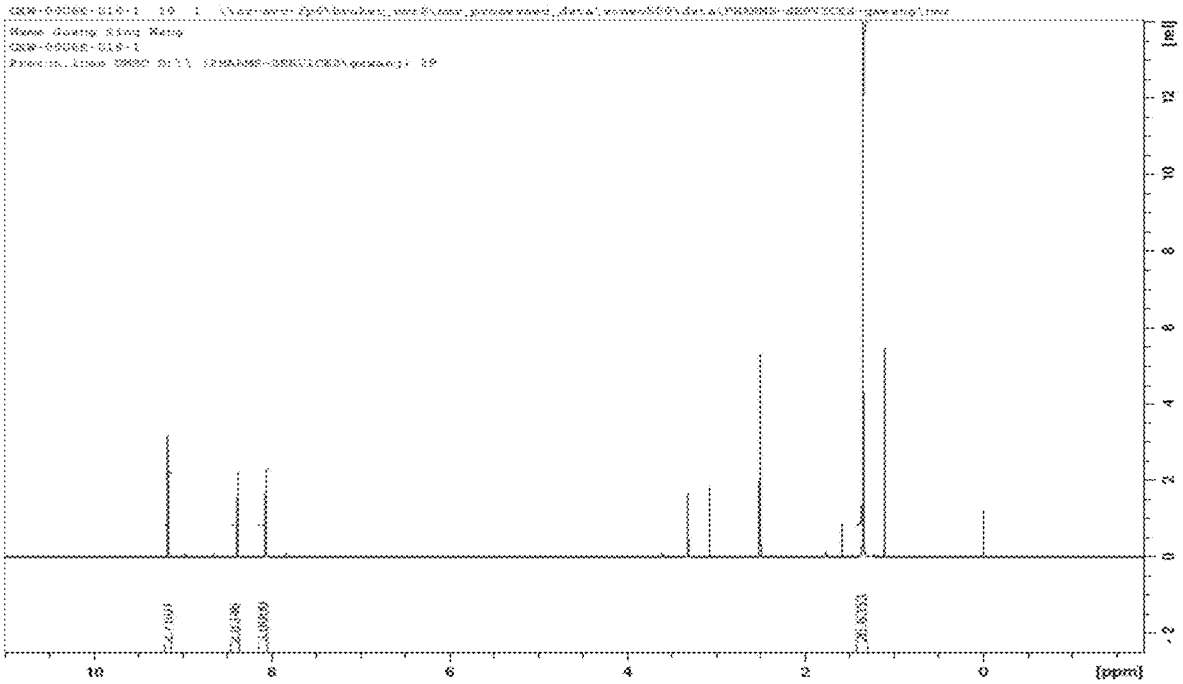
FIG. 11 is a $^1H$ NMR spectrum of tBu-trimesoyltris(1-(tert-butoxycarbonyl)-3,5-dibromosalicylate (tBu-TTDS).

To a solution of t-Bu DBS (28.5 g, 81 mmol, 3 equiv) in dry THE (500 mL) was added t-BuOK (9.24 g, 82 mmol, 3.05 equiv) at RT. The solution was stirred at RT for 15 min. A solution of trimesoyl chloride (7.17 g, 27 mmol, 1 equiv) in dry THF (100 mL) was then added dropwise to the solution over 15 min. The mixture was then stirred at RT for overnight. Half of the THF was then removed, MTBE (600 mL) was added, and the mixture was washed with water (2×). The organic layer was dried over $MgSO_4$. After filtration, the solvent was removed under reduced pressure and the residue was dried under vacuum at 45° C. for 6 h to give product as a white solid (32.8 g, 100% ISOLATED YIELD). This procedure had been repeated 3 times. In total, >100 g of t-Bu TTDS was obtained. [0323]t-Bu DBS was deprotonated by t-BuOK and the formed phenoxide was reacted with trimesoyl chloride in THF at RT which cleanly and smoothly afforded desired t-Bu TTDS. FIG. 11 showed the $^{1}$H NMR of the obtained product. The purity was 96.9% (w/w) by Q NMR with MTBE content: 3.49% (w/w).

Figure 12:
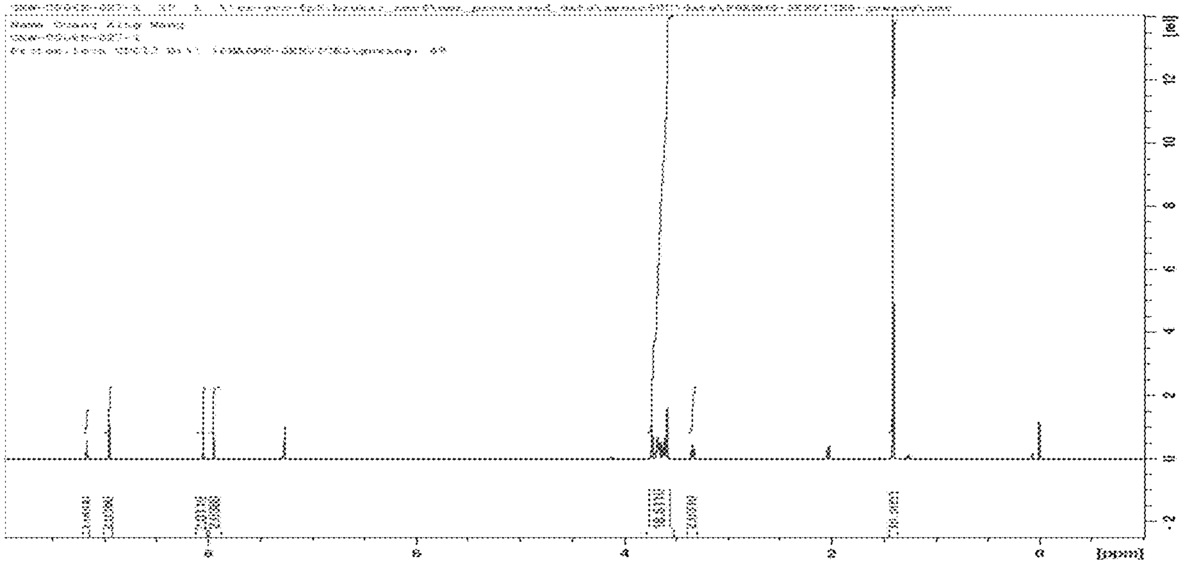
FIG. 12 is $^1H$ NMR spectrum of t-Bu $N_3$-PEG4-IA Type 1 linker.
Figure 13:
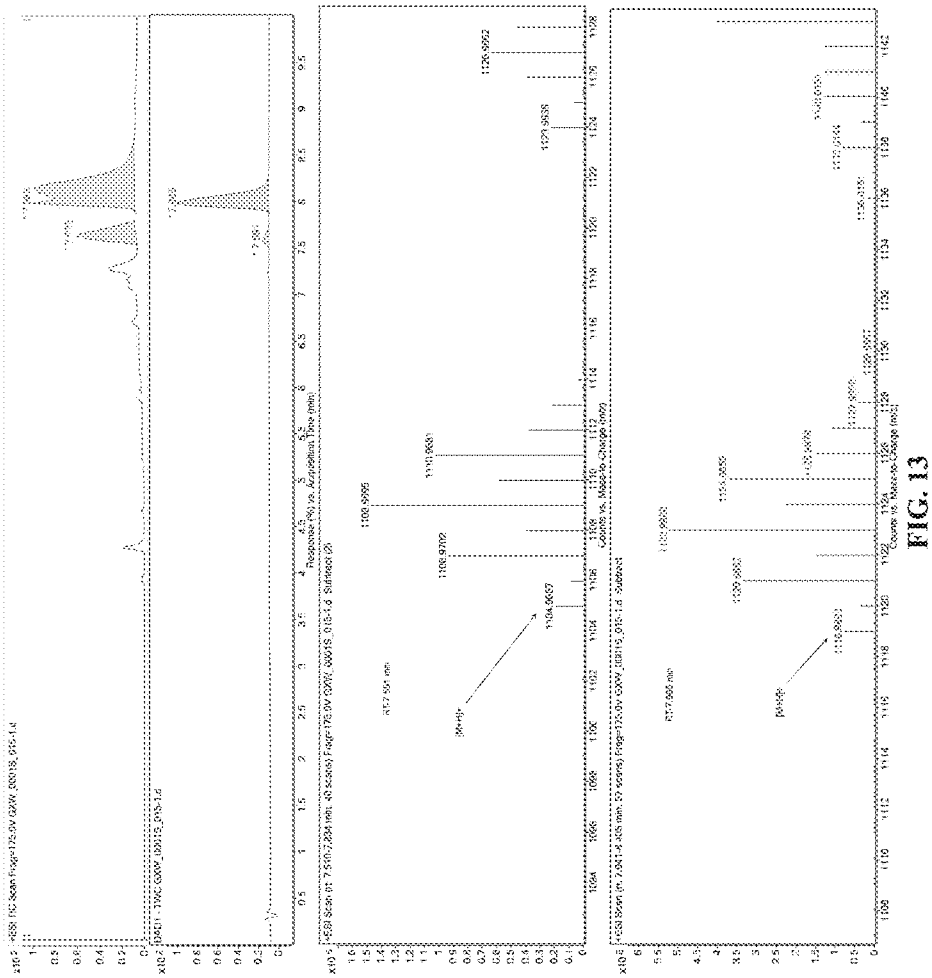
FIG. 13 shows liquid chromatography-mass spectrometry (LC-MS) spectra of t-Bu $N_3$-PEG4-IA Type 1 linker.

Step 3. Introduction of $N_3$-(PEG)$_n$ Chain by Amidation of a Single 3,5-dibromosalicyl Ester Active phenyl esters such as polyfluoro phenyl ester and nitrophenyl ester can act as good leaving groups for amidation reactions. In contrast, unsubstituted phenyl esters are reasonably stable. Generally, introduction of electron-withdrawing group will enhance the leaving activity of the phenyl ester. Comparing to active ester, t-Bu TTDS has a tri-phenyl ester which may be result in more favorable attack by the amino group The reaction was attempted with 1.5 equiv of t-Bu TTDS to $N_3$-PEG4-$NH_2$ catalyzed by 0.3 equiv of DMAP in DMF at 60° C. After 60 h, TLC showed a new product formed along with the excess t-Bu TTDS and by-product t-Bu DBS. The reaction was then worked-up and purification by flash chromatography, the product was obtained as a white foam in 31.5% isolated yield. The structure was confirmed by $^{1}H$ NMR shown in FIG. 12 and LC-MS as shown in FIG. 13.

Further experiments to improve the yield was undertaken. It was found that by exchanging the base from 0.3 equiv (DMAP) to 1 equiv (DIPEA), a significant improvement in yield was obtained (from 31.5% to 60%). One of the best conditions was using 1.3 equiv of t-Bu TTDS, 1 equiv of DIPEA in 30 vol DMF at 50° C. for 20 h. Under these conditions, the isolated yield of obtained product was typically approximately 60% in multiple runs.

Both PEG4 and PEG9 versions of the Type 1 crosslinker were prepared according to the following experimental procedures.

PEG4 Type 1 Crosslinker (t-Bu $N_3$-$PEG_4$)

To a solution of t-Bu TTDS (18 g, 14.9 mmol) in DMF (30 mL) was added DIPEA (1.99 mL, 11.4 mmol) at RT. The solution was stirred at RT for 10 min and a solution of $N_3$-PEG4-$NH_2$ (3 g, 11.4 mmol) in DMF (10 mL) during 10 min. The solution was heated at 50° C. for 20 h. The reaction was cooled to RT and EtOAc (~300 mL) was added. The mixture was washed by 5% citric acid, brine and dried over $MgSO_4$. The mixture was filtered, and the solvent was removed under reduced pressure. The residue was purified by flash chromatography using heptane:EtOAc=1:3 as eluent. Fractions containing desired product were collected and combined. The solvent was removed under reduced pressure and the residue was dried under vacuum at 45° C. for 8 h to give product as a colorless foam (8.475 g, 66% ISOLATED YIELD). This procedure was repeated for 3 times and >18 g of product was obtained.

PEG9 Type 1 Crosslinker (t-Bu $N_3$-$PEG_9$)

To a solution of t-Bu TTDS (6.53 g, 5.39 mmol) in DMF (20 mL) was added DIPEA (0.742 mL, 4.14 mmol) at RT. The solution was stirred at RT for 10 min and a solution of $N_3$-PEG9-$NH_2$ (2 g, 4.14 mmol) in DMF (10 mL) during 10 min. The solution was heated at 50° C. for 20 h. The reaction was cooled to RT and EtOAc (~100 mL) was added. The mixture was washed by 5% citric acid, brine and dried over $MgSO_4$. The mixture was filtered, and the solvent was removed under reduced pressure. The residue was purified by flash chromatography using EtOAc:EtOH=20:1 as eluents. Fractions of the various components were collected and combined. The solvent was removed under reduced pressure and the residue was dried under vacuum at 45° C. for 8 h to give two products. Product 1: colorless foam (0.134 g, PEG7 analogue); Product 2: colorless foam (3.598 g, 64.1% ISOLATED YIELD). This procedure was repeated x 2 and >7 g of product was obtained.

Step 4. Deprotection of the t-butyl Esters

To obtain the desired crosslinker deprotection of the bis-t-butyl ester was required. IN one embodiment, this was accomplished using trifluoroacetic acid (TFA).

Figure 14:
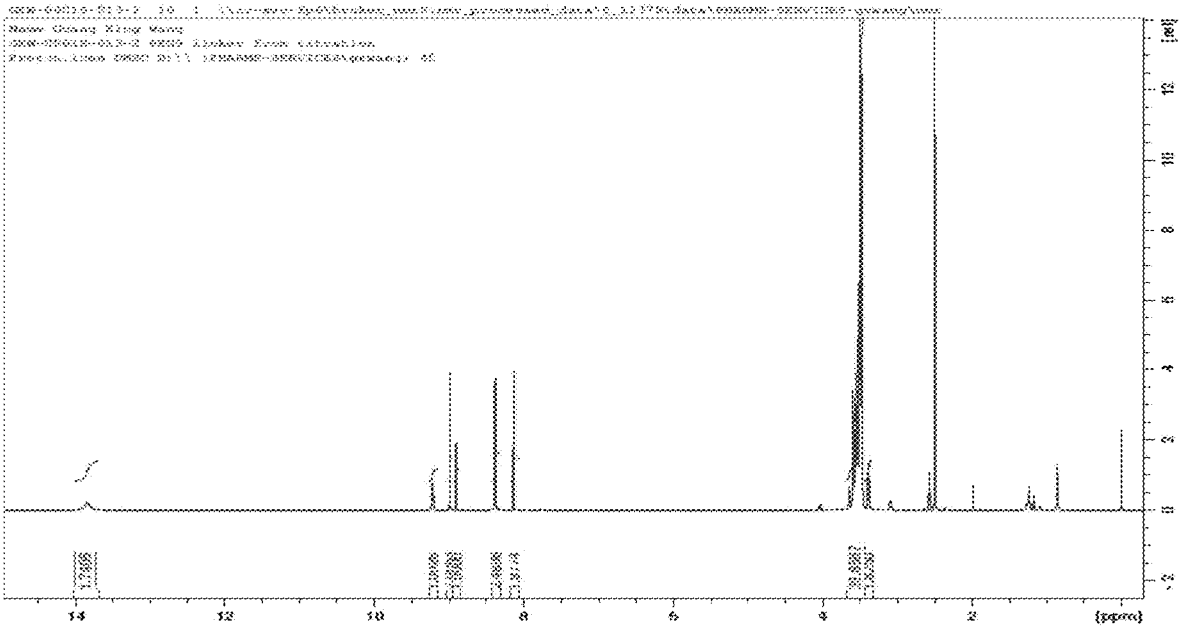
FIG. 14 is a $^1H$ NMR spectrum of $N_3$-PEG9-IA-DBS Type 1 Linker (i.e., DBSNP-9).
Figure 15:
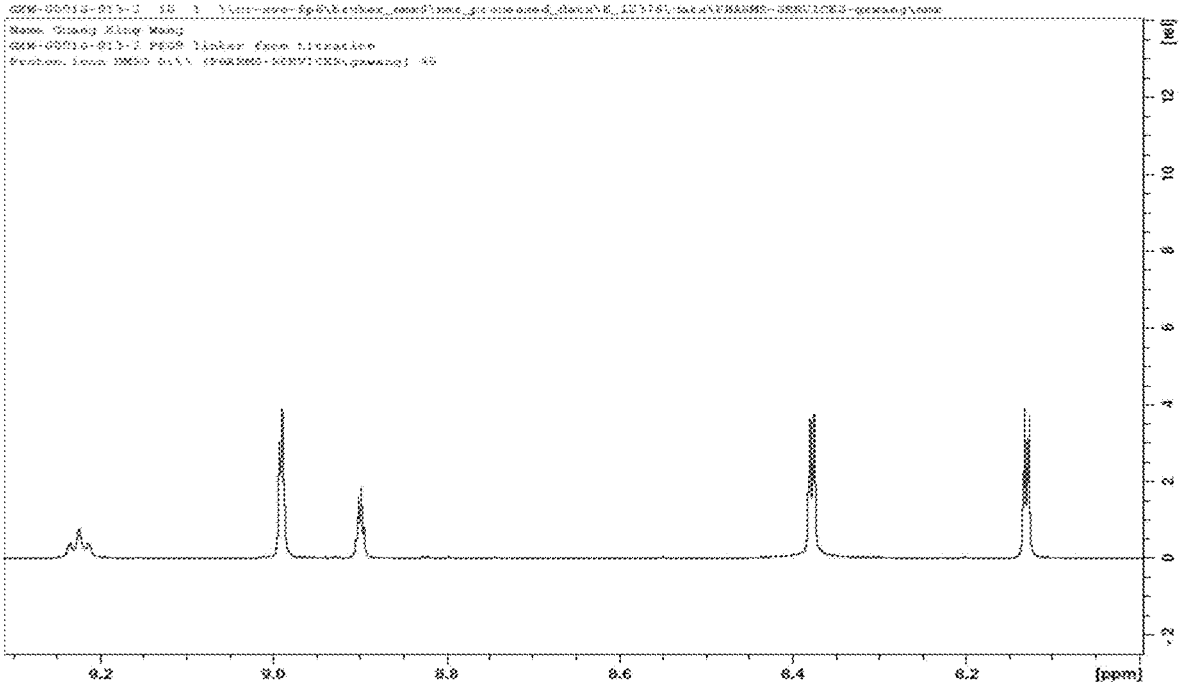
FIG. 15 shows expanded aromatic region of the $^1H$ NMR spectrum of FIG. 14.
Figure 16:
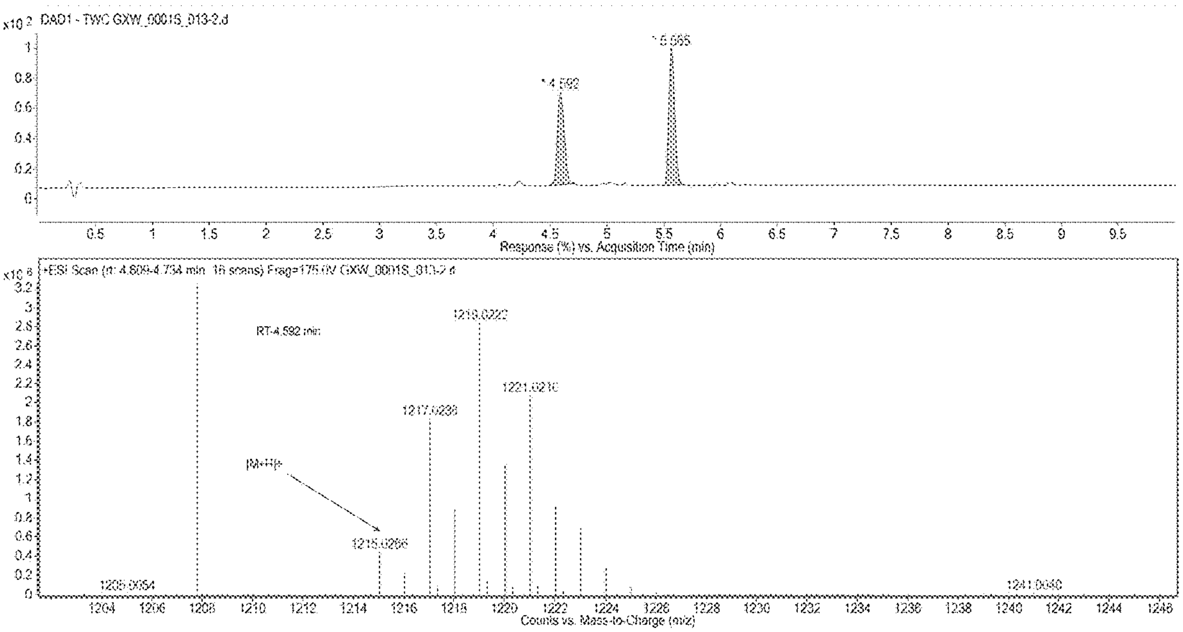
FIG. 16 shows LC-MS spectrum of $N_3$-PEG9-IA-DBS Type 1 Linker (i.e., DBSNP-9).

$N_3$-$PEG_9$-IA-DBS-linker (Type 1)

t-Bu N3-PEG9 type 1 linker (6.3 g, 4 mmol) was dissolved in TFA (HPLC grade, 50.6 mL, 140 equiv) at RT. The solution was stirred at RT for 1.5 h. Ether (70 mL) was then added to the solution. The solution was stirred at RT for 1 h and was added to heptane (500 mL). The mixture was stirred at RT for 3 h. A gel-like solid was formed on the wall of RFB. The above solution was decanted and the solid was dissolved in EtOAc (70 mL). Heptane (350 mL) was added to repeated above procedure for another 3 times. collected by filtration and washed with Heptane:EtOAc (1:5) for 3 times. The residue was dried under vacuum at 25° C. for 24 h to give product as a white solid (4.75 g, 82.3% ISOLATED YIELD). $^{1}H$ NMR and expanded aromatic range (FIGS. 14 and 15) conforms to the desired product. LC-MS (FIG. 16) showed that this material was also a mixture of two product in a ratio ~3:7. From the MS results, the structure of the impurity was similar as the nitroso impurity.

Type 2 Crosslinkers

Introduction.

The Type 2 linker is a 5-amino-isophthalate type linker in which the PEG chain is introduced by reaction of the amino group with $N_3$-$(PEG)_n$-COOH or its NHS ester. The synthetic route is shown in FIG. 8.

Figure 8:
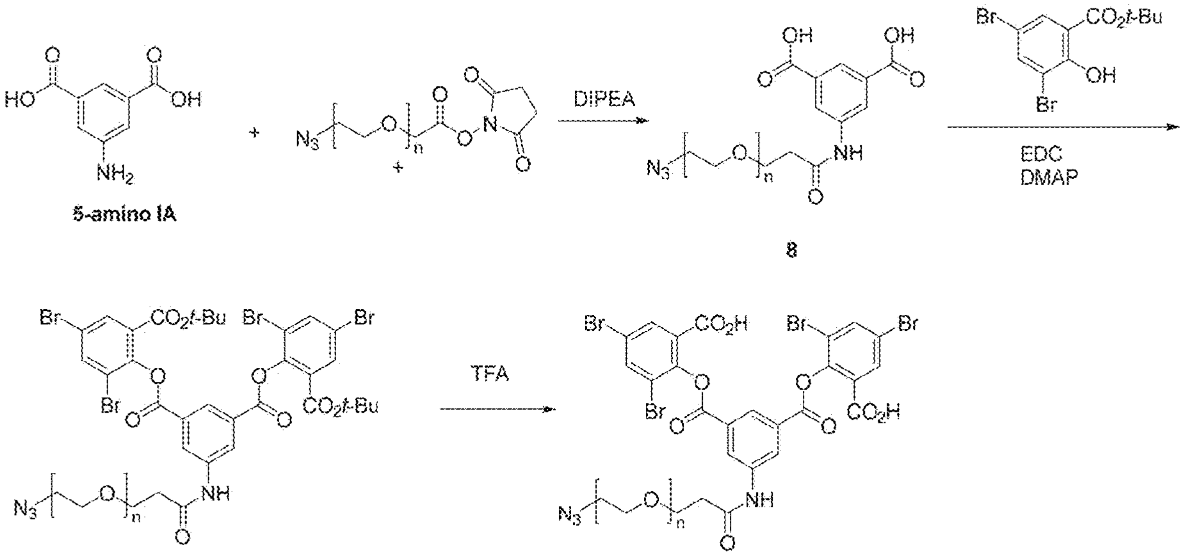
FIG. 8 outlines the synthesis of Type 2 $N_3$-PEGn-IA-DBS linkers (e.g., DBSNP-42, DBSNP-92 in Table A below).

As shown in FIG. 8, reaction of 5-amino isophthalic acid (5-amino IA) with $N_3$-PEGn-NHS (N-hydroxysuccinimidyl ester of $N_3$-PEGn $CO_2H$) under basic condition will afford $N_3$-PEGn-diacid compound 8. Ester formation of diacid with t-Bu DBS using EDC (ethyl dimethylamino carbodiimide) with catalytic amount of DMAP will give the t-Bu protected Type 2 isophthalate-based linker, which upon deprotection of t-Bu groups will result the desired Type 2 $N_3$-PEGn-IA-DBS crosslinkers (FIG. 8).

Step 1. Synthesis of the bis-DBS ester of 5-amino-isophthalic acid

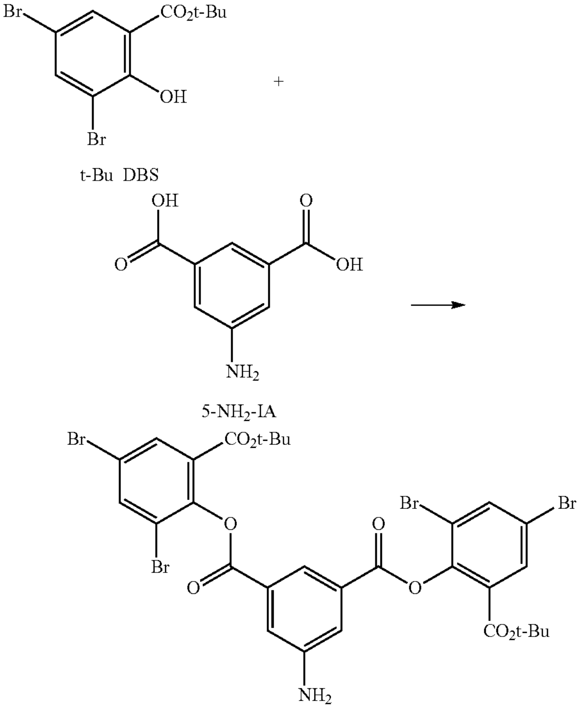

t-Bu DBS

+

5-$NH_2$-IA

5-$NH_2$-IA t-Bu DBS ester

To a suspension of 5-$NH_2$—IA (5 g, 27.6 mmol), t-Bu DBS (20.4 g, 58 mmol) and DMAP (1.01 g, 8.28 mmol) in DCM (120 mL) was added EDC (15.9 g, 82.8 mmol). The mixture was stirred at RT for 20 h. It was observed that the mixture turned to a pale-yellow solution. EtOAc (350 mL) and water (150 mL) were added to the solution. The mixture was stirred at RT for 20 min and the organic layer was separated. The organic layer was washed with 5% citric acid solution, brine and dried over $MgSO_4$. The mixture was filtered, and the solvent was removed under reduced pressure. The residual oil was solidified after standing for 16 h. EtOAc (60 mL) was added to the solid and the mixture was stirred at RT for 20 min. The solid was collected by filtration and washed by EtOAc and dried to give product as a white solid (13.72 g, GXW-0001S-046-1). The filtrate and washes were combined. The solution was evaporated to ~30 mL. The solution was allowed to crystallise at RT for 20 h. The solid was collected and washed with EtOAc. This procedure was repeated to prepare more product. In total, 17.3 g (73.8% ISOLATED YIELD) of product was obtained as a white solid.

Step 2. Formation of the Amide from bis-t-butyl DBS 5-amino-isophthalate

Various coupling conditions using EDC were tried. When both materials were treated with EDC catalysed by DMAP in DCM, the reaction progressed smoothly. TLC analysis confirmed that a main product formed after 20 h at RT. After work-up, the product was obtained by flash chromatography. The structures of the products were confirmed by $^{1}H$ NMR and LC-MS.

The reaction was also evaluated using propane phosphonic acid anhydride (T3P) as coupling reagent. It was found T3P coupling was a better option than EDC coupling due to easier work-up and cleaner reaction performance. The process was used for scale-up of both PEG4 and PEG9 linker synthesis as detailed below.

t-Bu $N_3$-$PEG_4$ Type 2 Linker

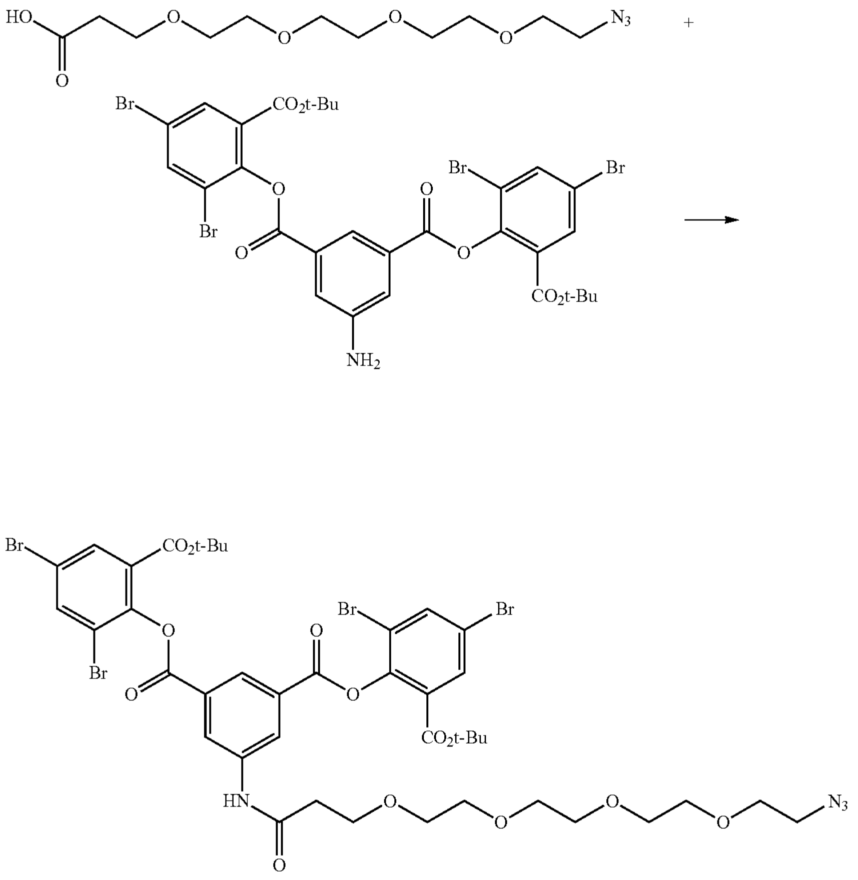

Figure 17:
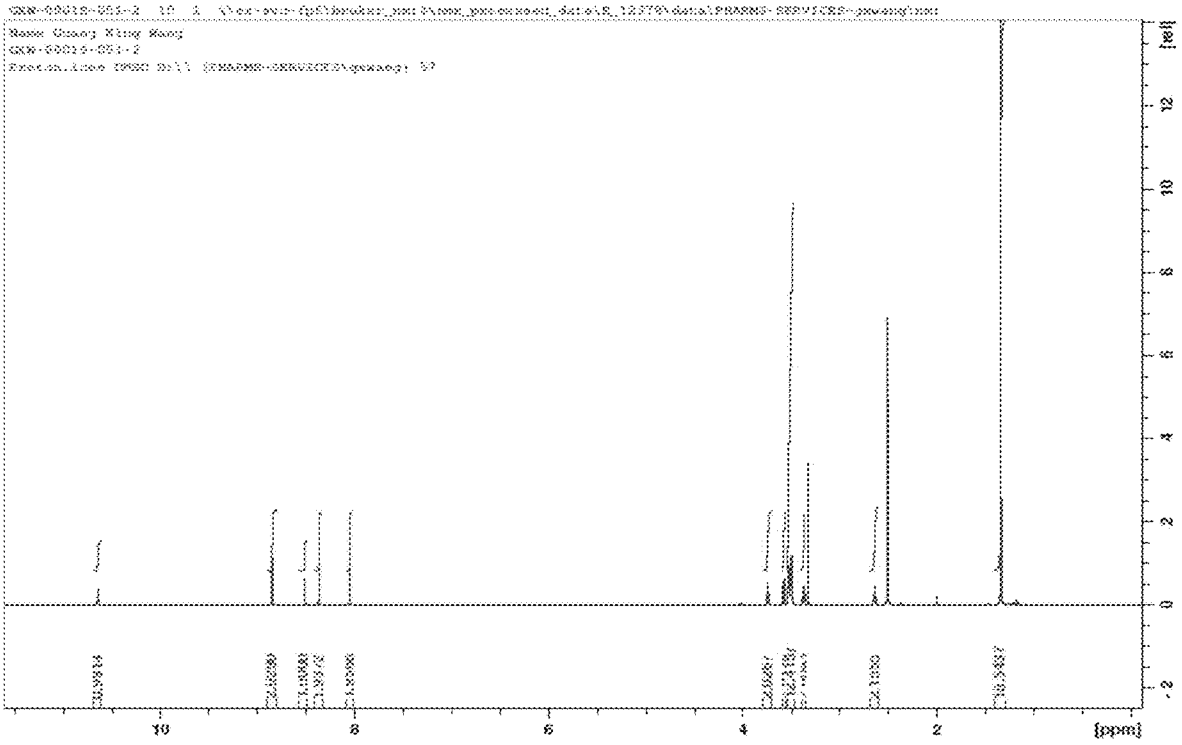
FIG. 17 is a $^1H$ NMR spectrum of t-Bu $N_3$-PEG4 Type 2 linker.
Figure 18:
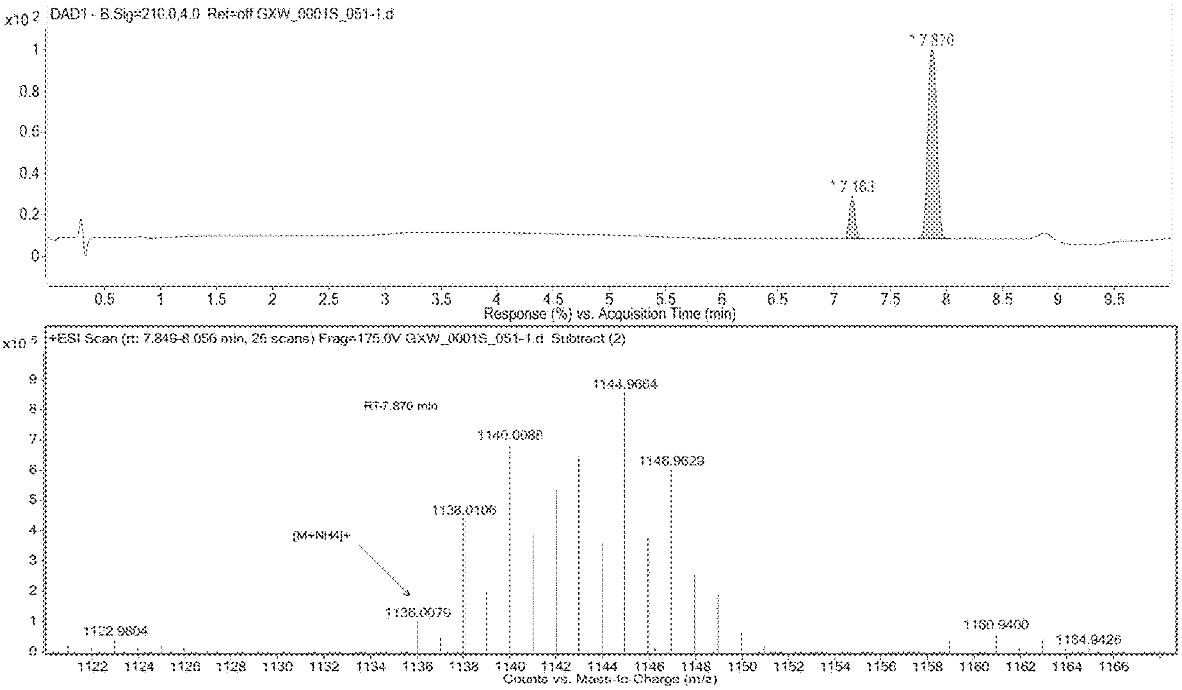
FIG. 18 shows LC-MS spectra of t-Bu $N_3$-PEG4 Type 2 linker.

To a suspension of $N_3$-PEG4-COOH (2.65 g, 9.56 mmol), 5-$NH_2$—IA-di-DBS ester (8.52 g, 10 mmol) and TEA (1.4 mL, 10 mmol) in EtOAc (250 mL) was added T3P (50% in EtOAc, 5.97 mL, 10 mmol) during 10 min. The mixture was stirred at RT for 20 h. It was observed that the mixture turned to a pale-yellow solution. Water (100 mL) was added, and the mixture was stirred at RT for 10 min. The organic layer was separated and washed water (100 mL) for another 2 times and dried over $MgSO_4$. The mixture was filtered, and the solvent was removed under reduced pressure. The residual was purified by flash chromatography to give product as a white foam (6.24 g, 58.2% ISOLATED YIELD). $^{1}H$ NMR (FIG. 17) and LC-MS (FIG. 18) conform to the structure.

t-Bu $N_3$-$PEG_9$ Type 2 Linker

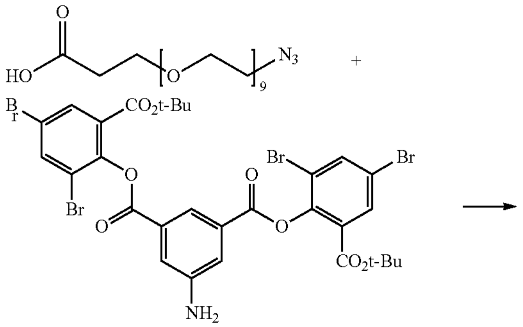

-continued

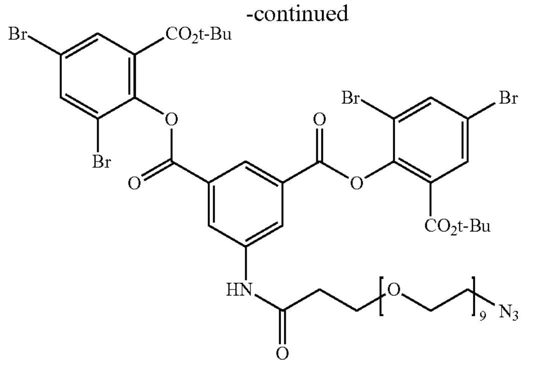

Figure 19:
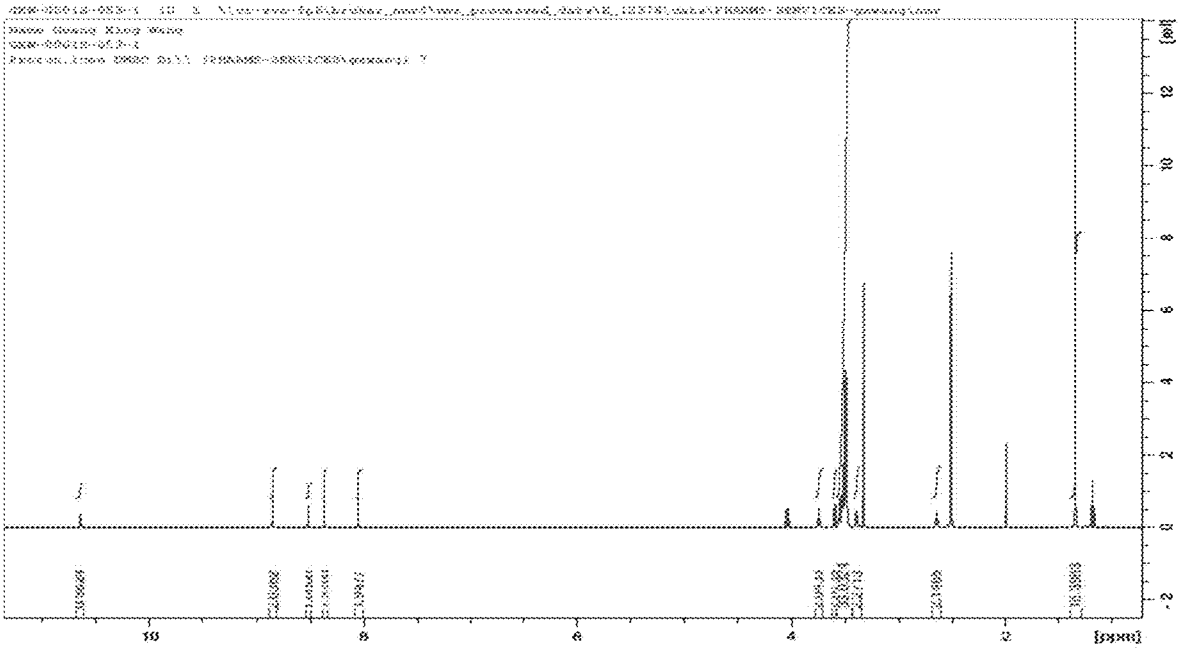
FIG. 19 is a $^1H$ NMR spectrum of t-Bu $N_3$-PEG9 Type 2 linker.
Figure 20:
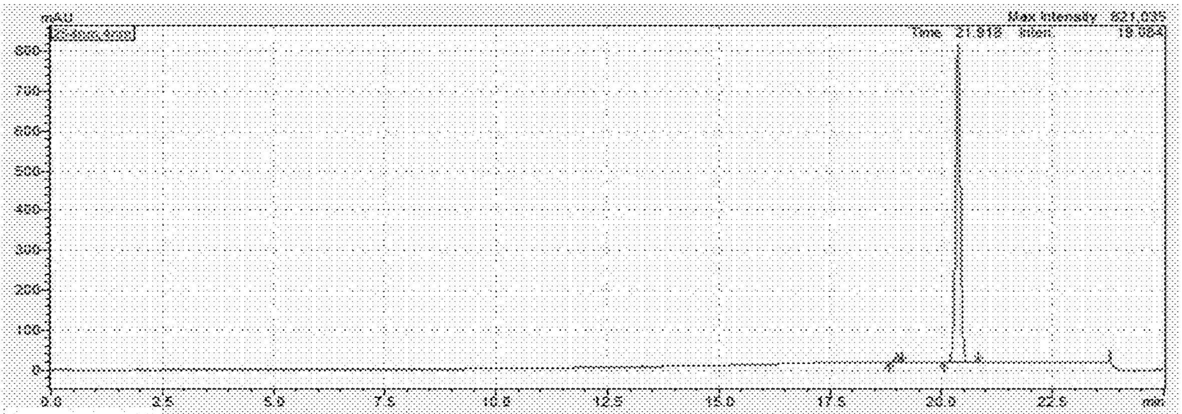
FIG. 20 shows high-performance liquid chromatography (HPLC) chromatogram of t-Bu $N_3$-PEG9 Type 2 linker.

To a suspension of $N_3$-PEG9-COOH (1 g, 1.95 mmol), 5-$NH_2$—IA-di-DBS ester (1.74 g, 2.05 mmol) and TEA (0.3 mL, 10 mmol) in EtOAc (50 mL) was added T3P (50% in EtOAc, 1.28 mL, 2.15 mmol) during 10 min. The mixture was stirred at RT for 30 h. It was observed that the mixture turned to a pale-yellow solution. Water (30 mL) was added, and the mixture was stirred at RT for 10 min. The organic layer was separated and washed water (30 mL) for another 2 times and dried over $MgSO_4$. The mixture was filtered, and the solvent was removed under reduced pressure. The residual was purified by flash chromatography to give product as a white foam (1.87 g, 58.2% ISOLATED YIELD, GXW-0001S-053-1). $^1H$ NMR (FIG. 19) conforms to the structure with a HPLC purity (FIG. 20) of 97.1% (P.A.). This procedure was repeated to another 2 g scale to give 2.78 g of product.

Step 3. Deprotection of t-Bu Groups Using HBr

The final step involved deprotection of the t-butyl ester. As some decomposition of the azide had been observed in this step when carried out in the synthesis of the Type 1 crosslinker, an alternative deprotection method was developed using HBr in place of trifluoroacetic acid.

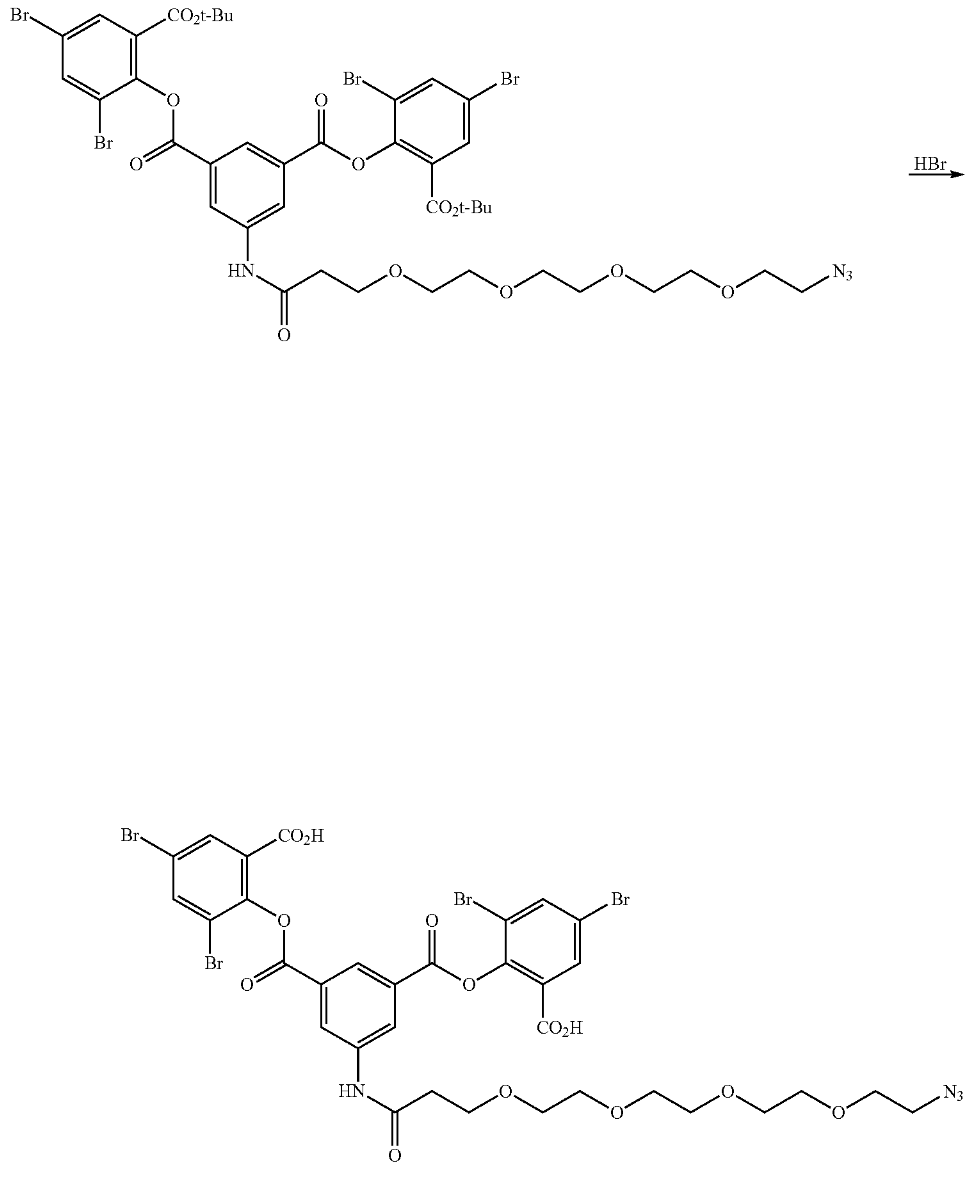

Previous results showed that inorganic acids such as HCl, $H_3PO_4$ or HBr did not produce or produced only trace amounts of nitroso impurity during the deprotection reactions. Among these acids, HBr in AcOH proved to be the best acid as it gave quick reaction. However, another two unknown impurities were also introduced using neat HBr in AcOH or 1:2 (v/v) in DCM. Comparing the results of these two reactions, the diluted HBr in dichloromethane (DCM) gave better purity than that of neat HBr in AcOH. From this observation, it appeared that more dilute HBr would further improve the purity of the desired product and reduce the amount of the other by-products.

The best result was found by using 2 equivalents of HBr in DCM, which gave the desired product with a purity of 95.5% (P.A.) with only 1.38% of nitroso impurity.

Example 16: Crosslinking of Hemoglobin with isophthalate-PEG4-Type 2 Crosslinker A 140 mL solution of 1 mM Hb (65 g/L) is made in 150 mM 3-(N-morpholino)propanesulfonic buffer (MOPS) with a pH of 6.8 is made in a 1.6 L reaction vessel. A 19.8 mM solution of Isophthalate-PEG4-Type 2 Crosslinker is prepared in DMSO, from which 1.4 mL of the solution is added in a single bolus to the 140 mL solution of hemoglobin. This is this gently mixed at 160 RPM at 31° C. overnight on a Benchmark Incu-ShakerMini. After 16 hours of mixing, the reaction is stopped, and 10 µL of the crosslinked solution diluted to 1 g/L and compared against a native hemoglobin standard on RP-HPLC. Crosslinking was estimated using a denaturing SDS-PAGE gel.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A compound of formula (I-1)

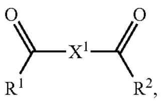

(I-1)

or a salt, a stereoisomer, or a deuterated form thereof, wherein:

$R^1$ and $R^2$ are each independently a leaving group;

$X^1$ is:

(i) $C_{6-10}$ arylene substituted with —C(O)—$R^1$, and wherein $R^1$ is a leaving group which is

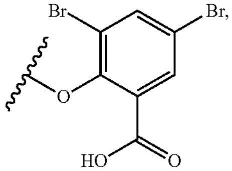 [SMILES: *Oc1c(Br)cc(Br)cc1C(=O)O]

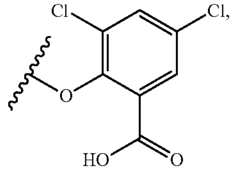

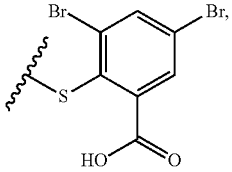

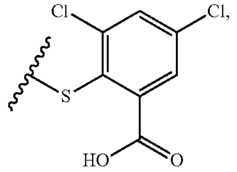

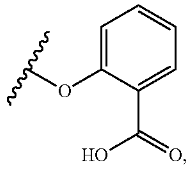

or

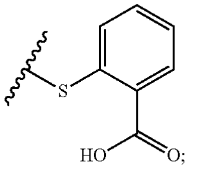

or (ii) $C_{6-10}$ arylene substituted with —C(O)NH—($C_{1-12}$ alkylene)-$(OCH_2CH_2)_m$—$(CH_2)_n$—$N_3$, or —NHC(O)—($C_{1-12}$ alkylene)-$(OCH_2CH_2)_m$—$(CH_2)_n$—$N_3$, and wherein each m is independently an integer of 1-200, and each n is independently an integer of 0-100;

wherein $X^1$ is optionally substituted with 1 or 2 $R^3$ as permitted by valency, and each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-12}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50, with the proviso that:

if $X^1$ is

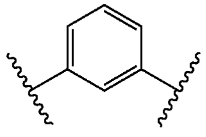

then the leaving group is not

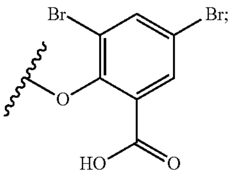

if $X^1$ is an arylene substituted with one $R^3$, then $R^3$ is different from —C(O)—$R^1$ or —C(O)—$R^2$; and the compound is not

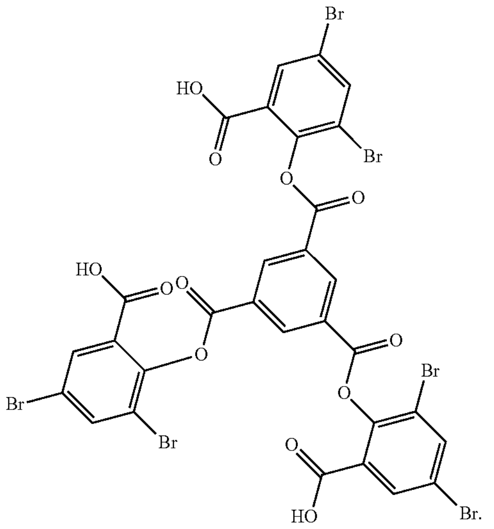 [SMILES: O=C(Oc1c(Br)cc(Br)cc1C(=O)O)c1cc(C(=O)Oc2c(Br)cc(Br)cc2C(=O)O)cc(C(=O)Oc2c(Br)cc(Br)cc2C(=O)O)c1]

2. The compound of claim 1, or a salt, a stereoisomer, or a deuterated form thereof, wherein $X^1$ is

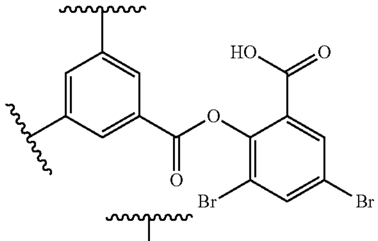

or

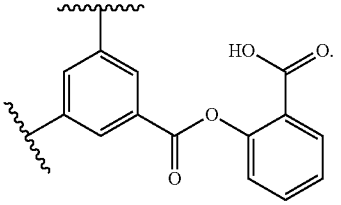

3. The compound of claim 1, or a salt, a stereoisomer, or a deuterated form thereof, wherein $X^1$ is $C_{6-10}$ arylene substituted with —C(O)NH—($C_{1-6}$ alkylene)-($OCH_2CH_2$)$_m$—$N_3$, and wherein m is an integer of 2-50.

4. The compound of claim 3, or a salt, a stereoisomer, or a deuterated form thereof, wherein $X^1$ is

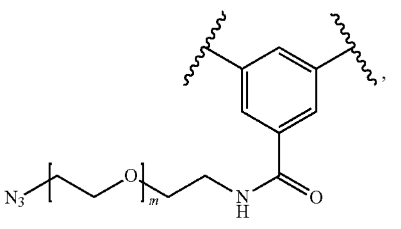

and wherein m is 4 or 9.

5. The compound of claim 1, or a salt, a stereoisomer, or a deuterated form thereof, wherein $X^1$ is $C_{6-10}$ arylene substituted with —NHC(O)—($C_{1-6}$ alkylene)-($OCH_2CH_2$)$_m$—$N_3$, and wherein m is an integer of 2-50.

6. The compound of claim 5, or a salt, a stereoisomer, or a deuterated form thereof, wherein $X^1$ is

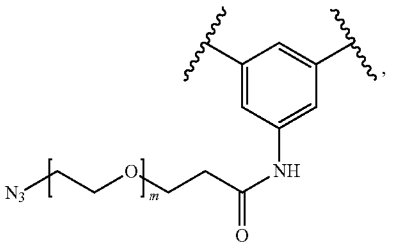

and wherein m is 4 or 9.

7. A compound of formula (I-2)

(I-2)

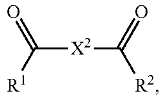

or a salt, a stereoisomer, or a deuterated form thereof, wherein:

$X^2$ is -$L^1$-$NR^A$-$L^2$, $R^1$ and $R^2$ are each independently a leaving group;

$R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-($OCH_2CH_2$)$_m$—($CH_2$)$_n$—$N_3$, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-12}$ alkylene)-$N_3$, —($C_{1-12}$ alkylene)-($OCH_2CH_2$)$_m$—($CH_2$)$_n$—$N_3$, —C(O)NH—($C_{1-12}$ alkylene)-($OCH_2CH_2$)$_m$—($CH_2$)$_n$—$N_3$, —NHC(O)—($C_{1-12}$ alkylene)-($OCH_2CH_2$)$_m$—($CH_2$)$_n$—$N_3$, —O—($C_{1-12}$ alkylene)-($OCH_2CH_2$)$_m$—($CH_2$)$_n$—$N_3$, —S—($C_{1-12}$ alkylene)-($OCH_2CH_2$)$_m$—($CH_2$)$_n$—$N_3$, or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

8. The compound of claim 1, or a salt, a stereoisomer, or a deuterated form thereof, wherein $R^1$ and $R^2$ are a leaving group, and wherein:

the leaving group is

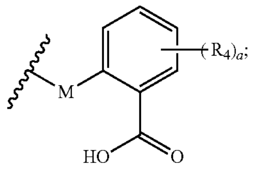

M is O or S;

each $R^4$ is independently halogen or $—C_{1-6}$ alkyl; and a is an integer of 0-4, with the proviso that:

if $X^1$ is

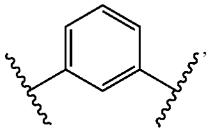 [SMILES: *c1cccc(*)c1]

then the leaving group is not

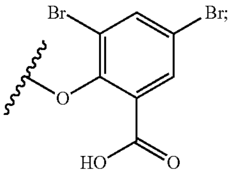

and if $X^1$ is an arylene substituted with one $R^3$, then $R^3$ is different from $—C(O)—R^1$ or $—C(O)—R^2$.

9. The compound of claim 8, or a salt, a stereoisomer, or a deuterated form thereof, wherein the leaving group is

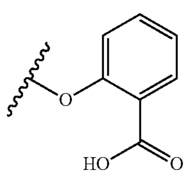

or

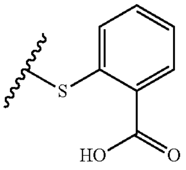

.

10. The compound of claim 8, or a salt, a stereoisomer, or a deuterated form thereof, wherein the leaving group is

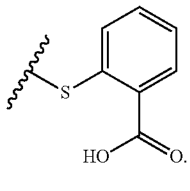 [SMILES: *Sc1ccccc1C(=O)O]

11. The compound of claim 8, or a salt, a stereoisomer, or a deuterated form thereof, wherein a is 1, 2, or 3.

12. The compound of claim 11, or a salt, a stereoisomer, or a deuterated form thereof, wherein each $R^4$ is halogen.

13. The compound of claim 11, or a salt, a stereoisomer, or a deuterated form thereof, wherein each $R^4$ is independently —F, —Cl, or —Br.

14. The compound of claim 8, or a salt, a stereoisomer, or a deuterated form thereof, wherein the leaving group is

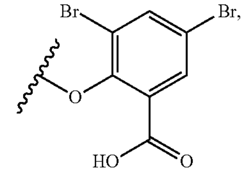

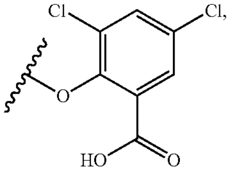

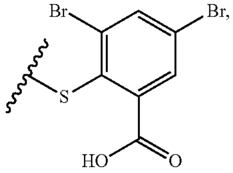

or

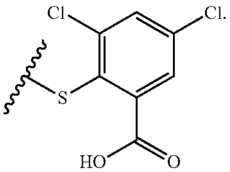

15. The compound of claim 8, or a salt, a stereoisomer, or a deuterated form thereof, wherein the leaving group is

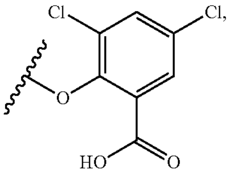

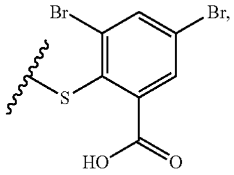

or

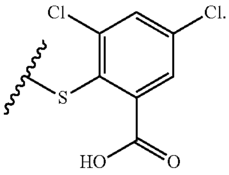

16. The compound of claim 1, or a salt, a stereoisomer, or a deuterated form thereof, wherein $R^1$ and $R^2$ are a leaving group, and wherein the leaving group is $—O—(C_{1-6}$ alkylene)-$SO_3H$.

17. The compound of claim 16, or a salt, a stereoisomer, or a deuterated form thereof, wherein the leaving group is $—O—(CH_2CH_2)—SO_3H$.

18. A compound which is:

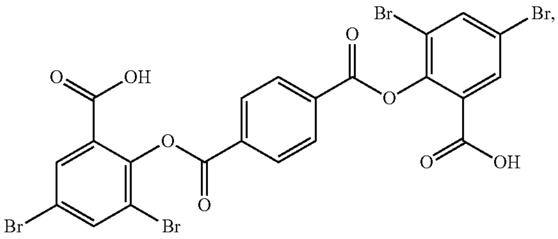

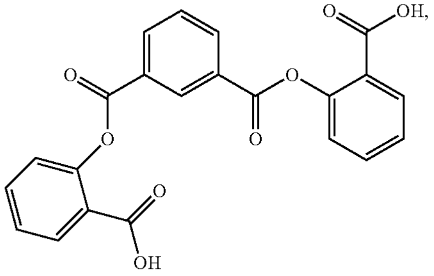

-continued

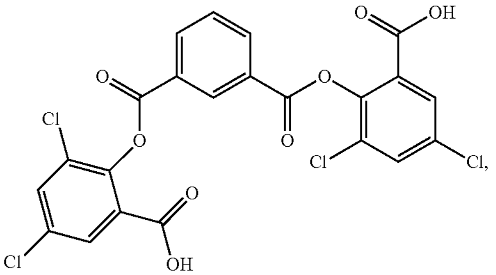

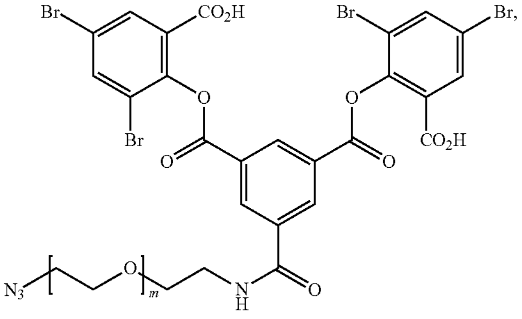

m = 4

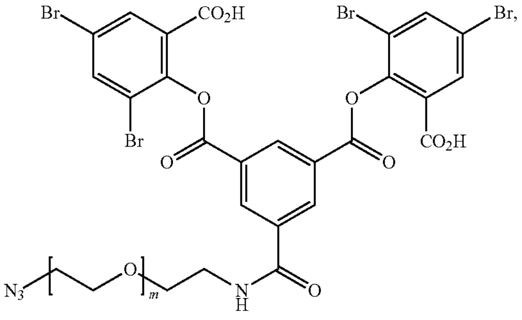

m = 9

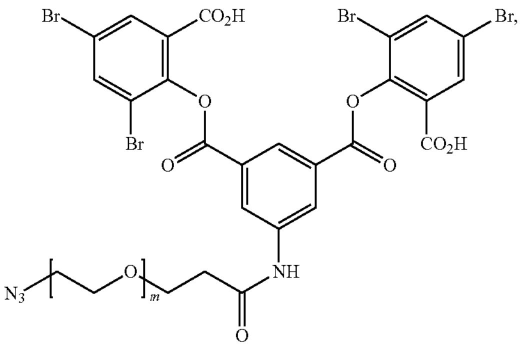

or m = 4

-continued

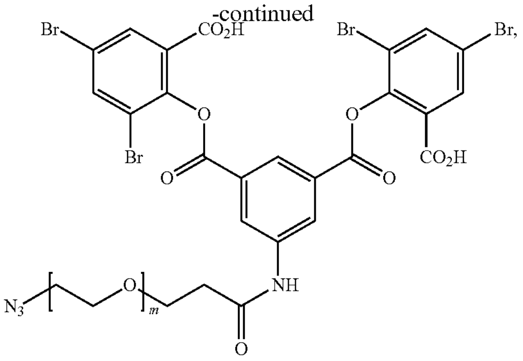

m = 9 or a salt, a stereoisomer, or a deuterated form thereof.

19. The compound of claim 7, or a salt, a stereoisomer, or a deuterated form thereof, wherein:

$R^A$ is H, —$C_{1-6}$ alkyl, aryl, —C(O)-aryl, —$SO_2(C_{1-6}$ alkyl), —$SO_2$-aryl, or —($C_{1-12}$ alkylene)-($OCH_2CH_2)_m$—$(CH_2)_n$—$N_3$, wherein m is an integer of 1-50, n is an integer of 0-25, and each alkyl, aryl, or alkylene is optionally and independently substituted with —$C_{1-6}$ alkyl; and $L^1$ and $L^2$ are each independently $C_{1-6}$ alkylene, $C_{2-6}$ alkenylene, $C_{2-6}$ alkynylene, $C_{3-6}$ cycloalkylene, $C_{3-6}$ cycloalkenylene, arylene, or heteroarylene, wherein $L^1$ and $L^2$ are optionally and independently substituted with 1-3 $R^3$.

20. The compound of claim 19, or a salt, a stereoisomer, or a deuterated form thereof, wherein $R^A$ is H, and $L^1$ and $L^2$ are each independently $C_{1-6}$ alkylene or $C_{2-6}$ alkenylene.

21. The compound of claim 19, or a salt, a stereoisomer, or a deuterated form thereof, wherein $X^2$ is

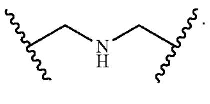 [SMILES: *CNC*]

22. The compound of claim 19, or a salt, a stereoisomer, or a deuterated form thereof, wherein $R^A$ is $C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl.

23. The compound of claim 19, or a salt, a stereoisomer, or a deuterated form thereof, wherein $X^2$ is

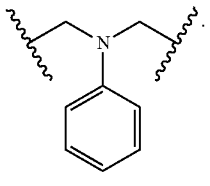 [SMILES: *CN(C*)c1ccccc1]

24. The compound of claim 19, or a salt, a stereoisomer, or a deuterated form thereof, wherein $R^A$ is —$SO_2$—$C_{1-6}$ alkyl, and $L^1$ and $L^2$ are each independently $C_{1-6}$ alkylene, or $C_{2-6}$ alkenylene.

25. The compound of claim 19, or a salt, a stereoisomer, or a deuterated form thereof, wherein $X^2$ is

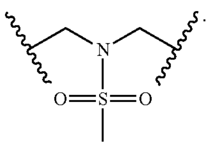 [SMILES: *CN(C*)S(C)(=O)=O]

26. The compound of claim 19, or a salt, a stereoisomer, or a deuterated form thereof, wherein $R^A$ is —$SO_2$—$C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl.

27. The compound of claim 19, or a salt, a stereoisomer, or a deuterated form thereof, wherein $X^2$ is

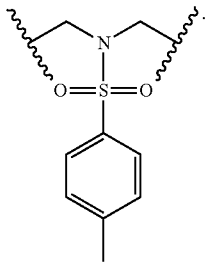 [SMILES: *CN(C*)S(=O)(=O)c1ccc(C)cc1]

28. The compound of claim 19, or a salt, a stereoisomer, or a deuterated form thereof, wherein $R^A$ is —C(O)—$C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl.

29. The compound of claim 19, or a salt, a stereoisomer, or a deuterated form thereof, wherein $X^2$ is

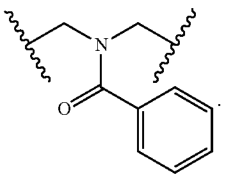 [SMILES: *CN(C*)C(=O)c1ccccc1]

30. The compound of claim 19, or a salt, a stereoisomer, or a deuterated form thereof, wherein $R^A$ is —($C_{1-6}$ alkylene)-$(OCH_2CH_2)_m$—$(CH_2)_n$—$N_3$, and $L^1$ and $L^2$ are each independently $C_{1-6}$ alkylene, or $C_{2-6}$ alkenylene, wherein m is an integer of 1-50, and n is an integer of 0-25.

31. The compound of claim 19, wherein $X^2$ is

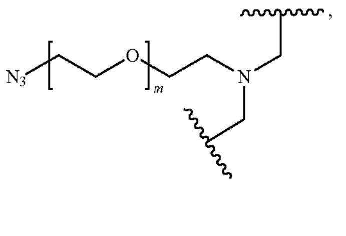

and m is 3.

32. The compound of claim 7, or a salt, a stereoisomer, or a deuterated form thereof, wherein $R^1$ and $R^2$ are a leaving group, and wherein:

the leaving group is

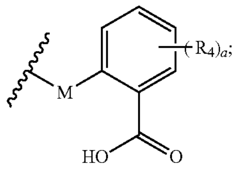

M is O or S;

each $R^4$ is independently halogen or —$C_{1-6}$ alkyl; and a is an integer of 0-4.

33. The compound of claim 32, or a salt, a stereoisomer, or a deuterated form thereof, wherein the leaving group is

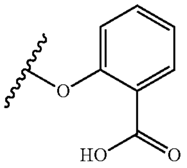

or

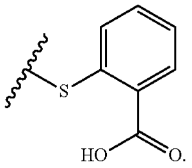

34. The compound of claim 32, or a salt, a stereoisomer, or a deuterated form thereof, wherein the leaving group is

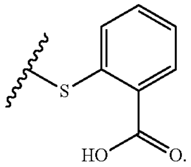 [SMILES: *Sc1ccccc1C(=O)O]

35. The compound of claim 32, or a salt, a stereoisomer, or a deuterated form thereof, wherein a is 1, 2, or 3.

36. The compound of claim 35, or a salt, a stereoisomer, or a deuterated form thereof, wherein each $R^4$ is halogen.

37. The compound of claim 35, or a salt, a stereoisomer, or a deuterated form thereof, wherein each $R^4$ is independently —F, —Cl, or —Br.

38. The compound of claim 32, or a salt, a stereoisomer, or a deuterated form thereof, wherein the leaving group is

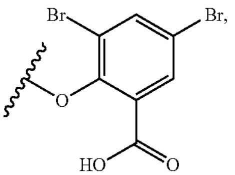

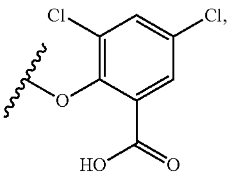

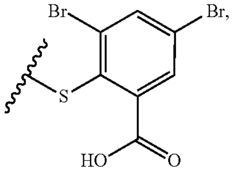

or

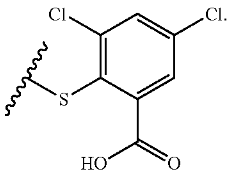

39. The compound of claim 32, or a salt, a stereoisomer, or a deuterated form thereof, wherein the leaving group is

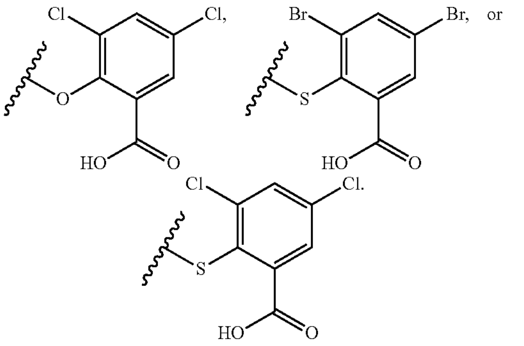

40. The compound of claim 7, or a salt, a stereoisomer, or a deuterated form thereof, wherein $R^1$ and $R^2$ are a leaving group, and wherein the leaving group is —O—($C_{1-6}$ alkylene)-$SO_3H$.

41. The compound of claim 40, or a salt, a stereoisomer, or a deuterated form thereof, wherein the leaving group is —O—($CH_2CH_2$)—$SO_3H$.

42. The compound of claim 7, wherein the compound is:

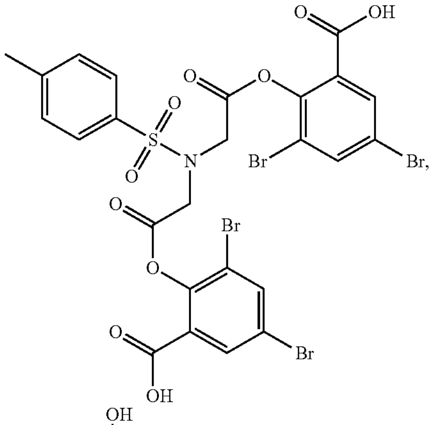

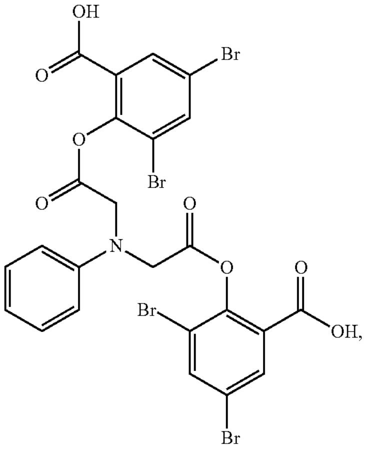

-continued

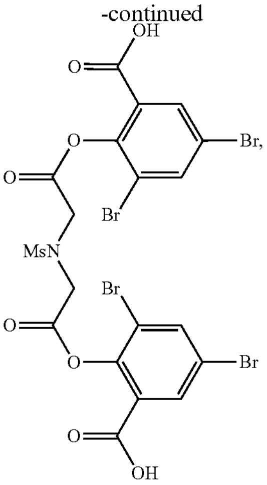

or

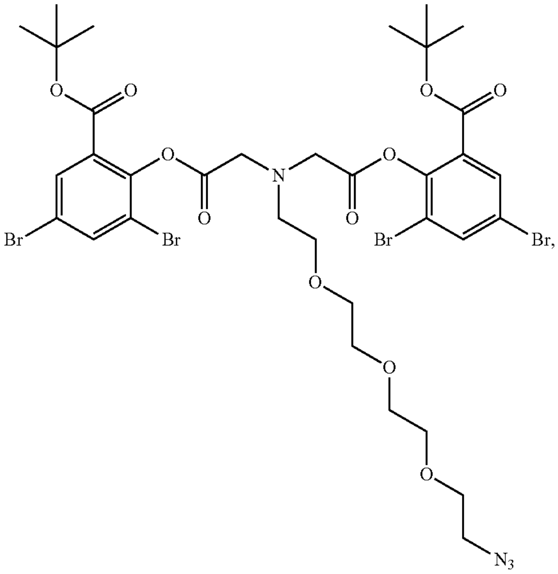

or a salt, a stereoisomer, or a deuterated form thereof.

* * * * *